(12) United States Patent
Greer et al.

(10) Patent No.: US 11,820,748 B2
(45) Date of Patent: *Nov. 21, 2023

US011820748B2

(54) SOLID STATE FORMS OF (S)-2-(((S)-6,8-DIFLUORO-1,2,3,4-TETRAHYDRONAPHTHALEN-2-YL)AMINO)-N-(1-(2-METHYL-1-(NEOPENTYLAMINO)PROPAN-2-YL)-1H-IMIDAZOL-4-YL)PENTANAMIDE AND USES THEREOF

(71) Applicant: Pfizer Inc., New York, NY (US)

(72) Inventors: Elaine Greer, Groton, CT (US); Stephen Anderson, Stonington, CT (US); Mark Maloney, East Lyme, CT (US); Shu Yu, Salem, CT (US); Ekaterina Albert, West Lafayette, IN (US); Emily Rigsbee, West Lafayette, IN (US)

(73) Assignee: PFIZER INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,442

(22) Filed: Jan. 27, 2023

(65) Prior Publication Data

US 2023/0167069 A1 Jun. 1, 2023

Related U.S. Application Data

(60) Continuation of application No. 18/157,592, filed on Jan. 20, 2023, which is a division of application No.
(Continued)

(51) Int. Cl.
*C07D 233/88* (2006.01)
*A61K 31/40* (2006.01)

(52) U.S. Cl.
CPC ............ *C07D 233/88* (2013.01); *A61K 31/40* (2013.01); *C07B 2200/13* (2013.01)

(58) Field of Classification Search
CPC .... C07D 233/88; A61K 31/40; C07B 2200/13
See application file for complete search history.

(56) References Cited

U.S. PATENT DOCUMENTS

| 7,342,118 B2 | 3/2008 | Brodney et al. |
| 7,795,447 B2 | 9/2010 | Brodney et al. |
| | (Continued) | |

FOREIGN PATENT DOCUMENTS

| WO | WO-0049037 A1 | 8/2000 |
| WO | WO-0210141 A1 | 2/2002 |
| | (Continued) | |

OTHER PUBLICATIONS

The United States Pharmacopeia, 23$^{rd}$ ed., 1843-4, USP-NF, United States (1995).
(Continued)

*Primary Examiner* — Amanda L. Aguirre
(74) *Attorney, Agent, or Firm* — Blank Rome LLP

(57) ABSTRACT

The present disclosure relates to: a) solid state forms of hydrobromide salts of Compound 1; b) pharmaceutical compositions comprising one or more solid state forms of hydrobromide salts of Compound 1, and, optionally, a pharmaceutically acceptable carrier; c) methods of treating tumors or cancers by administering one or more solid state forms of hydrobromide salts of Compound 1 to a subject in need thereof; and d) methods for the preparation of solid state forms of Compound 1.

9 Claims, 32 Drawing Sheets

Related U.S. Application Data

17/180,296, filed on Feb. 19, 2021, now Pat. No. 11,566,006, which is a continuation of application No. 16/886,622, filed on May 28, 2020, now Pat. No. 10,941,118, which is a division of application No. 16/818,863, filed on Mar. 13, 2020, now Pat. No. 10,710,966, which is a division of application No. 16/537,394, filed on Aug. 9, 2019, now Pat. No. 10,590,087.

(56) References Cited

U.S. PATENT DOCUMENTS

| | | | |
|---|---|---|---|
| 7,951,958 B2 | 5/2011 | Brodney et al. | |
| 10,590,087 B1* | 3/2020 | Greer | C07D 233/88 |
| 10,710,966 B1* | 7/2020 | Greer | C07D 233/88 |
| 10,941,118 B2* | 3/2021 | Greer | C07D 233/88 |
| 11,566,006 B2* | 1/2023 | Greer | C07D 233/88 |
| 2023/0087828 A1* | 3/2023 | Cheng | A61P 21/00 |

FOREIGN PATENT DOCUMENTS

| | | |
|---|---|---|
| WO | WO-2005092864 A1 | 10/2005 |
| WO | WO-2018045273 A2 | 3/2018 |
| WO | WO-2019053727 A1 | 3/2019 |

OTHER PUBLICATIONS

"Nirogacestat for Adults with Desmoid Tumor/Aggressive Fibromatosis (DT/AF) (DeFi)," ClinicalTrials.gov, https://clinicaltrials.gov/ct2/show/NCT03785964?term=nirogacestat&rank=1, accessed on Aug. 14, 2019, 9 pages.

"PF-03084014 hydrobromide," Millipore Sigma, SigmaAldrich.com, https://www.sigmaaldrich.com/catalog/product/sigma/pz0298?lang=en&region=US-, accessed on Aug. 14, 2019, 5 pages.

"A Study Evaluating PF-03084014 In Patients With Advanced Breast Cancer With Or Without Notch Alterations," ClinicalTrials.gov, https://clinicaltrials.gov/ct2/show/NCT02299635?term=03084014&rank=1, accessed on Aug. 15, 2019, 9 pages.

"Gamma Secretase Inhibitor PF-03084014 in Treating Patients With AIDS-Associated Kaposi Sarcoma," ClinicalTrials.gov, https://clinicaltrials.gov/ct2/show/NCT02137564?term=03084014&rank=2, accessed on Aug. 15, 2019, 11 pages.

"A Study Of PF-03084014 In Japanese Patients With Advanced Solid Tumors," ClinicalTrials.gov, https://clinicaltrials.gov/ct2/show/NCT02462707?term=03084014&rank=3, accessed on Aug. 15, 2019, 6 pages.

"Phase II Trial of the Gamma-Secretase Inhibitor PF-03084014 in Adults With Desmoid Tumors/Aggressive Fibromatosis," ClinicalTrials.gov, https://clinicaltrials.gov/ct2/show/NCT01981551?term=03084014&rank=4, accessed on Aug. 15, 2019, 10 pages.

"Biomarker Research Study for PF-03084014 in cHEmoresistant Triple-negative Breast cAncer (RHEA)," ClinicalTrials.gov, https://clinicaltrials.gov/ct2/show/NCT02338531?term=03084014&rank=5, accessed on Aug. 15, 2019, 7 pages.

"A Study Evaluating The PF-03084014 In Combination With Docetaxel In Patients With Advanced Breast Cancer," ClinicalTrials.gov, https://clinicaltrials.gov/ct2/show/NCT01876251?term=03084014&rank=6, accessed on Aug. 15, 2019, 11 pages.

"Compassionate Use Protocol for PF-03084014 in Patients With Advanced Solid Tumor Malignancies," ClinicalTrials.gov, https://clinicaltrials.gov/ct2/show/NCT02955446?term=03084014&rank=7, accessed on Aug. 15, 2019, 5 pages.

"Study Of PF-03084014 In Combination With Gemcitabine And Nab-Paclitaxel In Patients With Metastatic Pancreatic Adenocarcinoma Not Previously Treated With Anticancer Therapies," ClinicalTrials.gov, https://clinicaltrials.gov/ct2/show/NCT02109445?term=03084014&rank=8, accessed on Aug. 15, 2019, 13 pages.

"A Trial In Patients With Advanced Cancer And Leukemia," ClinicalTrials.gov, https://clinicaltrials.gov/ct2/show/NCT00878189?term=03084014&rank=9, accessed on Aug. 15, 2019, 7 pages.

Brodney, M.A., et al., "Design, Synthesis, and in vivo characterization of a novel series of tetralin amino imidazoles as γ-secretase inhibitors: Discovery of PF-3084014," *Bioorganic & Medicinal Chemistry Letters* 21:2637-40, Elsevier, Netherlands (2011).

Kummar, S., et al., "Clinical Activity of the γ-Secretase Inhibitor PF-03084014 in Adults With Desmoid Tumors (Aggressive Fibromatosis)," *Journal of Clinical Oncology* 35(14):1561-9, American Society of Clinical Oncology, United States (2017).

Shang, H., et al., "Targeting the Notch Pathway: A Potential Therapeutic Approach for Desmoid Tumors," *Cancer 121*(22):4088-96, John Wiley and Sons Inc., United States (2015).

Wei, P., et al., "Evaluation of Selective γ-Secretase Inhibitor PF-03084014 for Its Antitumor Efficacy and Gastrointestinal Safety to Guide Optimal Clinical Trial Design," *Molecular Cancer Therapeutics 9*(6): 1618-28, American Association for Cancer Research, United States (2010).

Aurora Building Blocks 4, Accession No. 1921685693 CHEMCATS, CAS Registry No. 1962925-29-6, Feb. 27, 2020, 2 pages.

International Search Report and Written Opinion for International Application No. PCT/US2019/045948, European Patent Office, Netherlands, dated Jul. 6, 2020, 10 pages.

Co-pending Application, U.S. Appl. No. 18/049,073, inventors Cheng, S., et al., filed on Oct. 24, 2022 (Not Published).

Co-pending Application, U.S. Appl. No. 17/938,590, inventors Cheng, S., et al., filed on Oct. 6, 2022 (Not Published).

Co-pending Application, U.S. Appl. No. 18/057,633, inventors Patterson, K., et al., filed on Nov. 21, 2022 (Not Published).

Co-pending Application, U.S. Appl. No. 18/157,592, inventors Greer, E., et al., filing date To Be Assigned (Not Published).

Giuseppe Curigliano, et al., "Phase I dose-finding study of the gamma secretase inhibitor PF-03084014 (PF-4014) in combination with docetaxel in patients (pts) with advanced triple-negative breast cancer (TNBC)", Journal of Clinical Oncology, vol. 33, No. 15, suppl., May 20, 2015, p. 1068.

Noriyuki Takada, "API form screening and selection in drug discovery stage", Pharma Stage, 6(10):20-25, Jan. 15, 2007.

Kaufman, et al., "Transcriptional Profiling of Murine Retinas Undergoing Semi-Synchronous Cone Photorecptor Differentiation", Developmental Biology, 453:155-167 (2019).

Stahly, et al., "Salt Selection for Pharmaceuticals, Importance of screening for crystal polymorphs", Journal of Pharmaceutical Science and Technology, Japan, 2006, 66(6):435-439.

\* cited by examiner

SOLID STATE FORMS OF (S)-2-(((S)-6,8-DIFLUORO-1,2,3,4-TETRAHYDRONAPHTHALEN-2-YL)AMINO)-N-(1-(2-METHYL-1-(NEOPENTYLAMINO)PROPAN-2-YL)-1H-IMIDAZOL-4-YL)PENTANAMIDE AND USES THEREOF

CROSS-REFERENCE TO RELATED APPLICATIONS

The present application is a continuation of U.S. patent application Ser. No. 18/157,592, filed on Jan. 20, 2023, pending, which is a division of U.S. patent application Ser. No. 17/180,296, filed on Feb. 19, 2021, pending, which is a continuation of U.S. patent application Ser. No. 16/886,622, filed on May 28, 2020, now U.S. Pat. No. 10,941,118, which is a division of U.S. patent application Ser. No. 16/818,863, filed on Mar. 13, 2020, now U.S. Pat. No. 10,710,966, which is a division of Ser. No. 16/537,394, filed on Aug. 9, 2019, now U.S. Pat. No. 10,590,087, which are incorporated herein by reference in their entirety.

FIELD OF THE INVENTION

The present disclosure relates to: a) solid state forms of hydrobromide salts of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide ("Compound 1"); b) pharmaceutical compositions comprising one or more solid state forms of hydrobromide salts of Compound 1, and, optionally, a pharmaceutically acceptable carrier; c) methods of treating tumors or cancers by administering one or more solid state forms of hydrobromide salts of Compound 1 to a subject in need thereof; and d) methods for the preparation of solid state forms of hydrobromide salts of Compound 1.

BACKGROUND (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide ("Compound 1") is a gamma-secretase inhibitor which can inhibit AP-peptide production.

Not all compounds that are gamma-secretase inhibitors have characteristics affording the best potential to become useful therapeutics. Some of these characteristics include high affinity at the gamma-secretase, duration of gamma-secretase deactivation, oral bioavailability, tissue distribution, and stability (e.g., ability to formulate or crystallize, shelf life). Favorable characteristics can lead to improved safety, tolerability, efficacy, therapeutic index, patient compliance, cost efficiency, manufacturing ease, etc.

In addition, the isolation and commercial-scale preparation of a solid state form of hydrobromide salts of Compound 1 and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges.

Accordingly, there is a current need for one or more solid state forms of hydrobromide salts of Compound 1 that have an acceptable balance of these properties and can be used in the preparation of pharmaceutically acceptable solid dosage forms.

BRIEF SUMMARY OF THE INVENTION

In one aspect, the present disclosure relates to a solid form of a hydrobromide salt of Compound 1. In one embodiment, the solid form is a crystalline form of a hydrobromide salt of Compound 1. In one embodiment, the solid form is a crystalline form of a dihydrobromide salt of Compound 1. In another embodiment, the solid form is an amorphous form of the dihydrobromide salt of Compound 1.

In one aspect, the present disclosure relates to a crystalline form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I)

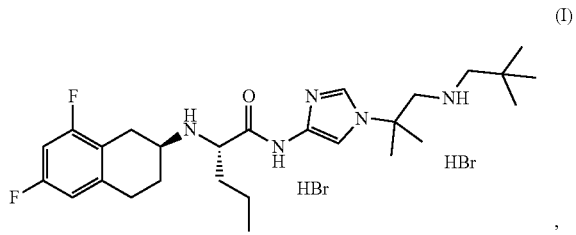 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

selected from the group consisting of:
a) crystalline Form A, wherein Form A is characterized by an XRPD pattern having peaks at 8.8±0.2, 9.8±0.2, and 23.3±0.2 degrees two theta;
b) crystalline Form B, wherein Form B is characterized by an XRPD pattern substantially as shown in FIG. 4;
c) crystalline Form D, wherein Form D is characterized by an XRPD pattern substantially as shown in FIG. 11;
d) crystalline Form E, wherein Form E is characterized by an XRPD pattern substantially as shown in FIG. 14;
e) crystalline Form F, wherein Form F is characterized by an XRPD pattern substantially as shown in FIG. 17;
f) crystalline Form F', wherein Form F' is characterized by an XRPD pattern substantially as shown in FIG. 18;
g) crystalline Form G, wherein Form G is characterized by an XRPD pattern substantially as shown in FIG. 21;
h) crystalline Form H, wherein Form H is characterized by an XRPD pattern substantially as shown in FIG. 22;
i) crystalline Form H', wherein Form H' is characterized by an XRPD pattern substantially as shown in FIG. 23;
j) crystalline Form J, wherein Form J is characterized by an XRPD pattern substantially as shown in FIG. 24;
k) crystalline Form K, wherein Form K is characterized by an XRPD pattern substantially as shown in FIG. 25;
l) crystalline Form L, wherein Form L is characterized by an XRPD pattern substantially as shown in FIG. 26;
m) crystalline Form M, wherein Form M is characterized by an XRPD pattern substantially as shown in FIG. 29; and
n) crystalline Form N, wherein Form N is characterized by an XRPD pattern substantially as shown in FIG. 30.

In one aspect, the present disclosure relates to crystalline Form A of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

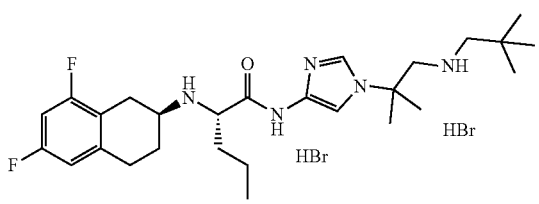
(I)

In one embodiment, crystalline Form A is anhydrous.

In another embodiment, the melting point of crystalline Form A is about 254° C.

In another embodiment, Form A is characterized by an XRPD pattern having peaks at 8.8±0.2, 9.8±0.2, and 23.3±0.2 degrees two theta. In another embodiment, Form A is characterized by an XRPD pattern having peaks at 8.8±0.2, 9.8±0.2, 23.3±0.2, 25.4±0.2, 28.0±0.2, and 29.3±0.2 degrees two theta. In another embodiment, Form A is characterized by an XRPD pattern having peaks at 8.8±0.2, 9.8±0.2, 20.0±0.2, 23.3±0.2, 25.4±0.2, 28.0±0.2, 29.3±0.2, and 32.5±0.2 degrees two theta.

In another embodiment, Form A is characterized by an XRPD pattern substantially as shown in FIG. 1. In another embodiment, Form A is characterized by a TGA profile substantially as shown in FIG. 2. In another embodiment, Form A is characterized by a DSC profile substantially as shown in FIG. 3.

In another embodiment, Form A has a unit cell that indexes as primitive monoclinic.

In another embodiment, Form A has a unit cell with an a value of about 10.035 Å, a b value of about 7.532 Å, and a c value of about 20.092 Å. In another embodiment, Form A has a unit cell with a volume of about 1518.1 Å³.

In another embodiment, Form A is substantially free of other polymorphic forms.

In one embodiment, Form A has a polymorphic purity of at least 90%. In one embodiment, Form A has a polymorphic purity of at least 99%.

In another embodiment, the Form A has one or more of a D[V,0.10] particle size between about 0.5 µm and about 15 µm, a D[V,0.50] particle size between about 2 µm and about 30 µm, a D[V,0.90] particle size between about 8 µm and about 600 or a D[4,3] particle size of about 5 µm to about 200 µm.

In one aspect, the present disclosure relates to crystalline Form B of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

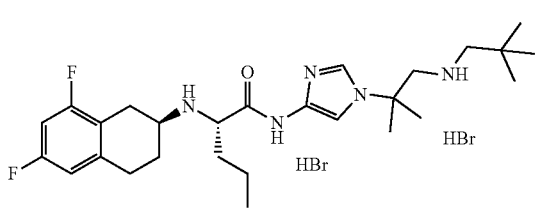
(I)

In one embodiment, Form B is characterized by an XRPD pattern substantially as shown in FIG. 4.

In another embodiment, Form B is substantially free of other polymorphic forms.

In another embodiment, Form B has a polymorphic purity of at least 90%. In another embodiment, Form B has a polymorphic purity of at least 99%.

In another embodiment, the Form B has one or more of a D[V,0.10] particle size between about 0.5 µm and about 15 µm, a D[V,0.50] particle size between about 2 µm and about 30 µm, a D[V,0.90] particle size between about 8 µm and about 600 or a D[4,3] particle size of about 5 µm to about 200 µm.

In one aspect, the present disclosure relates to crystalline Form C of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (II),

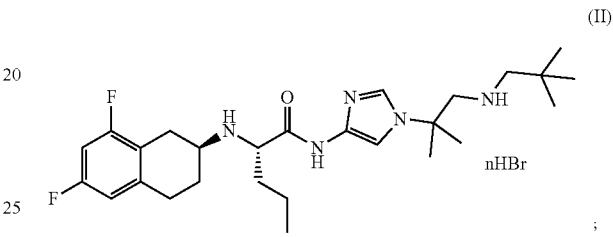
(II)

wherein n is about 1 to 3.

In one embodiment, Form C has one or more characteristics selected from the group consisting of a)-d):

a) an XRPD pattern substantially as shown in FIG. 5;

b) a TGA profile substantially as shown in FIG. 6;

c) a DSC profile substantially as shown in FIG. 7; and d) a TG-IR linked spectrum substantially as shown in a figure selected from a group consisting of FIGS. 8 to 10.

In another embodiment, Form C has a unit cell that indexes as primitive orthorhombic.

In another embodiment, Form C has a unit cell with an a value of about 7.491 Å, a b value of about 10.353 Å, and a c value of about 48.790 Å. In another embodiment, Form C has a unit cell with a volume of about 3783.9 Å³.

In another embodiment, the TGA exhibits that Form C loses at least 8 wt % between about 60° C. and about 190° C. In another embodiment, Form C exhibits a DSC thermogram that has a first endothermic event at about 39° C. and a second endothermic event at about 152° C.

In another embodiment, Form C is substantially free of other polymorphic forms.

In one embodiment, Form C has a polymorphic purity of at least 90%. In one embodiment, Form C has a polymorphic purity of at least 99%.

In another embodiment, the Form C has one or more of a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

In one aspect, the present disclosure relates to crystalline Form D of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

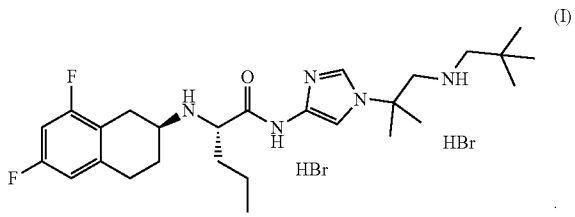 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

In one embodiment, Form D has one or more characteristics selected from the group consisting of a)-c):
a) an XRPD pattern substantially as shown in FIG. 11;
b) a TGA profile substantially as shown in FIG. 12A or FIG. 12B; and
c) a DSC profile substantially as shown in Line A or Line B of FIG. 13.

In another embodiment, Form D has a unit cell that indexes as primitive monoclinic. In another embodiment, Form D has a unit cell with an a value of about 18.465 Å, a b value of about 7.441 Å, and a c value of about 23.885 Å. In another embodiment, Form D has a unit cell with a volume of about 3250.4 Å$^3$.

In another embodiment, the TGA exhibits that Form D loses about 1.2 to about 2.5 wt % between about 24° C. and about 109° C.

In another embodiment, Form D exhibits a DSC thermogram that has an endothermic event at about 65° C.

In another embodiment, Form D is substantially free of other polymorphic forms.

In one embodiment, Form D has a polymorphic purity of at least 90%. In one embodiment, Form D has a polymorphic purity of at least 99%.

In another embodiment, the Form D has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form E of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I), (I)

In one embodiment, Form E has one or more characteristics selected from the group consisting of a)-c):
a) an XRPD pattern substantially as shown in FIG. 14;
b) a TGA profile substantially as shown in FIG. 15; and
c) a DSC profile substantially as shown in FIG. 16.

In another embodiment, the TGA exhibits that Form E loses about 8 wt % between about 28° C. and about 120° C.

In another embodiment, Form E exhibits a DSC thermogram that has an endothermic event at about 80° C.

In another embodiment, Form E is substantially free of other polymorphic forms.

In one embodiment, Form E has a polymorphic purity of at least 90%. In one embodiment, Form E has a polymorphic purity of at least 99%.

In another embodiment, the Form E has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one aspect, the present disclosure relates to crystalline Form F of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

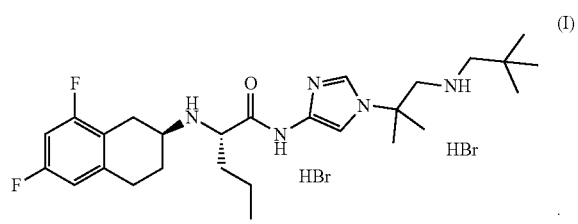 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

In another embodiment, Form F is characterized by an XRPD pattern substantially as shown in FIG. 17.

In another embodiment, Form F is substantially free of other polymorphic forms.

In one embodiment, Form F has a polymorphic purity of at least 90%. In one embodiment, Form F has a polymorphic purity of at least 99%.

In another embodiment, the Form F has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one aspect, the present disclosure relates to crystalline Form F' of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

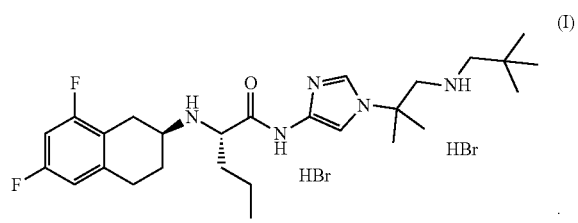 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

In one embodiment, Form F' has one or more characteristics selected from the group consisting of a)-b):
a) an XRPD pattern substantially as shown in FIG. 18; and
b) a TGA profile substantially as shown in FIG. 19; and
c) a DSC profile substantially as shown in FIG. 20.

In another embodiment, the TGA exhibits that Form F' loses about 12.6 wt % between about 24° C. and about 90° C. and loses about 15.6 wt % between about 97° C. to about 198° C.

In another embodiment, Form F' is substantially free of other polymorphic forms. In one embodiment, Form F' has a polymorphic purity of at least 90%. In one embodiment, Form F' has a polymorphic purity of at least 99%.

In another embodiment, the Form F' has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one aspect, the present disclosure relates to crystalline Form G of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

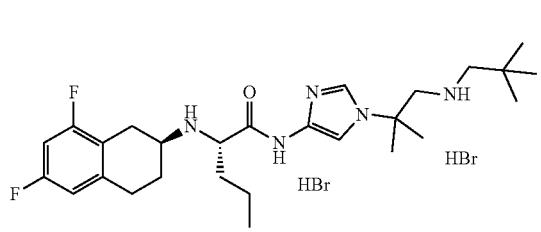
(I)

In one embodiment, Form G is characterized by an XRPD pattern substantially as shown in FIG. 21.

In another embodiment, Form G is substantially free of other polymorphic forms. In one embodiment, Form G has a polymorphic purity of at least 90%. In one embodiment, Form G has a polymorphic purity of at least 99%.

In another embodiment, the Form G has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form H of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I)

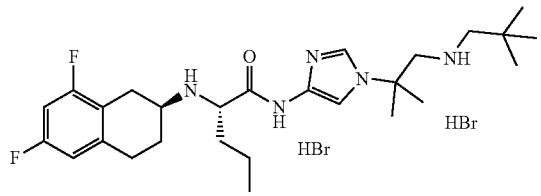
(I)

In one embodiment, Form H is characterized by an XRPD pattern substantially as shown in FIG. 22.

In another embodiment, Form H is substantially free of other polymorphic forms. In one embodiment, Form H has a polymorphic purity of at least 90%. In one embodiment, Form H has a polymorphic purity of at least 99%.

In another embodiment, the Form H has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form H' of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I)

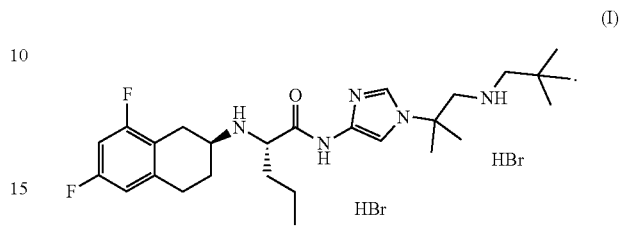
(I)

In one embodiment, Form H' is characterized by an XRPD pattern substantially as shown in FIG. 23.

In another embodiment, Form H' is substantially free of other polymorphic forms. In one embodiment, Form H' has a polymorphic purity of at least 90%. In one embodiment, Form H' has a polymorphic purity of at least 99%.

In another embodiment, the Form H' has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form J of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

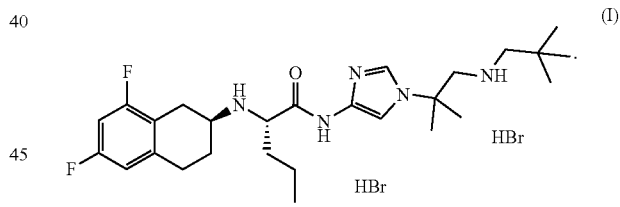
(I)

In one embodiment, Form J is characterized by an XRPD pattern substantially as shown in FIG. 24.

In another embodiment, Form J is substantially free of other polymorphic forms. In one embodiment, Form J has a polymorphic purity of at least 90%. In one embodiment, Form J has a polymorphic purity of at least 99%.

In another embodiment, the Form J has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form K of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

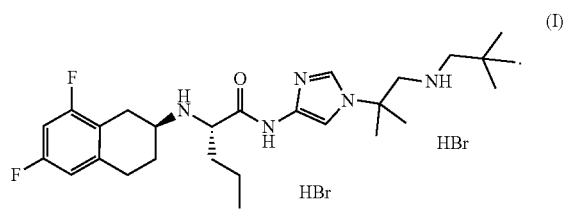 [SMILES: CCC[C@H](N[C@H]1CCc2cc(F)cc(F)c2C1)C(=O)Nc1cn(C(C)(C)CNCC(C)(C)C)cn1 ; Br ; Br]

In one embodiment, Form K is characterized by an XRPD pattern substantially as shown in FIG. 25.

In another embodiment, Form K is substantially free of other polymorphic forms. In one embodiment, Form K has a polymorphic purity of at least 90%. In one embodiment, Form K has a polymorphic purity of at least 99%.

In another embodiment, the Form K has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form L of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

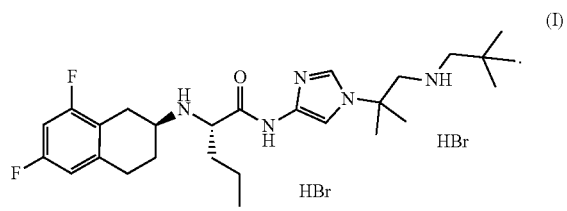 [SMILES: CCC[C@H](N[C@H]1CCc2cc(F)cc(F)c2C1)C(=O)Nc1cn(C(C)(C)CNCC(C)(C)C)cn1 ; Br ; Br]

In one embodiment, Form L has one or more characteristics selected from the group consisting of a)-c):

a) an XRPD pattern substantially as shown in FIG. 26;
b) a TGA profile substantially as shown in FIG. 27; and
c) a DSC profile substantially as shown in FIG. 28.

In another embodiment, Form L exhibits a DSC thermogram that has an endothermic event at about 157° C.

In another embodiment, Form L is substantially free of other polymorphic forms. In one embodiment, Form L has a polymorphic purity of at least 90%. In one embodiment, Form L has a polymorphic purity of at least 99%.

In another embodiment, the Form L has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to crystalline Form M of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I),

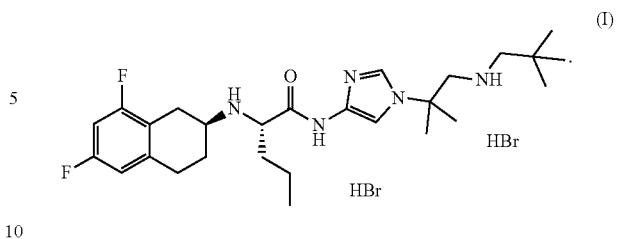

In one embodiment, Form M is characterized by an XRPD pattern substantially as shown in FIG. 29.

In another embodiment, Form M is substantially free of other polymorphic forms. In one embodiment, Form M has a polymorphic purity of at least 90%. In one embodiment, Form M has a polymorphic purity of at least 99%.

In another embodiment, the Form M has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one aspect, the present disclosure relates to crystalline Form N of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

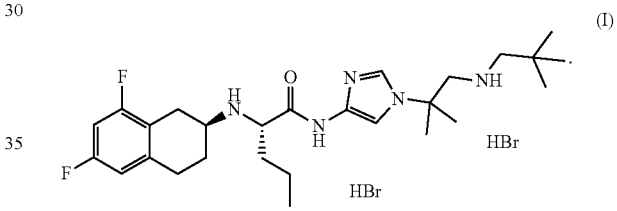

In one embodiment, Form N is characterized by an XRPD pattern substantially as shown in FIG. 30.

In another embodiment, Form N is substantially free of other polymorphic forms. In one embodiment, Form N has a polymorphic purity of at least 90%. In one embodiment, Form N has a polymorphic purity of at least 99%.

In another embodiment, the Form N has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one aspect, the present disclosure relates to amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I),

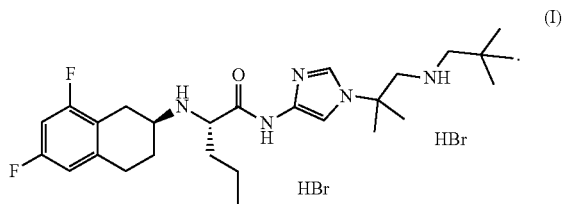 [SMILES: CCC[C@H](N[C@H]1CCc2cc(F)cc(F)c2C1)C(=O)Nc1cn(C(C)(C)CNCC(C)(C)C)cn1 ; Br ; Br]

In one embodiment, the amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) is characterized by an XRPD pattern substantially as shown in FIG. 31.

In another embodiment, the amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) is substantially free of polymorphic forms. In one embodiment, the amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) has a polymorphic purity of at least 90%. In one embodiment, the amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) has a polymorphic purity of at least 99%.

In another embodiment, the amorphous form has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm.

In one aspect, the present disclosure relates to a composition comprising a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide has one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 In one embodiment, the hydrobromide salt of (S)-2-(((S)-6,8-difluoro-1,2,3,4-tetrahydronaphthalen-2-yl)amino)-N-(1-(2-methyl (neopentylamino) propan-2-yl)-1H-imidazol-4-yl)pentanamide is amorphous form. In one embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide is a crystalline form.

In one embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide is a compound of Formula (I)

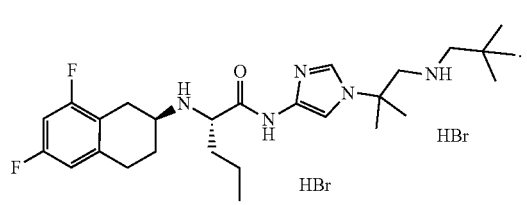

(I)

In another embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide is a compound of Formula (II)

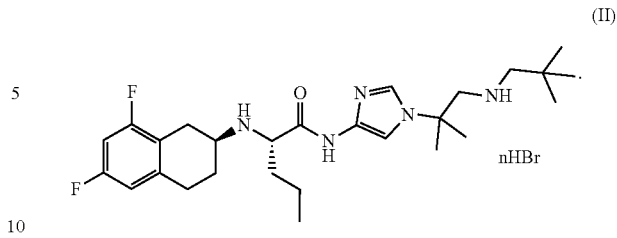

(II)

In another embodiment, the crystalline form is selected from the group consisting of Form A, Form B, Form C, Form D, Form E, Form F, Form F', Form G, Form H, Form H', Form J, Form K, Form L, Form M, and Form N. In another embodiment, the crystalline form is Form A.

In one aspect, the present disclosure relates to a pharmaceutical composition comprising one or more of forms or compositions discussed above and a pharmaceutically acceptable carrier. In one embodiment, the pharmaceutical composition comprises crystalline Form A of the compound of Formula (I). In one embodiment, the pharmaceutical composition is a tablet. In one embodiment, the pharmaceutical composition comprises about 25 mg to about 400 mg of the hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide. In one embodiment, the pharmaceutical composition comprises about 50 mg of the hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide. In one embodiment, the pharmaceutical composition comprises about 100 mg of the hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide. In one embodiment, the pharmaceutical composition comprises about 150 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide.

In one aspect, the present disclosure relates to a method of treating tumors or cancer comprising administering to a subject in need of such treatment one or more of Forms A-N or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide discussed above. In one embodiment, the method of treating tumors or cancer comprises administering to a subject in need of such treatment crystalline Form A of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide. In one aspect, the present disclosure relates to a method of treating tumors or cancer comprising administering to a subject in need of such treatment a pharmaceutical composition comprising one or more of Forms A-N or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl) pentanamide discussed above and a pharmaceutically acceptable carrier. In one embodiment, the method of treating tumors or cancer comprises administering to a subject in need of such treatment a pharmaceutical composition comprising crystalline Form A of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide and a pharmaceutically acceptable carrier. In one embodiment of the methods, the tumor is desmoid tumors. In one embodiment of the methods, the cancer is selected from the group consisting of multiple myeloma, a cancer having a mutation in a Notch pathway gene, adenoid cystic carcinoma, and T-cell acute lymphoblastic leukemia. In another embodiment of the methods, the cancer is multiple myeloma. In another embodiment, the cancer is one with a mutation in a Notch pathway gene. In another embodiment, the cancer is adenoid cystic carcinoma. In another embodiment, the cancer is T-cell acute lymphoblastic leukemia. In another embodiment, the subject is administered about 50 mg to about 500 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide daily. In another embodiment, the subject is administered about 100 mg to about 400 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide daily. In another embodiment, the subject is administered about 300 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide daily. In another embodiment, the subject is administered about 200 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide daily. In another embodiment, the total daily dose is provided as two separate doses. In another embodiment, the total daily dose is provided as two separate doses of 150 mg. In another embodiment, the total daily dose is provided as two separate doses of 100 mg.

In one aspect, the present disclosure relates to a use of one or more of Forms A-N or amorphous forms of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide discussed above for the manufacture of a medicament for treating tumors or cancer. In one embodiment, the present disclosure relates to a use of crystalline Form A of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide for the manufacture of a medicament for treating tumors or cancer. In one embodiment, the present disclosure relates to the pharmaceutical composition discussed above for treating tumors or cancer. In one embodiment, the use is for treating desmoid tumors. In one embodiment, the use is for treating cancer selected from the group consisting of multiple myeloma, a cancer having a mutation in a Notch pathway gene, adenoid cystic carcinoma, and T-cell acute lymphoblastic leukemia.

In one aspect, the present disclosure relates to one or more of Forms A-N or amorphous forms of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide discussed above for use in a method for treatment of tumors or cancer. In one embodiment, the present disclosure relates to the pharmaceutical composition discussed above for use in a method for treatment of tumors or cancer. In one embodiment, the use is for treating desmoid tumors. In one embodiment, the use is for treating cancer selected from the group consisting of multiple myeloma, a cancer having a mutation in a Notch pathway gene, adenoid cystic carcinoma, and T-cell acute lymphoblastic leukemia.

DETAILED DESCRIPTION OF THE INVENTION

I. Definitions

Figure 1:
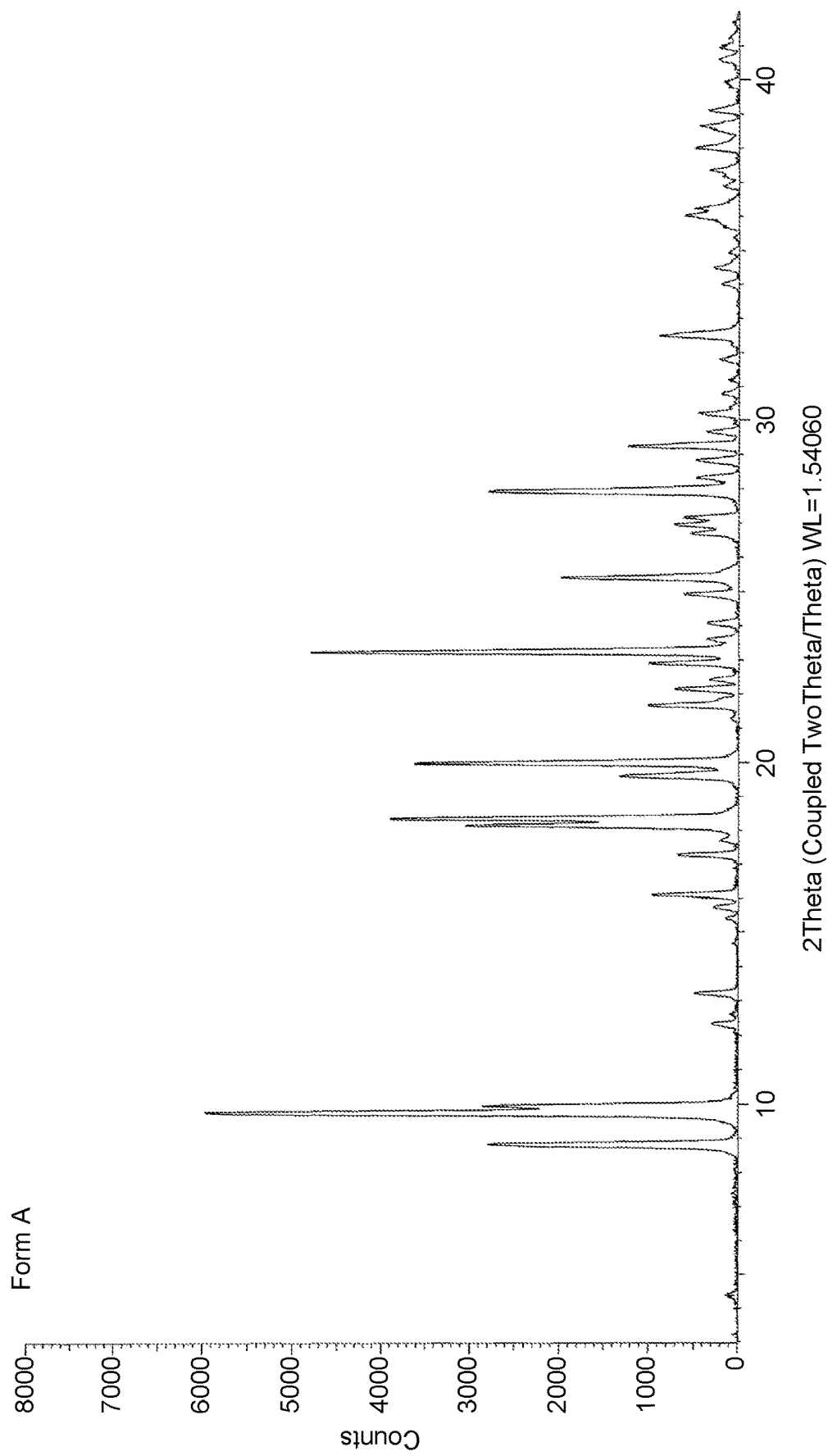
FIG. 1 is a powder X-ray diffraction pattern ("XRPD") corresponding to crystalline Form A.

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "Compound 1" refers to the single enantiomer (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy*, 21st Edition, Lippincott Williams & Wilkins: Philadelphia, PA, 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; Pharmaceutical Preformulation and Formulation, Gibson Ed., CRC Press LLC: Boca Raton, FL, 2004 (incorporated herein by reference).

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease.

As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "solvate" refers to a compound provided herein or a salt thereof, which further includes a stoichiometric or non-stoichiometric amount of solvent bound by non-covalent intermolecular forces. Where the solvent is water, the solvate is a hydrate. Where the solvent includes ethanol, the compound can be an ethanol solvate.

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences*, 18$^{th}$ ed., Mack Publishing, Easton PA, 173 (1990); *The United States Pharmacopeia*, 23$^{rd}$ ed, 1843-1844 (1995) (incorporated herein by reference).

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

The term "amorphous" as applied to a compound refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition").

The term "anhydrate" as applied to a compound refers to a solid state wherein the compound contains no structural water within the crystal lattice.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Solid State Forms

The present disclosure relates to solid state forms of the hydrobromide salt of Compound 1. As with all pharmaceutical compounds and compositions, the chemical and physical properties of the hydrobromide salt of Compound 1 are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactability, handling, flow and blend; and (6) filtration properties. These properties can affect, for example, the processing and storage of the compound and pharmaceutical compositions comprising the compound.

Solid state forms of the hydrobromide salt of Compound 1 that improve upon one or more of these properties relative to other solid state forms of the compound are desirable. Isolating pharmaceutically acceptable solid state forms of the compound that can be manufactured and formulated on a commercial-scale has been a challenge.

In one aspect, the present disclosure relates to a crystalline form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I)

Figure 4:
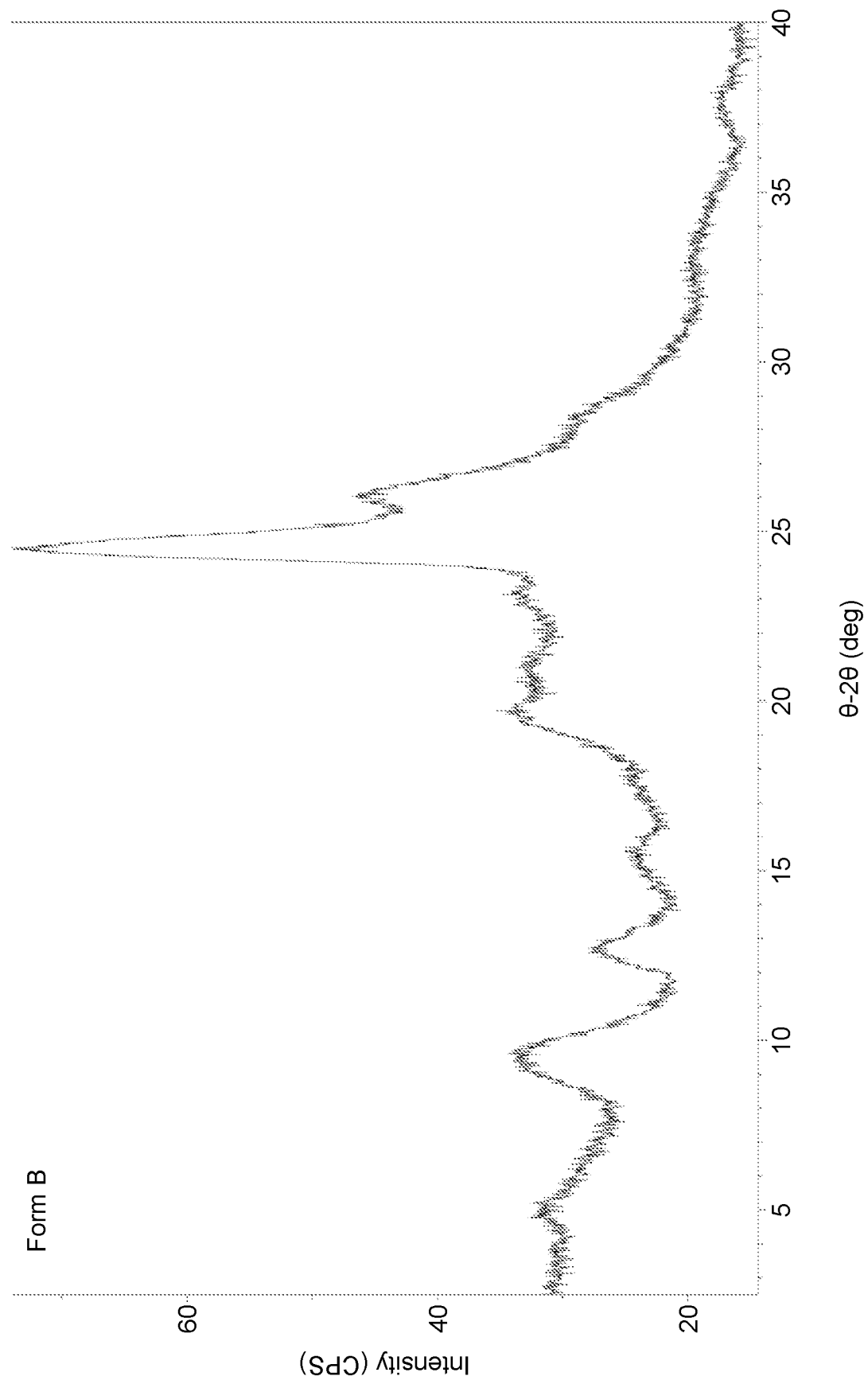
FIG. 4 is an XRPD corresponding to crystalline Form B.
Figure 11:
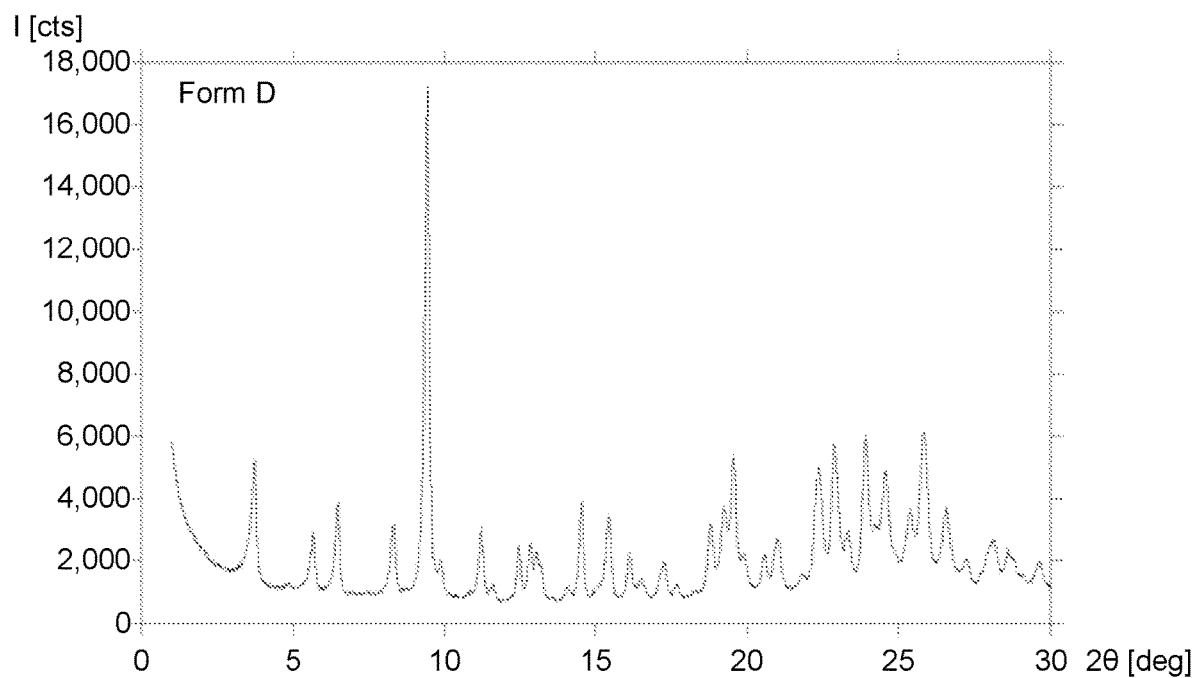
FIG. 11 is an XRPD corresponding to crystalline Form D.
Figure 14:
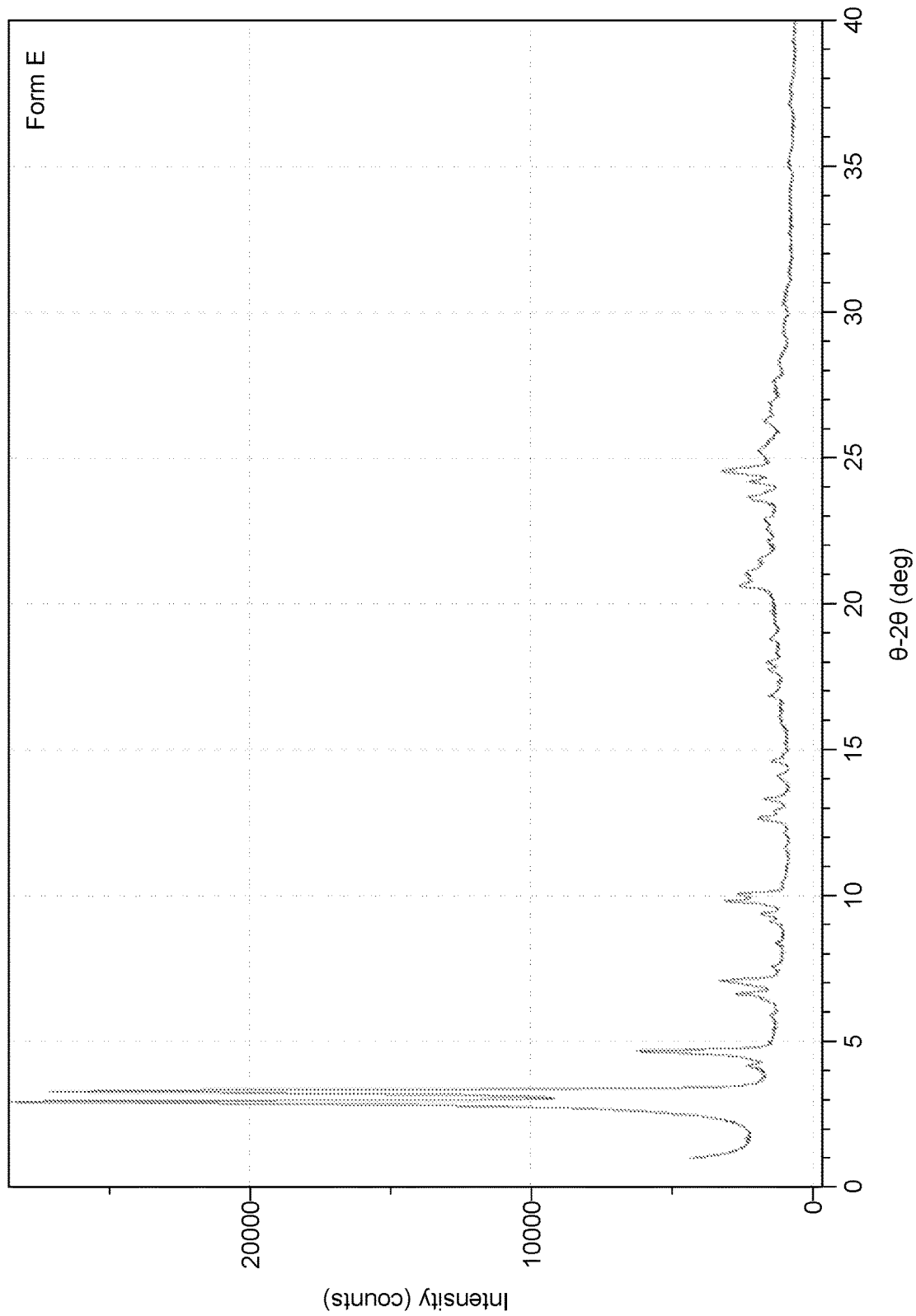
FIG. 14 is an XRPD corresponding to crystalline Form E.
Figure 17:
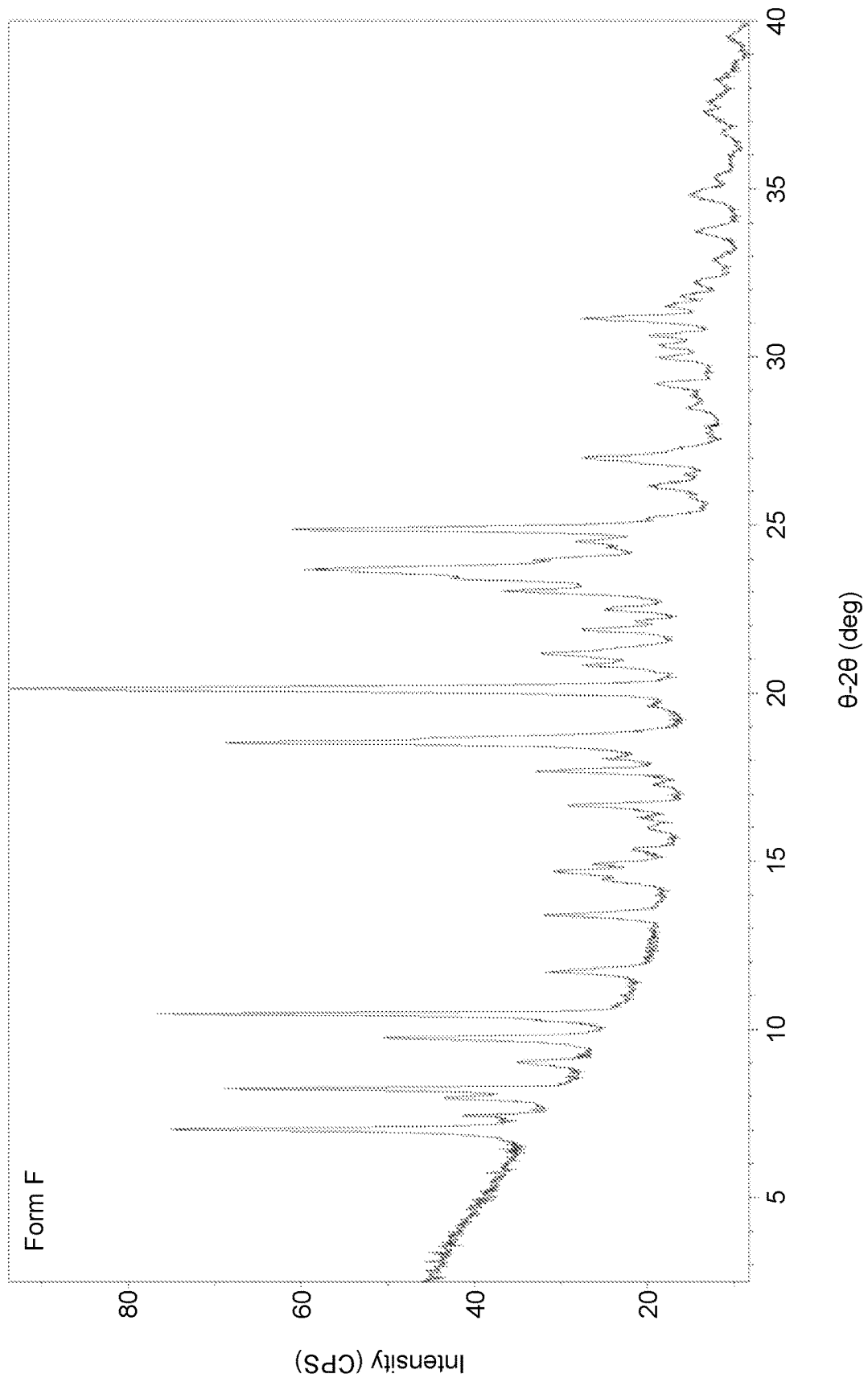
FIG. 17 is an XRPD corresponding to crystalline Form F.
Figure 18:
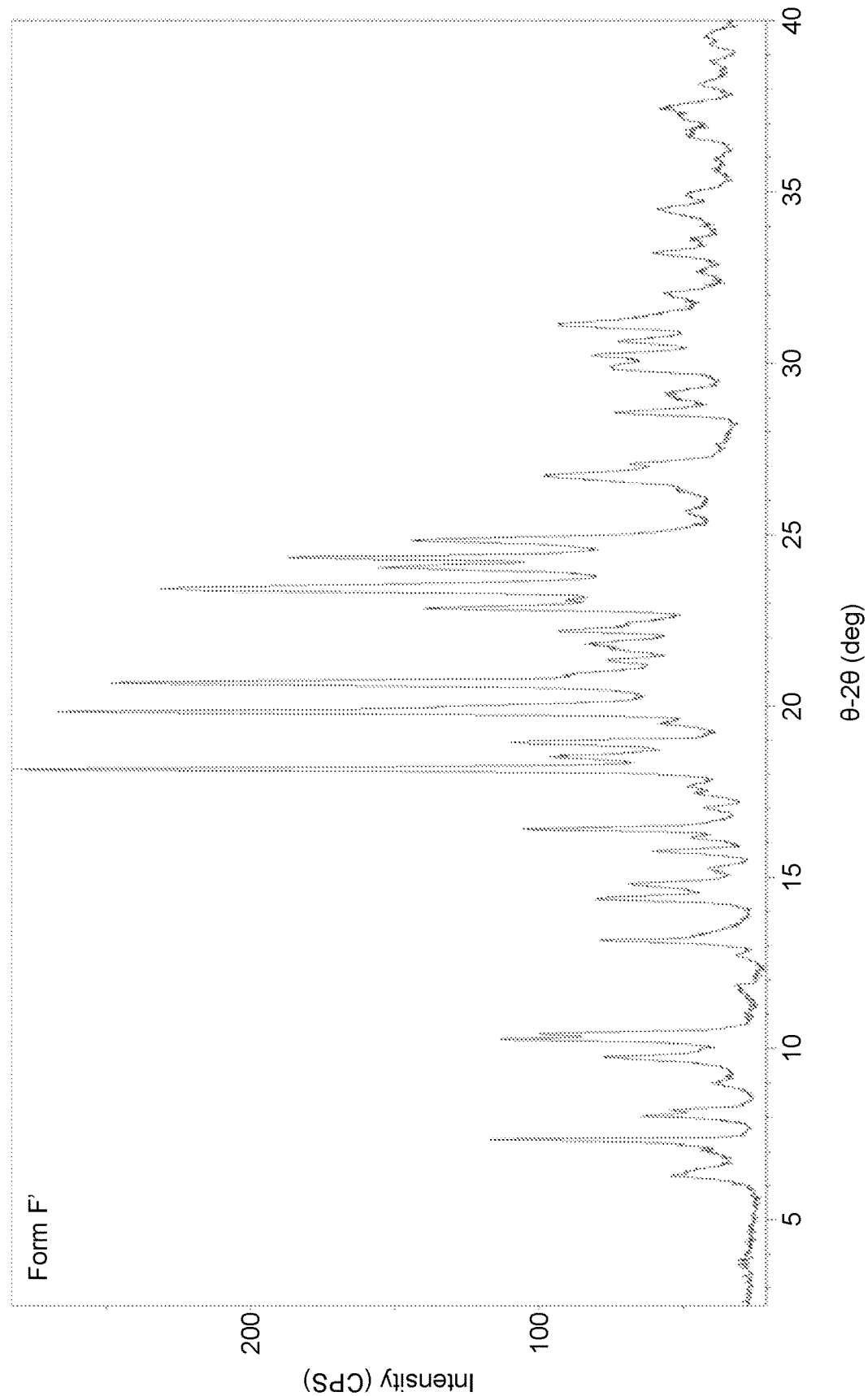
FIG. 18 is an XRPD corresponding to crystalline Form F'.
Figure 21:
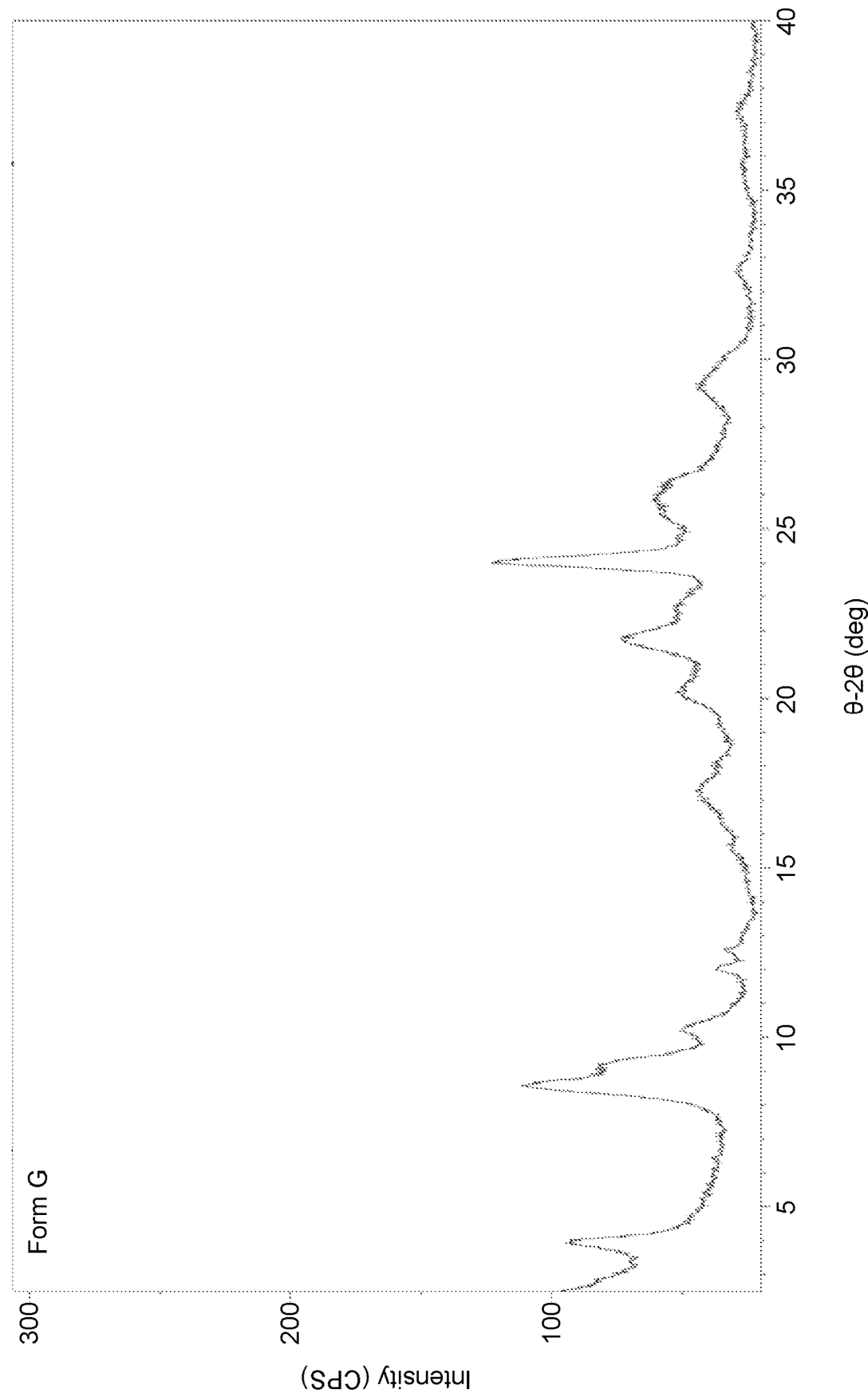
FIG. 21 is an XRPD corresponding to crystalline Form G.
Figure 22:
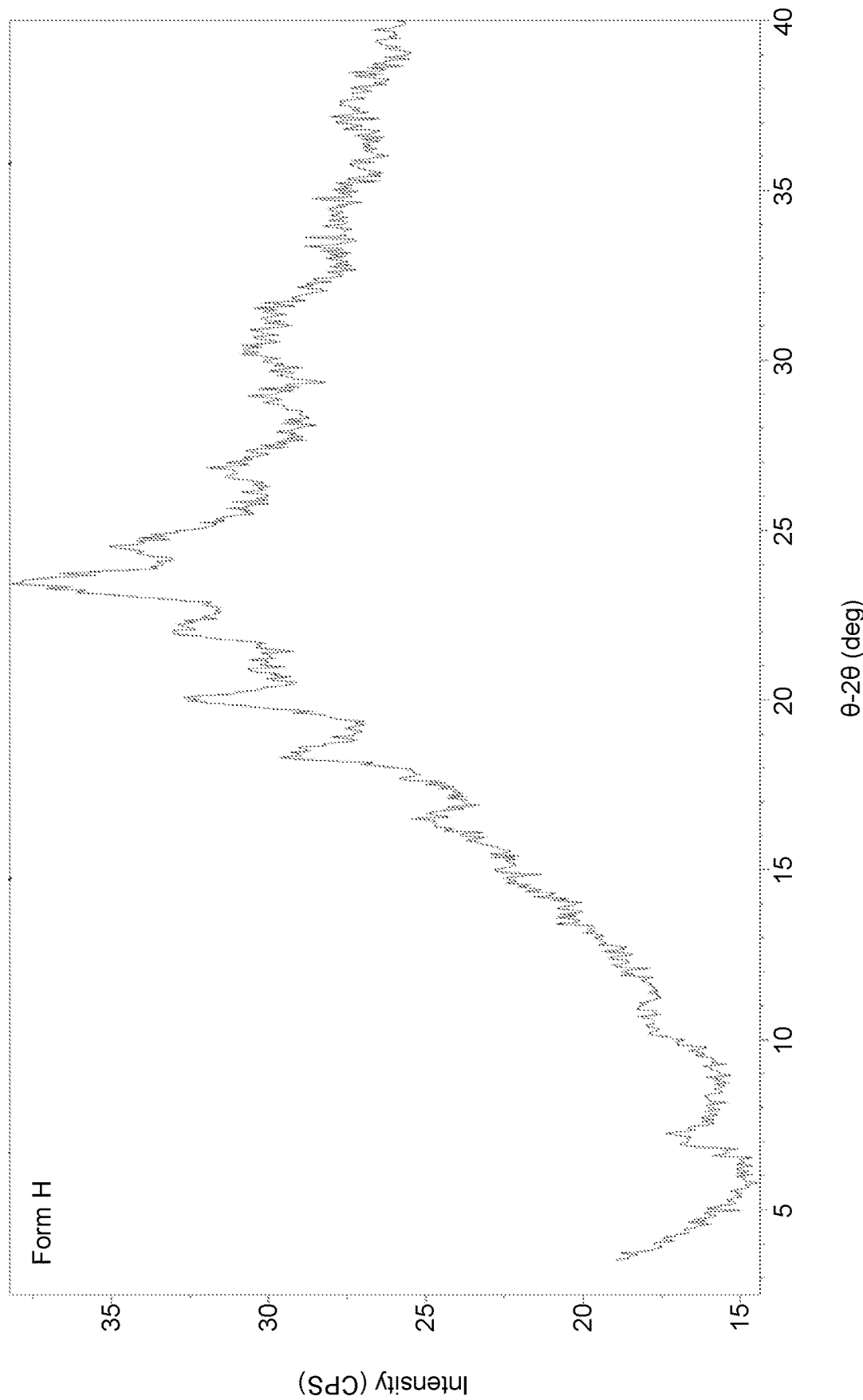
FIG. 22 is an XRPD corresponding to crystalline Form H.
Figure 23:
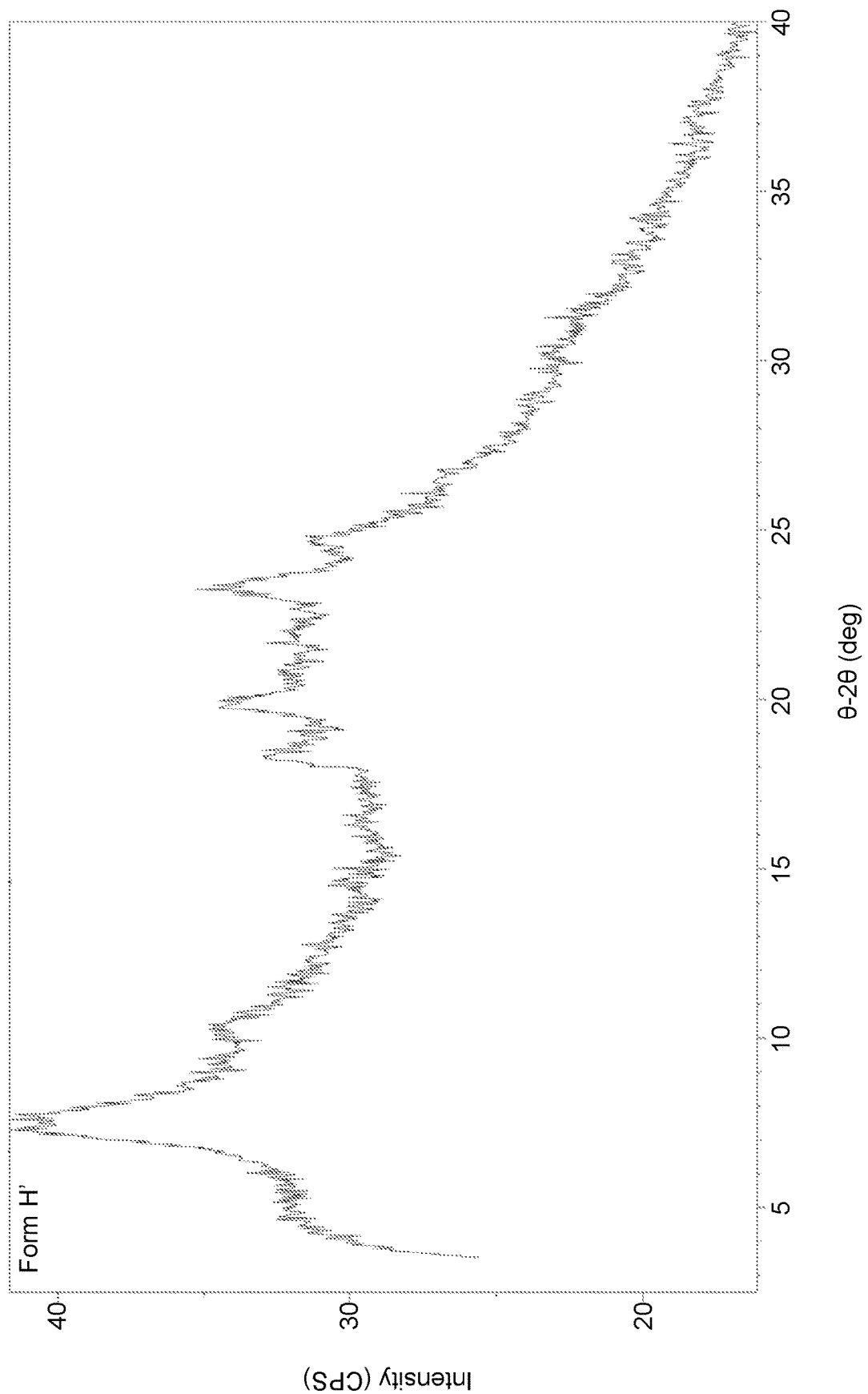
FIG. 23 is an XRPD corresponding to crystalline Form H'.
Figure 24:
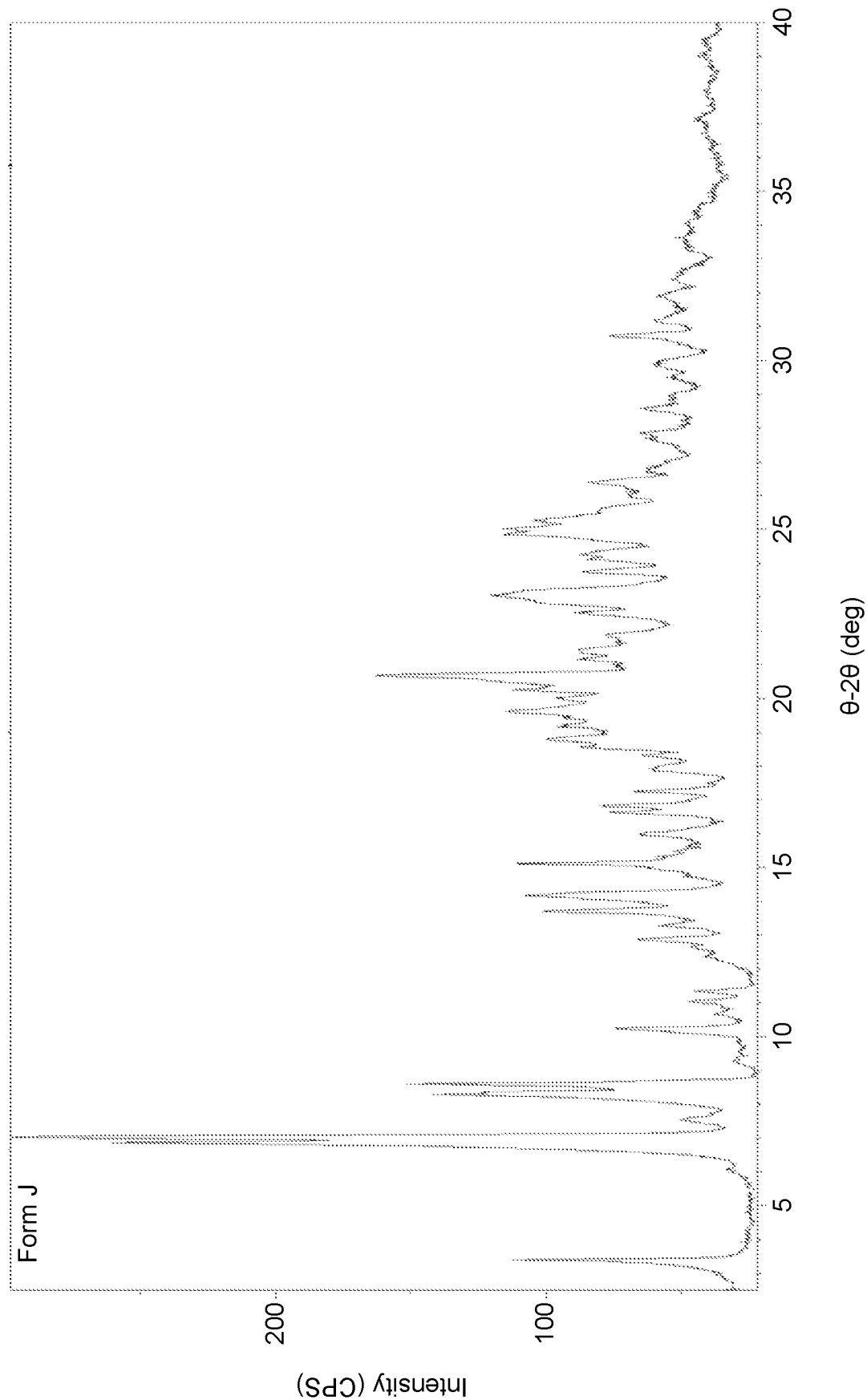
FIG. 24 is an XRPD corresponding to crystalline Form J.
Figure 25:
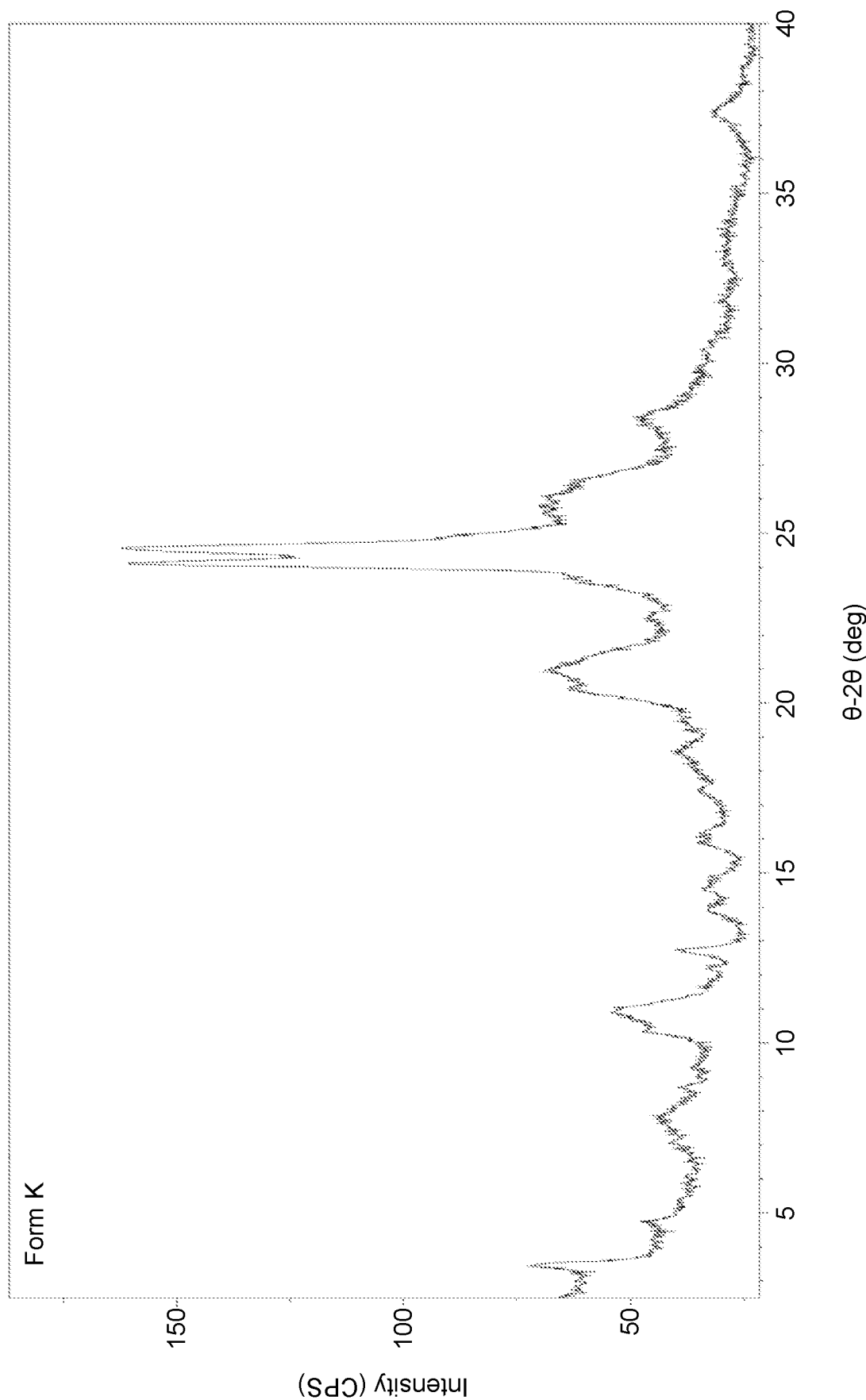
FIG. 25 is an XRPD corresponding to crystalline Form K.
Figure 26:
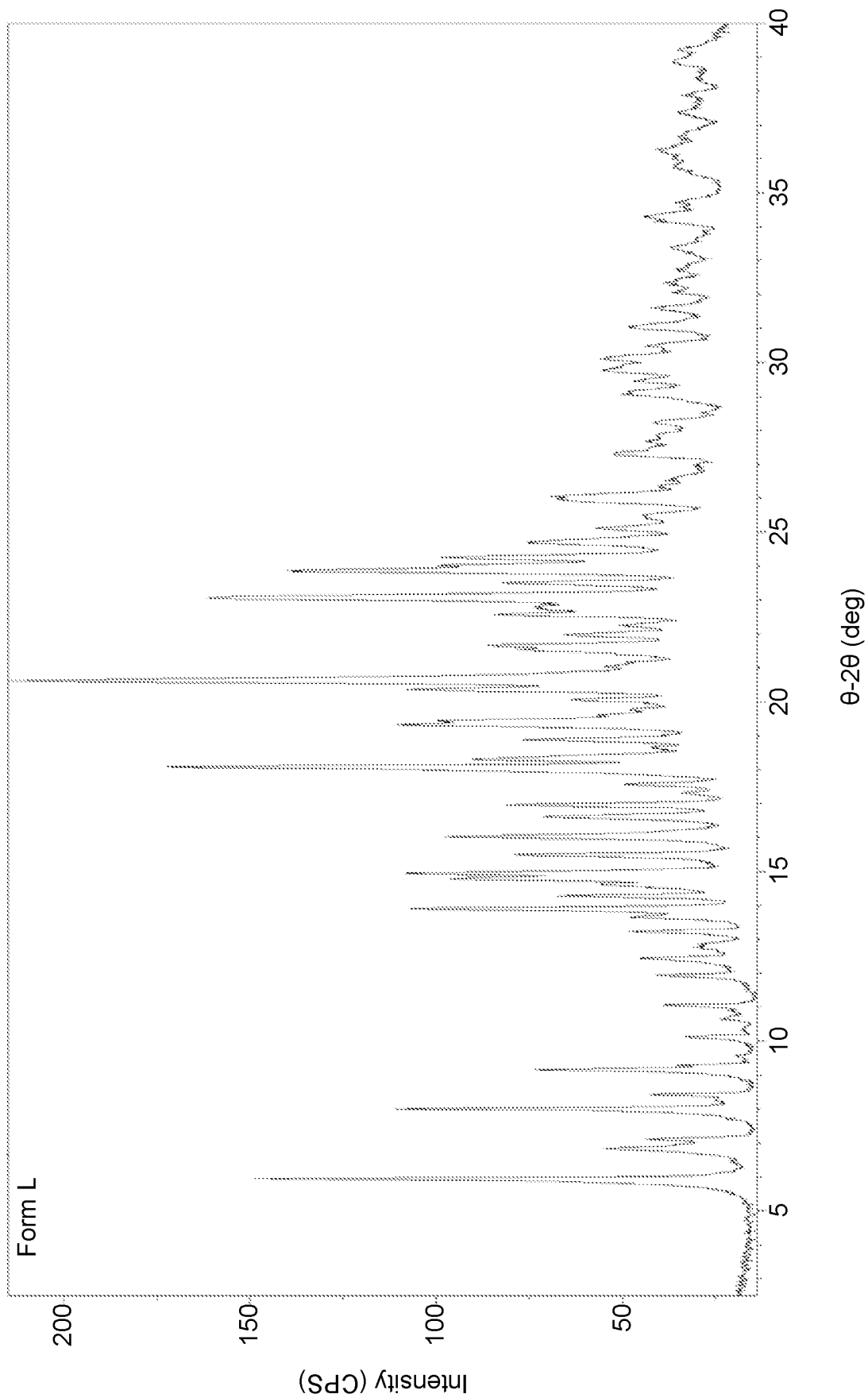
FIG. 26 is an XRPD corresponding to crystalline Form L.
Figure 29:
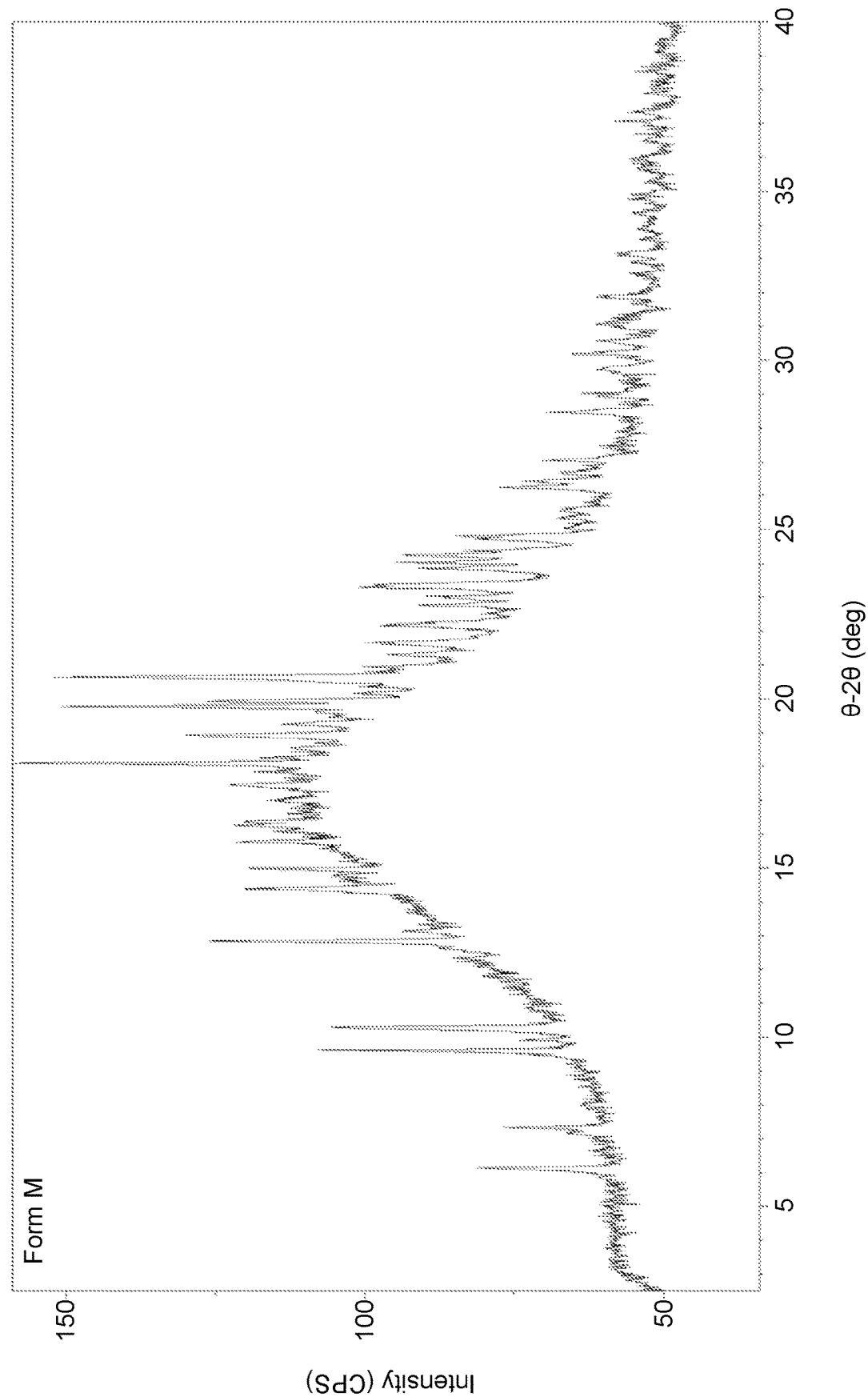
FIG. 29 is an XRPD corresponding to crystalline Form M.
Figure 30:
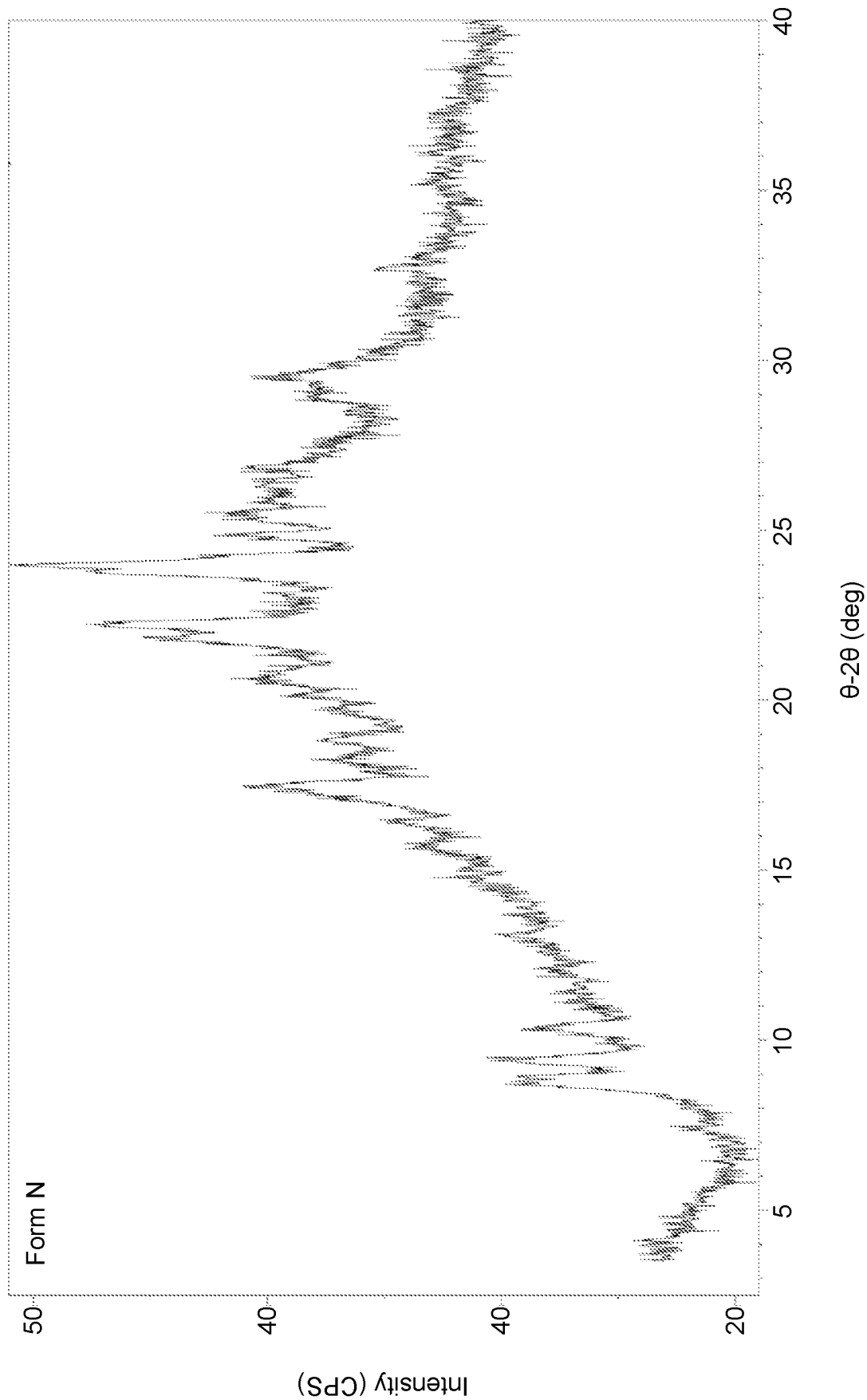
FIG. 30 is an XRPD corresponding to crystalline Form N.

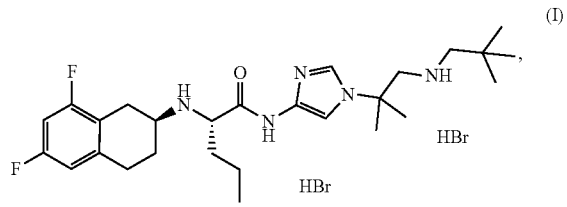 [SMILES: CCC[C@H](N[C@H]1CCc2cc(F)cc(F)c2C1)C(=O)Nc1cn(C(C)(C)CNCC(C)(C)C)cn1 ; Br ; Br]

selected from the group consisting of:
a) crystalline Form A, wherein Form A is characterized by an XRPD pattern having peaks at 8.8±0.2, 9.8±0.2, and 23.3±0.2 degrees two theta;
b) crystalline Form B, wherein Form B is characterized by an XRPD pattern substantially as shown in FIG. 4;
c) crystalline Form D, wherein Form D is characterized by an XRPD pattern substantially as shown in FIG. 11;
d) crystalline Form E, wherein Form E is characterized by an XRPD pattern substantially as shown in FIG. 14;
e) crystalline Form F, wherein Form F is characterized by an XRPD pattern substantially as shown in FIG. 17;
f) crystalline Form F', wherein Form F' is characterized by an XRPD pattern substantially as shown in FIG. 18;
g) crystalline Form G, wherein Form G is characterized by an XRPD pattern substantially as shown in FIG. 21;
h) crystalline Form H, wherein Form H is characterized by an XRPD pattern substantially as shown in FIG. 22;
i) crystalline Form H', wherein Form H' is characterized by an XRPD pattern substantially as shown in FIG. 23;
j) crystalline Form J, wherein Form J is characterized by an XRPD pattern substantially as shown in FIG. 24;
k) crystalline Form K, wherein Form K is characterized by an XRPD pattern substantially as shown in FIG. 25;
l) crystalline Form L, wherein Form L is characterized by an XRPD pattern substantially as shown in FIG. 26;
m) crystalline Form M, wherein Form M is characterized by an XRPD pattern substantially as shown in FIG. 29; and
n) crystalline Form N, wherein Form N is characterized by an XRPD pattern substantially as shown in FIG. 30.

The sections below discuss solid state forms that have been identified and selected properties of those solid state forms.

A. Crystalline Form A

In one aspect, the present disclosure relates to crystalline Form A of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

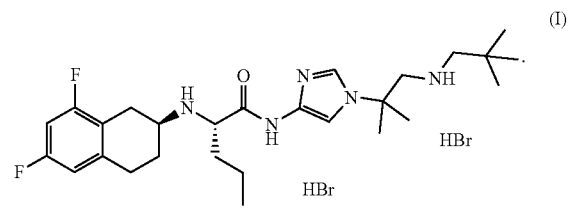 [SMILES: CCC[C@H](N[C@H]1CCc2cc(F)cc(F)c2C1)C(=O)Nc1cn(C(C)(C)CNCC(C)(C)C)cn1 ; Br ; Br]

In one embodiment, crystalline Form A is anhydrous.

In another embodiment, the melting point of crystalline Form A is about 254° C.

In another embodiment, Form A is characterized by an XRPD pattern having peaks at 8.8±0.2, 9.8±0.2, and 23.3±0.2 degrees two theta when measured by Cu Kα radiation. In another embodiment, Form A is characterized by an XRPD pattern having peaks at 8.8±0.2, 9.8±0.2, 23.3±0.2, 25.4±0.2, 28.0±0.2, and 29.3±0.2 degrees two theta when measured by Cu Kα radiation. In another embodiment, Form A is characterized by an XRPD pattern having peaks at 8.8±0.2, 9.8±0.2, 20.0±0.2, 23.3±0.2, 25.4±0.2, 28.0±0.2, 29.3±0.2, and 32.5±0.2 degrees two theta when measured by Cu Kα radiation.

Figure 2:
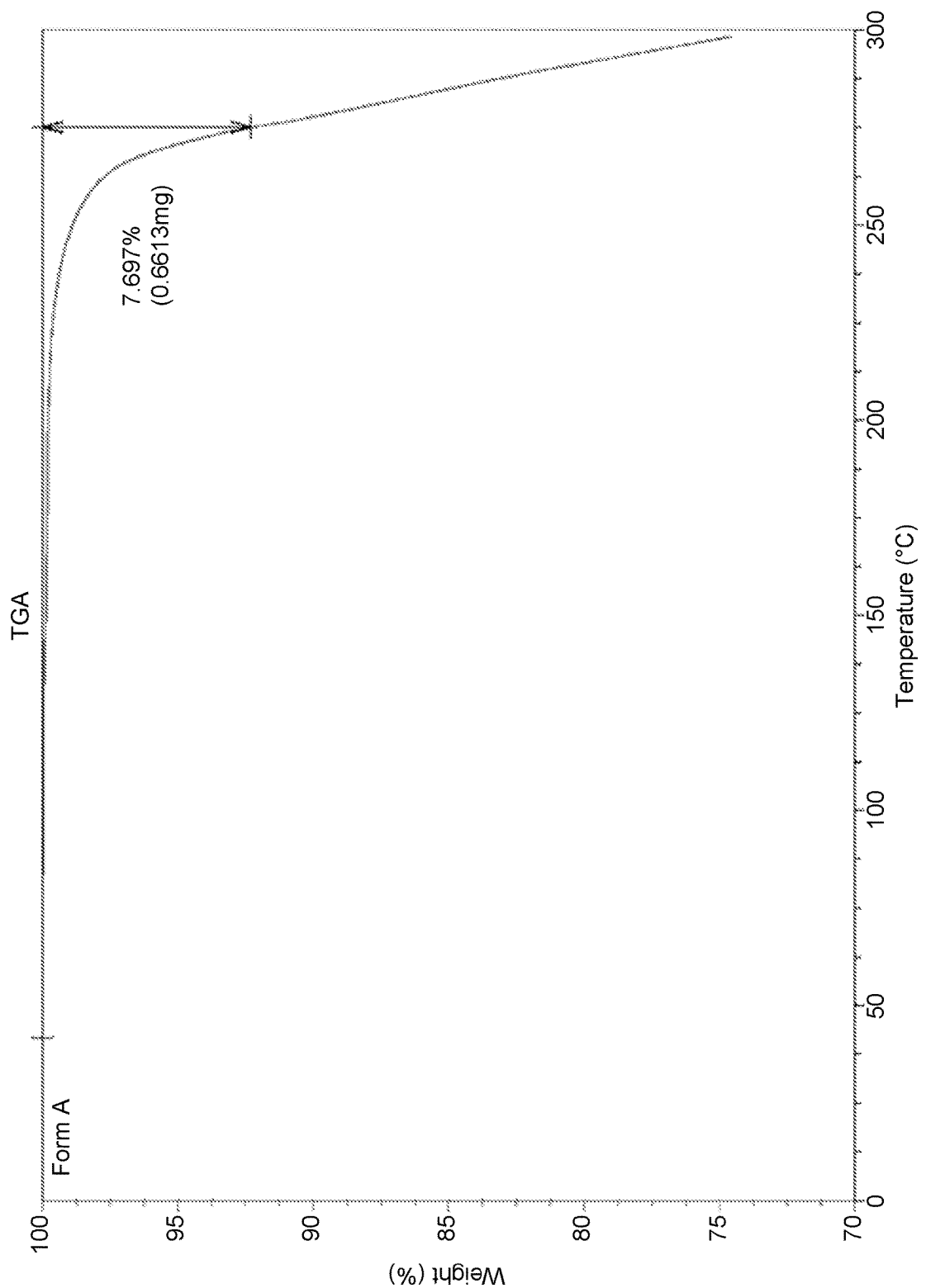
FIG. 2 is a thermogravimetric analysis thermogram ("TGA") corresponding to crystalline Form A.
Figure 3:
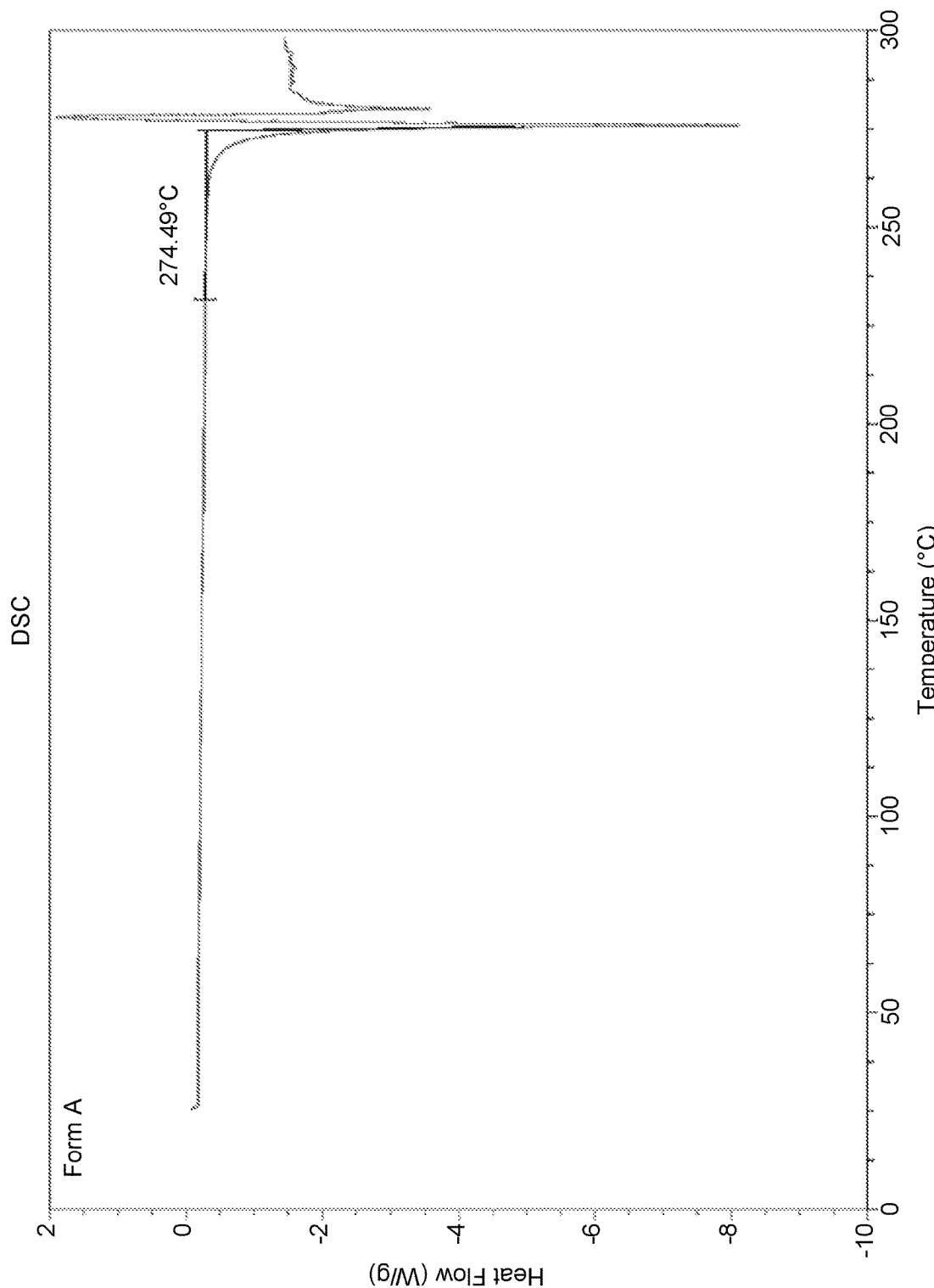
FIG. 3 is a differential scanning calorimetry thermogram ("DSC") corresponding to crystalline Form A.

In another embodiment, Form A is characterized by an XRPD pattern substantially as shown in FIG. 1. In another embodiment, Form A is characterized by a TGA profile substantially as shown in FIG. 2. In another embodiment, Form A is characterized by a DSC profile substantially as shown in FIG. 3.

In another embodiment, Form A has a unit cell that indexes as primitive monoclinic.

In another embodiment, Form A has a unit cell with an a value of about 10.035 Å, a b value of about 7.532 Å, and a c value of about 20.092 Å. In another embodiment, Form A has a unit cell with a volume of about 1518.1 Å$^3$.

The unit cell parameters for Form A are as follows:

| Bravais Type | Primitive Monoclinic |
|---|---|
| a [Å] | 10.035 |
| b [Å] | 7.532 |

-continued

| Bravais Type | Primitive Monoclinic |
|---|---|
| c [Å] | 20.092 |
| α [deg] | 90 |
| β [deg] | 91.39 |
| γ [deg] | 90 |
| Volume [Å³/cell] | 1518.1 |
| Chiral Contents? | Chiral |
| Extinction Symbol | P 1 2$_1$ 1 |
| Space Group(s) | P2$_1$ (4) |

In another embodiment, Form A is substantially free of other polymorphic forms. In another embodiment, Form A has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

B. Crystalline Form B

In one aspect, the present disclosure relates to crystalline Form B of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

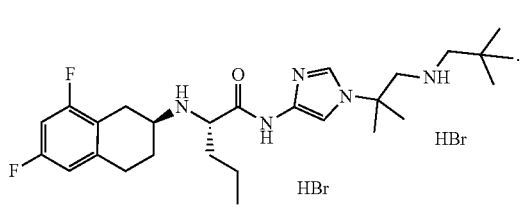

In one embodiment, Form B is characterized by an XRPD pattern substantially as shown in FIG. 4.

In another embodiment, Form B is substantially free of other polymorphic forms. In another embodiment, Form B has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

C. Crystalline Form C

In one aspect, the present disclosure relates to crystalline Form C of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (II),

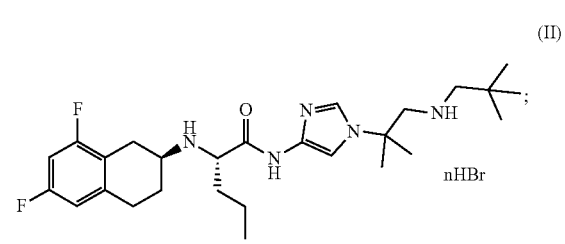

wherein n is about 1 to 3.

Figure 5:
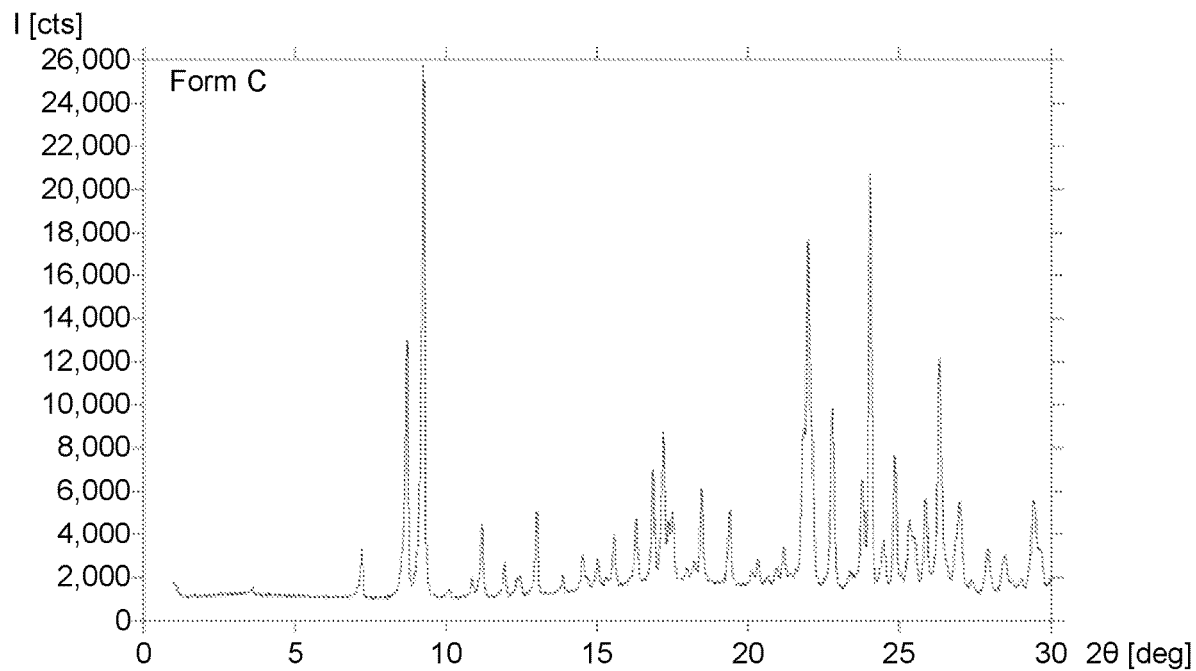
FIG. 5 is an XRPD corresponding to crystalline Form C.
Figure 6:
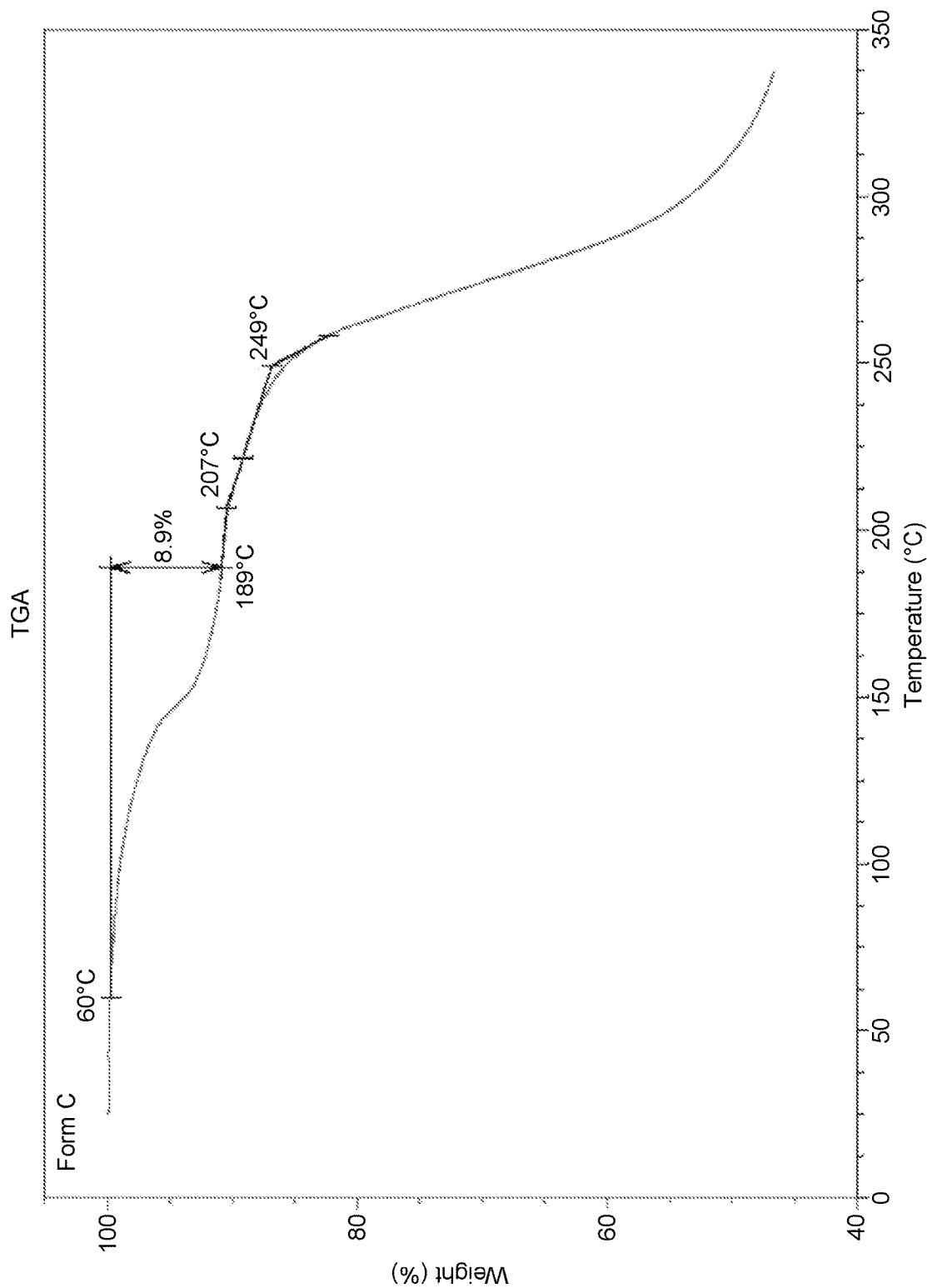
FIG. 6 is a TGA corresponding to crystalline Form C.
Figure 7:
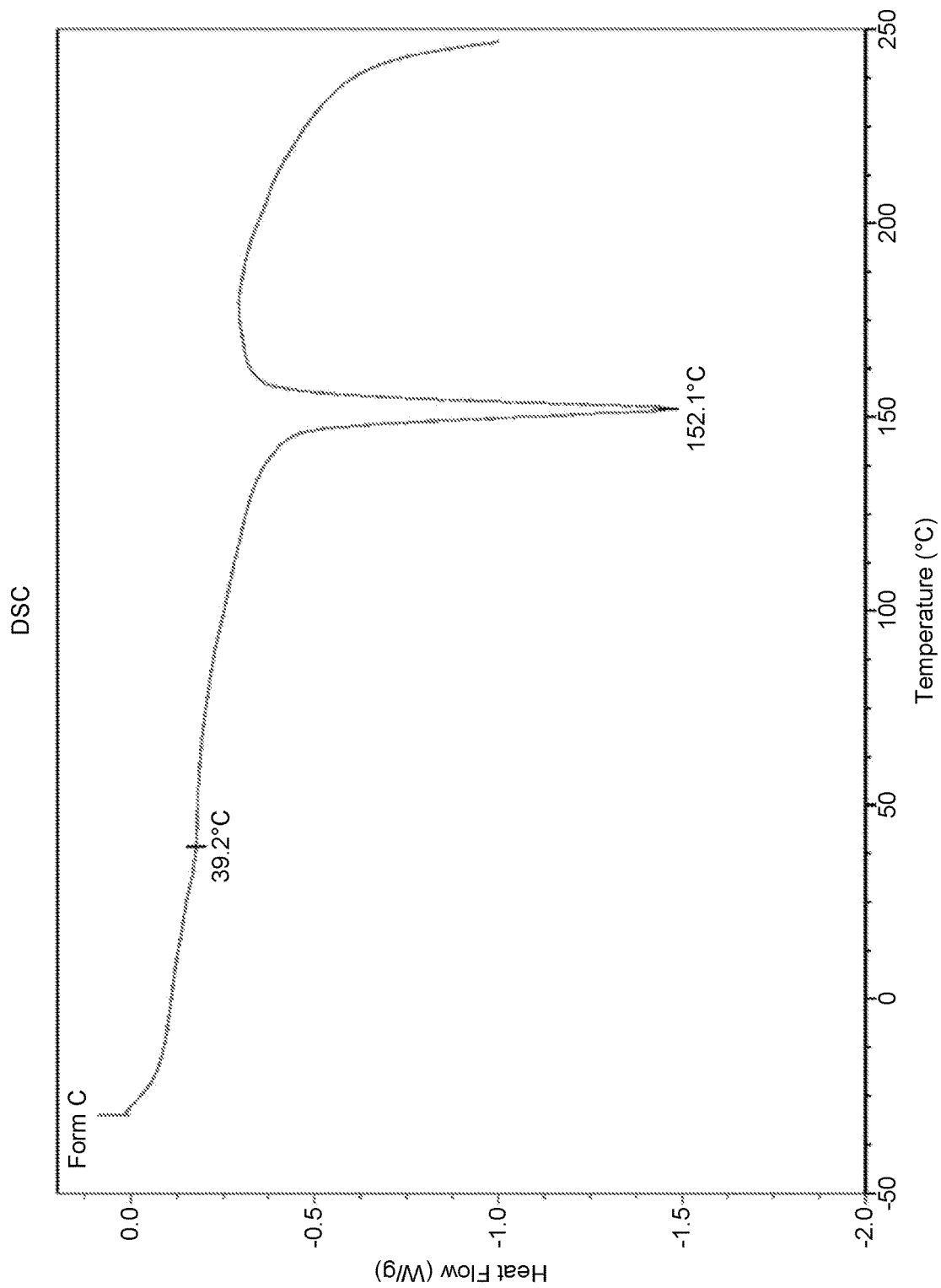
FIG. 7 is a DSC corresponding to crystalline Form C.
Figure 8:
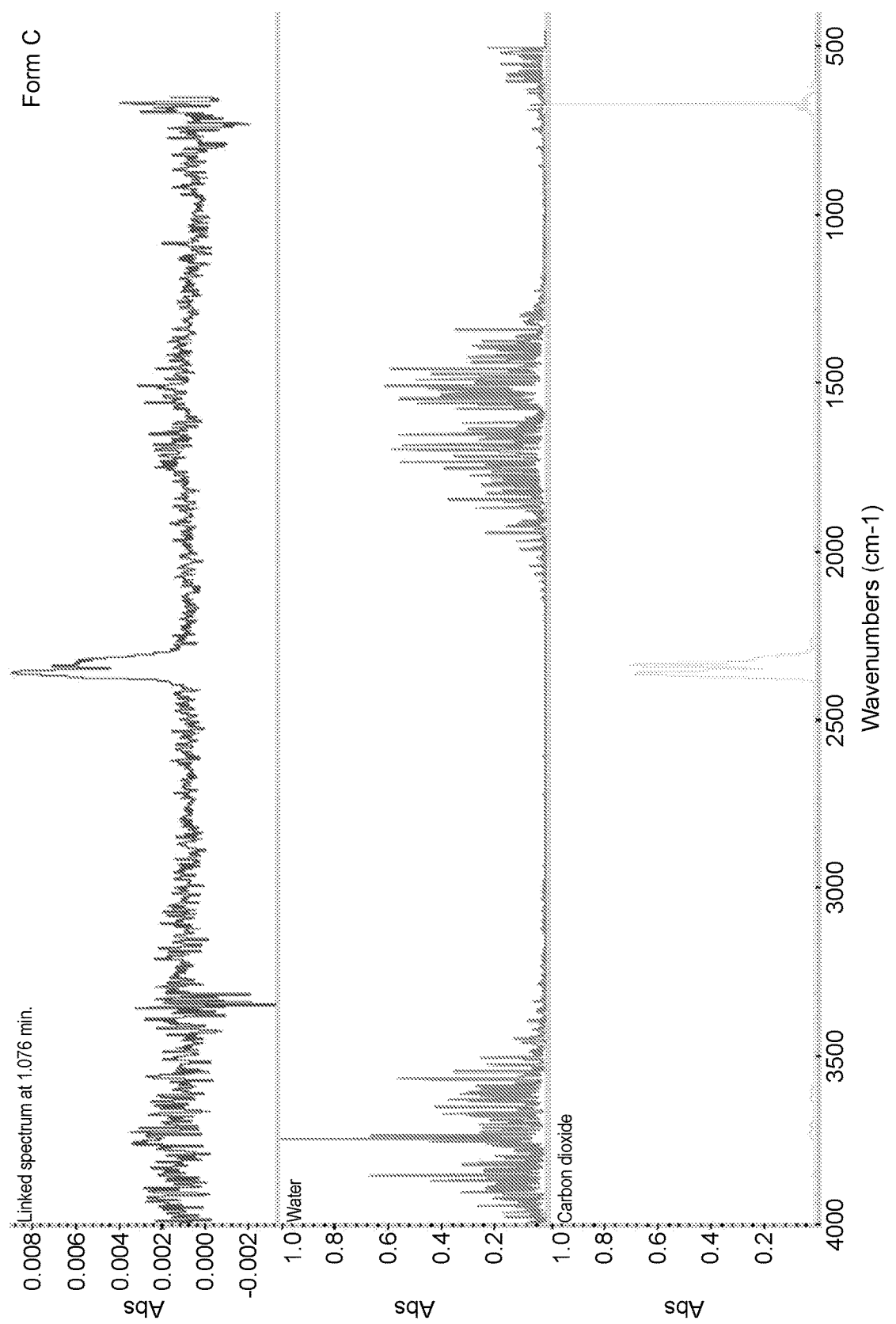
FIGS. 8-10 are thermogravimetric infrared analyses ("TG-IR") corresponding to crystalline Form C.
Figure 9:
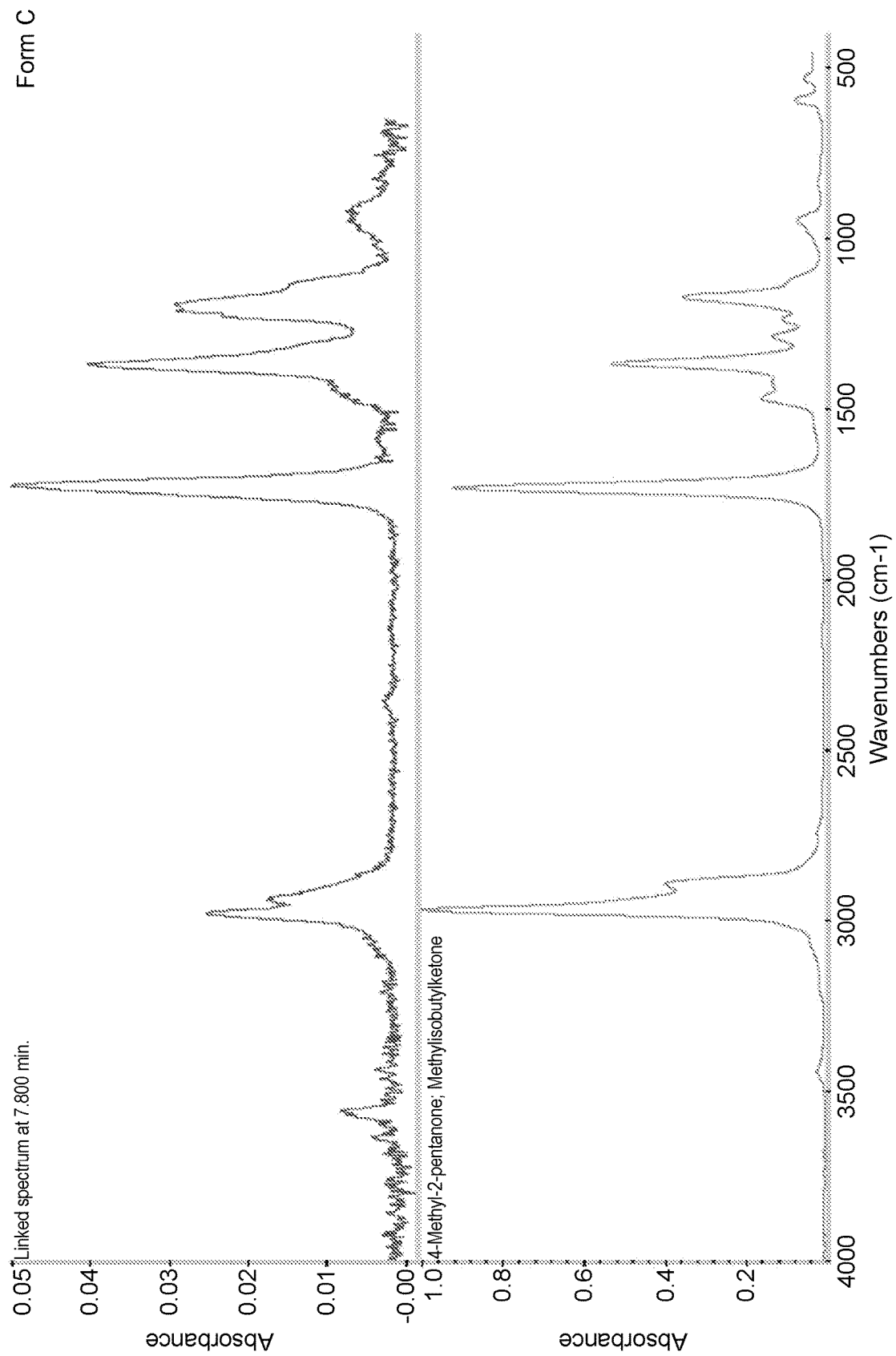
Figure 10:
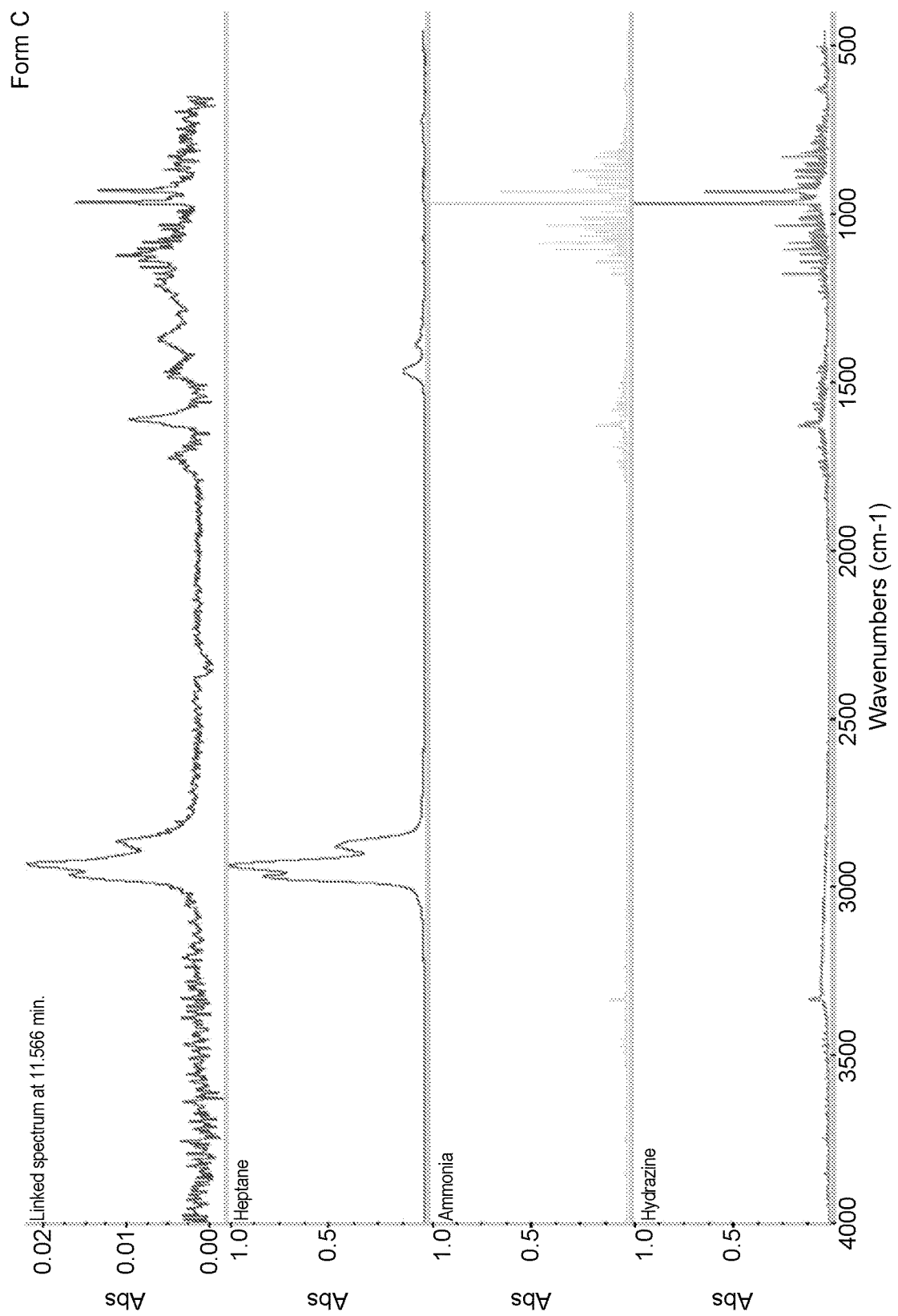

In one embodiment, Form C has one or more characteristics selected from the group consisting of a)-d):
a) an XRPD pattern substantially as shown in FIG. 5;
b) a TGA profile substantially as shown in FIG. 6;
c) a DSC profile substantially as shown in FIG. 7; and
d) a TG-IR linked spectrum substantially as shown in a figure selected from a group consisting of FIGS. 8 to 10.

In another embodiment, Form C has a unit cell that indexes as primitive orthorhombic.

In another embodiment, Form C has a unit cell with an a value of about 7.491 Å, a b value of about 10.353 Å, and a c value of about 48.790 Å. In another embodiment, Form C has a unit cell with a volume of about 3783.9 Å³.

The unit cell parameters for Form C are as follows:

| Bravais Type | Primitive Orthorhombic |
|---|---|
| a [Å] | 7.491 |
| b [Å] | 10.353 |
| c [Å] | 48.790 |
| α [deg] | 90 |
| β [deg] | 90 |
| γ [deg] | 90 |
| Volume [Å³/cell] | 3783.9 |
| Chiral Contents? | Chiral |
| Extinction Symbol | P 2$_1$ 2$_1$ 2$_1$ |
| Space Group(s) | P2$_1$2$_1$2$_1$ (19) |

In another embodiment, the TGA exhibits that Form C loses at least 8 wt % between about 60° C. and about 190° C. In another embodiment, Form C exhibits a DSC thermogram that has a first endothermic event at about 39° C. and a second endothermic event at about 152° C.

In another embodiment, Form C is substantially free of other polymorphic forms. In another embodiment, Form C has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

D. Crystalline Form D

In one aspect, the present disclosure relates to crystalline Form D of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

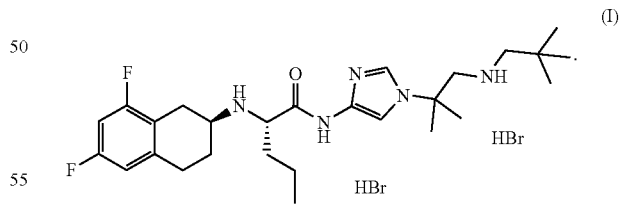

Figure 12A:
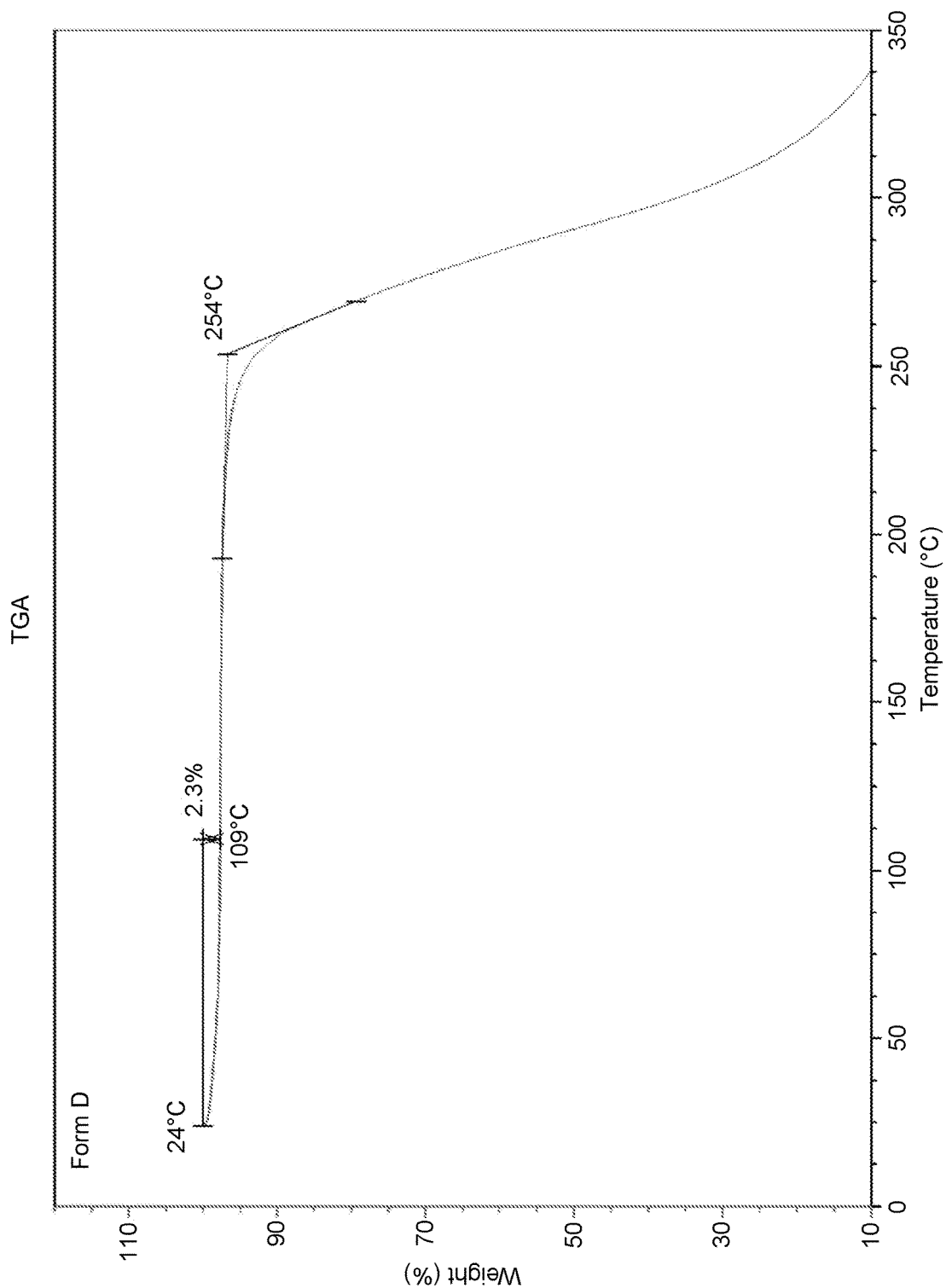
FIG. 12A is a TGA corresponding to crystalline Form D as prepared.
Figure 12B:
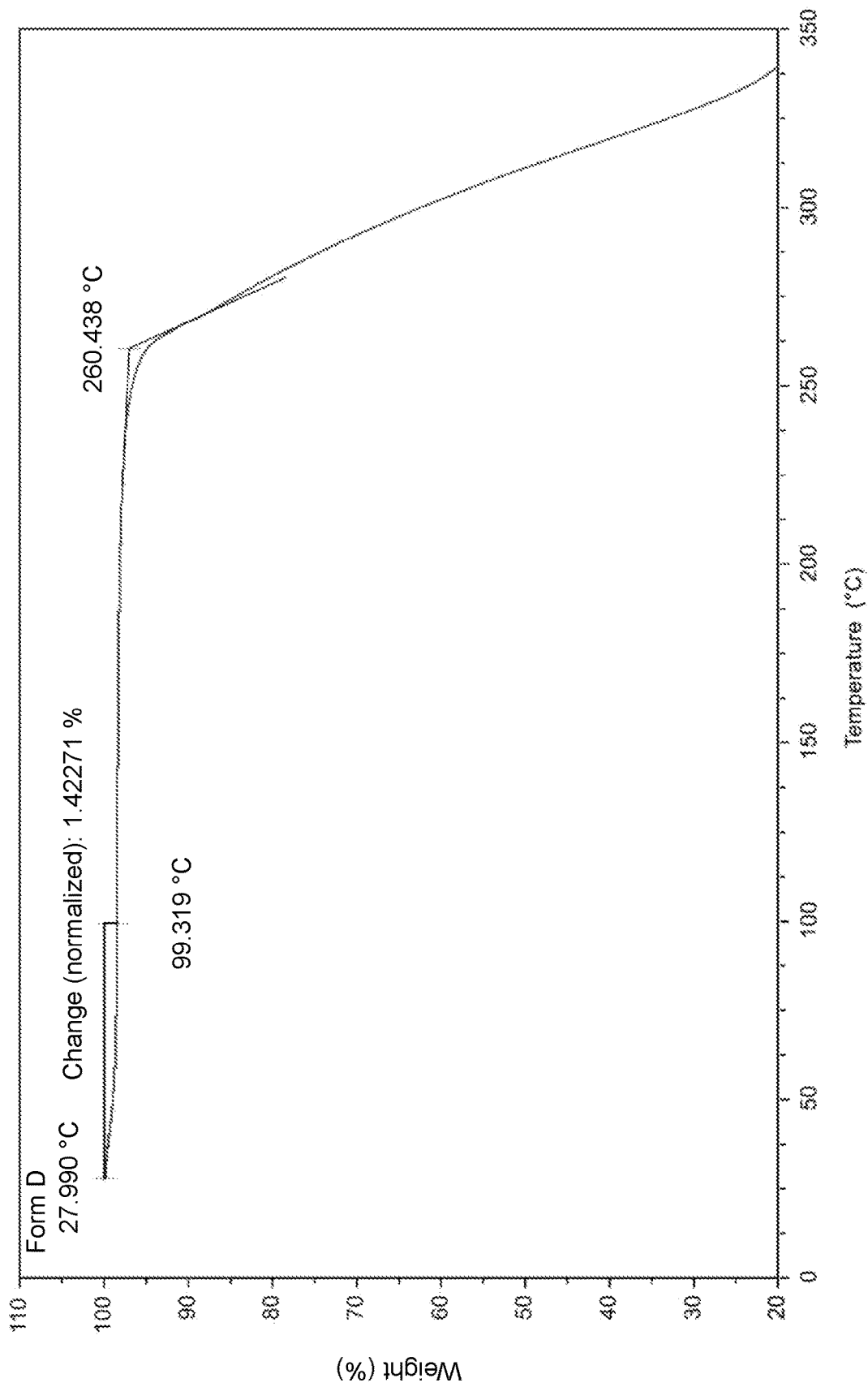
FIG. 12B is a TGA corresponding to crystalline Form D when vacuum dried at 75° C.
Figure 13:
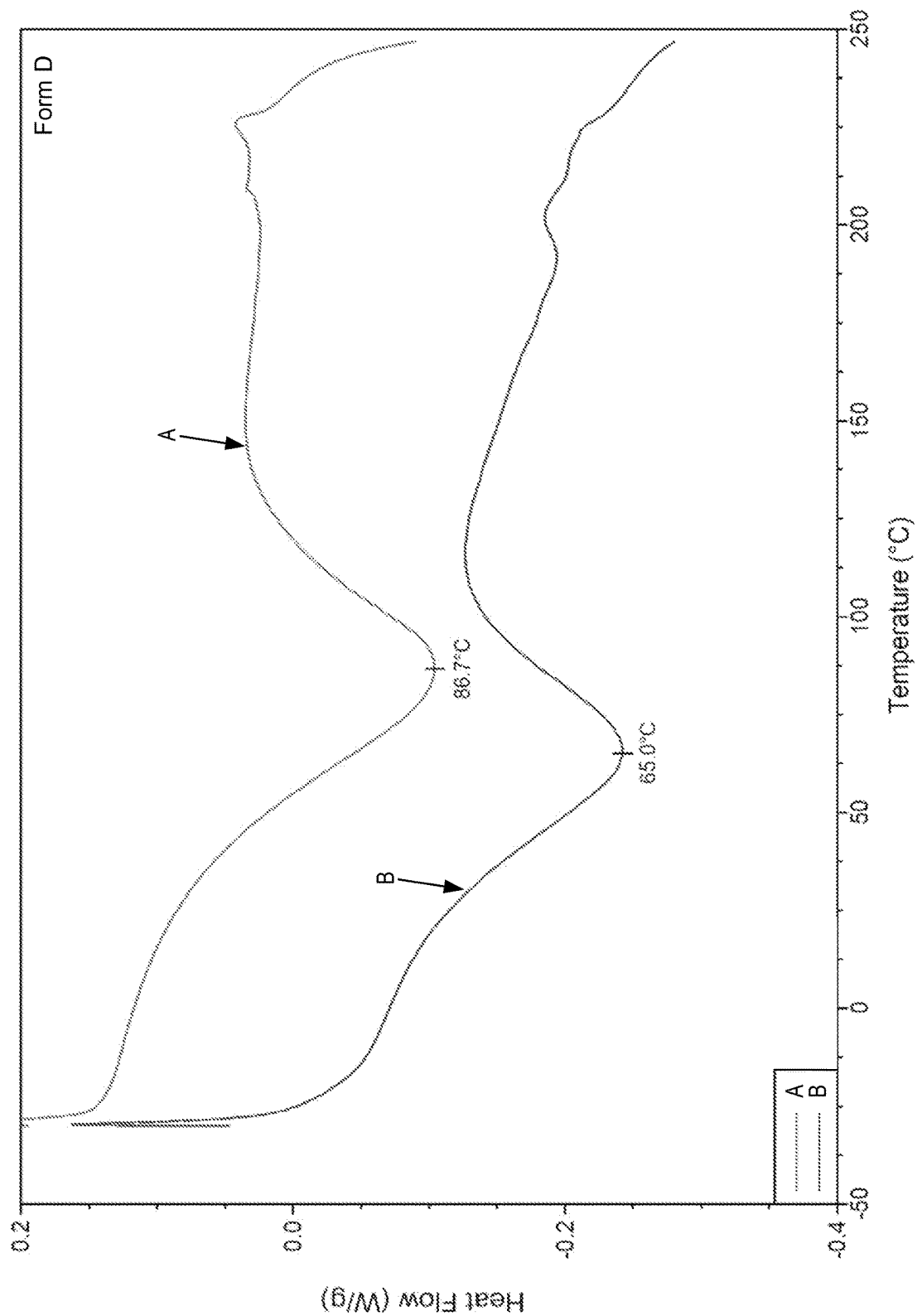
FIG. 13 is a DSC corresponding to crystalline Form D. Line A is the DSC of Form D as prepared. Line B is the DSC of Form D when vacuum dried at 75° C.

In one embodiment, Form D has one or more characteristics selected from the group consisting of a)-c):
a) an XRPD pattern substantially as shown in FIG. 11;
b) a TGA profile substantially as shown in FIG. 12A or FIG. 12B; and
c) a DSC profile substantially as shown in Line A or Line B of FIG. 13.

In another embodiment, Form D has a unit cell that indexes as primitive monoclinic. In another embodiment, Form D has a unit cell with an a value of about 18.465 Å, a b value of about 7.441 Å, and a c value of about 23.885 Å. In another embodiment, Form D has a unit cell with a volume of about 3250.4 Å³.

The unit cell parameters for Form D are as follows:

| Bravais Type | Primitive Monoclinic |
|---|---|
| a [Å] | 18.465 |
| b [Å] | 7.441 |
| c [Å] | 23.885 |
| α [deg] | 90 |
| β [deg] | 97.95 |
| γ [deg] | 90 |
| Volume [Å³/cell] | 3250.4 |
| Chiral Contents? | Chiral |
| Extinction Symbol | P 1 2₁ 1 |
| Space Group(s) | P2₁ (4) |

In another embodiment, the TGA exhibits that Form D loses about 1.2 to about 2.5 wt % between about 24° C. and about 109° C.

In another embodiment, Form D exhibits a DSC thermogram that has an endothermic event at about 65° C.

In another embodiment, Form D is substantially free of other polymorphic forms. In another embodiment, Form D has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

E. Crystalline Form E

In one aspect, the present disclosure relates to crystalline Form E of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

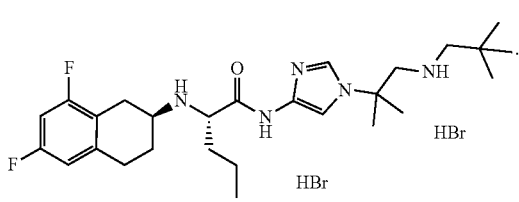

(I)

Figure 15:
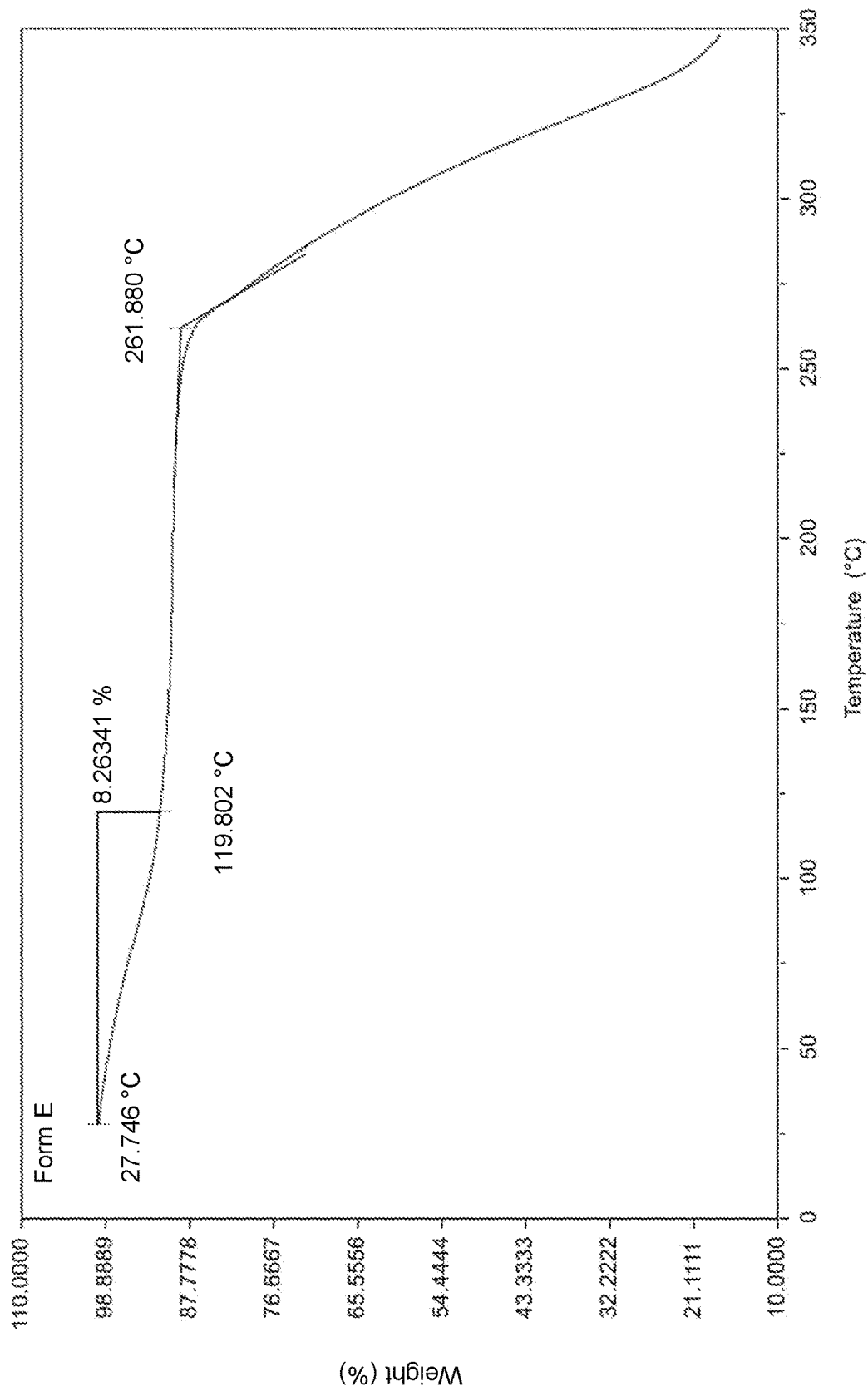
FIG. 15 is a TGA corresponding to crystalline Form E.
Figure 16:
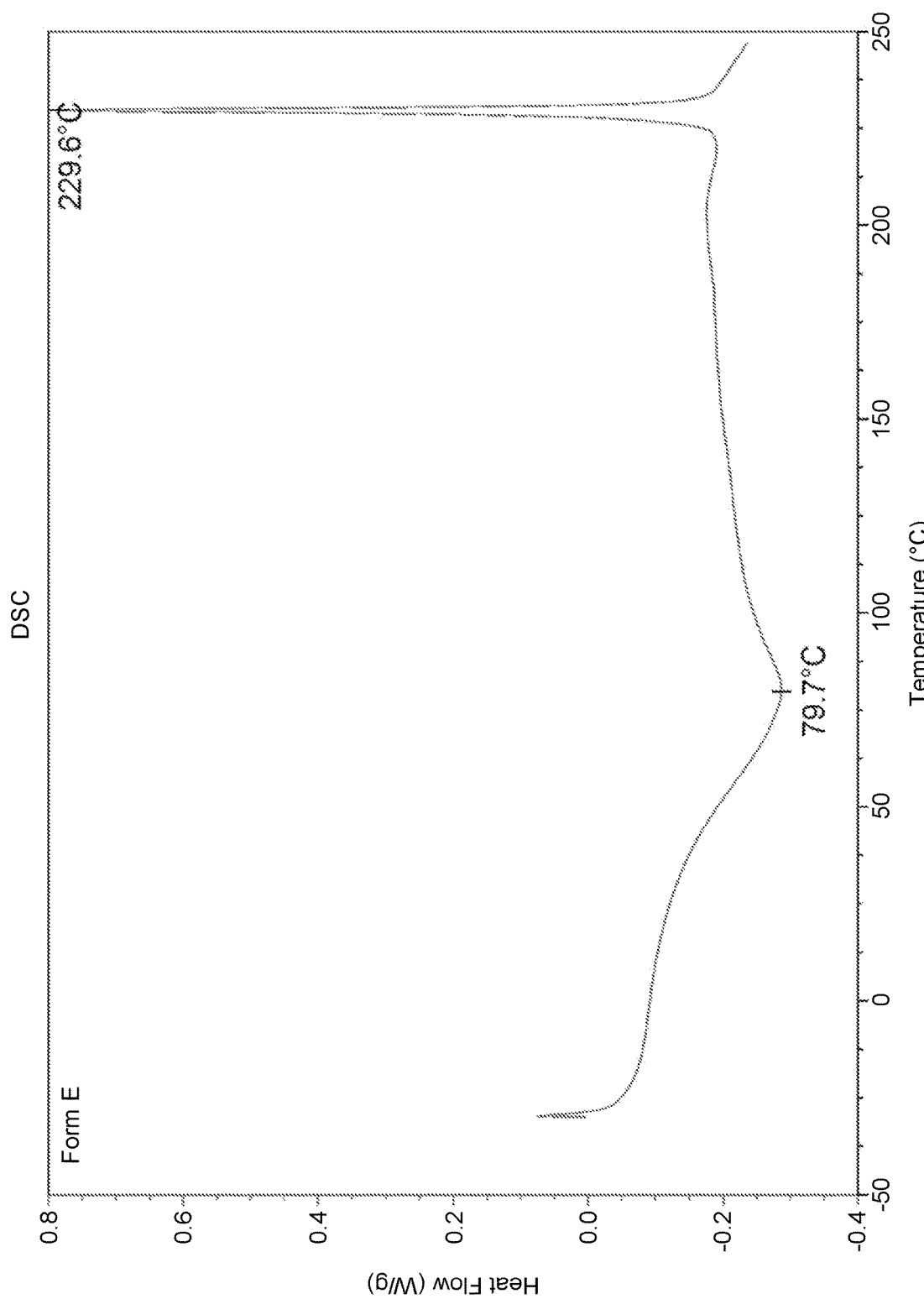
FIG. 16 is a DSC corresponding to crystalline Form E.

In one embodiment, Form E has one or more characteristics selected from the group consisting of a)-c):
a) an XRPD pattern substantially as shown in FIG. 14;
b) a TGA profile substantially as shown in FIG. 15; and
c) a DSC profile substantially as shown in FIG. 16.

In another embodiment, the TGA exhibits that Form E loses about 8 wt % between about 28° C. and about 120° C.

In another embodiment, Form E exhibits a DSC thermogram that has an endothermic event at about 80° C.

In another embodiment, Form E is substantially free of other polymorphic forms. In another embodiment, Form E has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

F. Crystalline Form F

In one aspect, the present disclosure relates to crystalline Form F of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

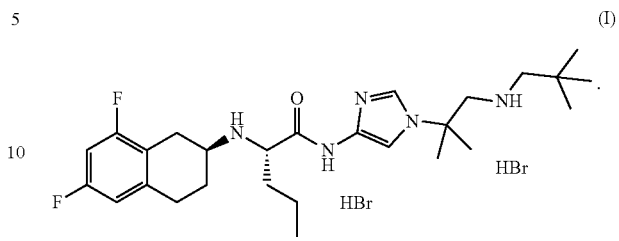

(I)

In another embodiment, Form F is characterized by an XRPD pattern substantially as shown in FIG. 17.

In another embodiment, Form A is substantially free of other polymorphic forms. In another embodiment, Form A has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

G. Crystalline Form F'

In one aspect, the present disclosure relates to crystalline Form F' of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

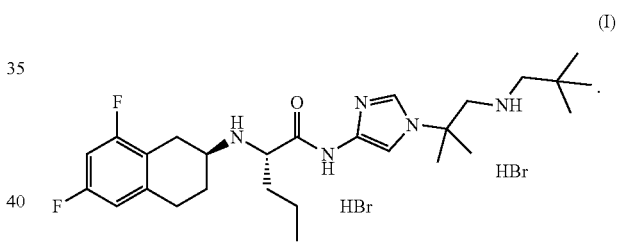

(I)

Figure 19:
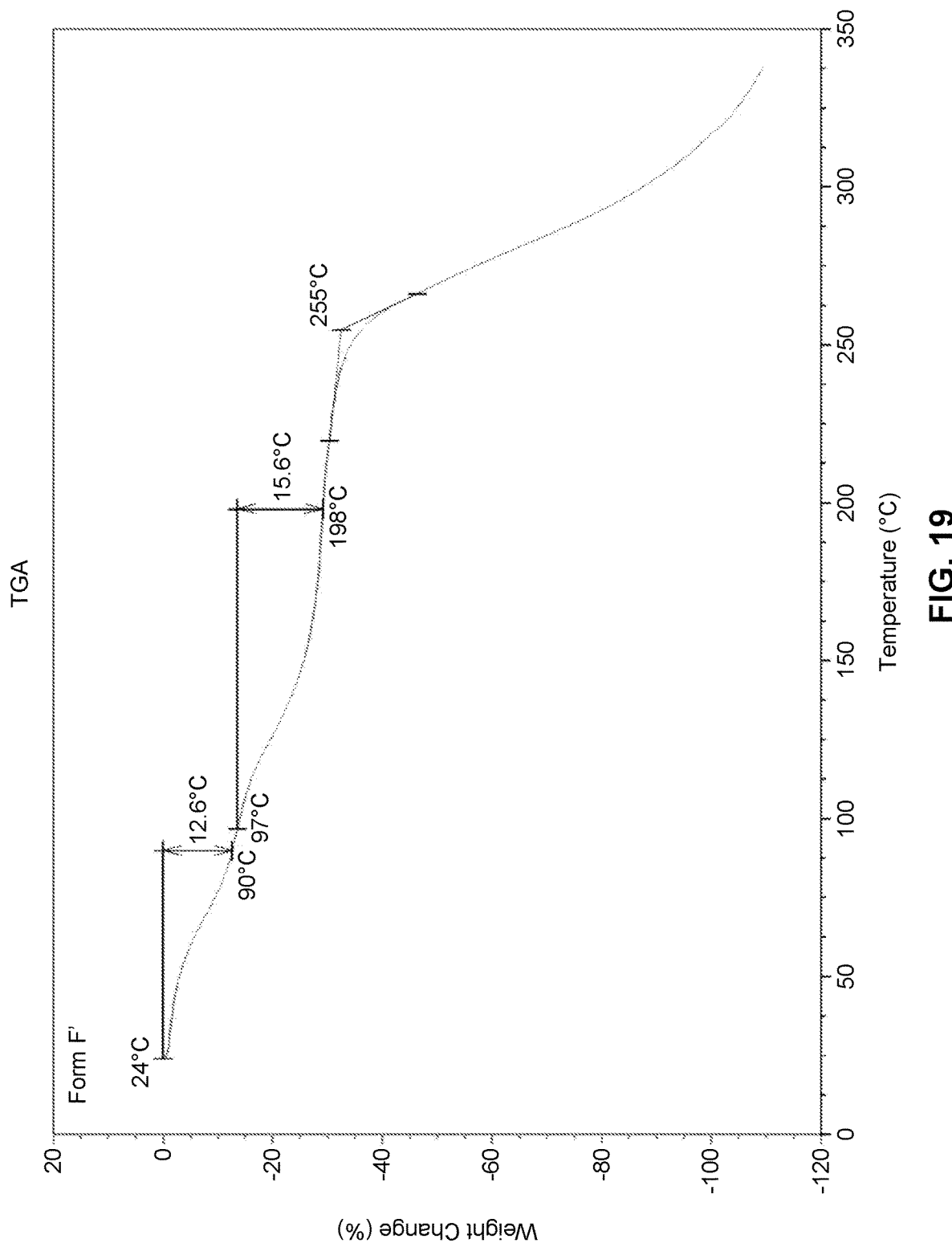
FIG. 19 is a TGA corresponding to crystalline Form F'.
Figure 20:
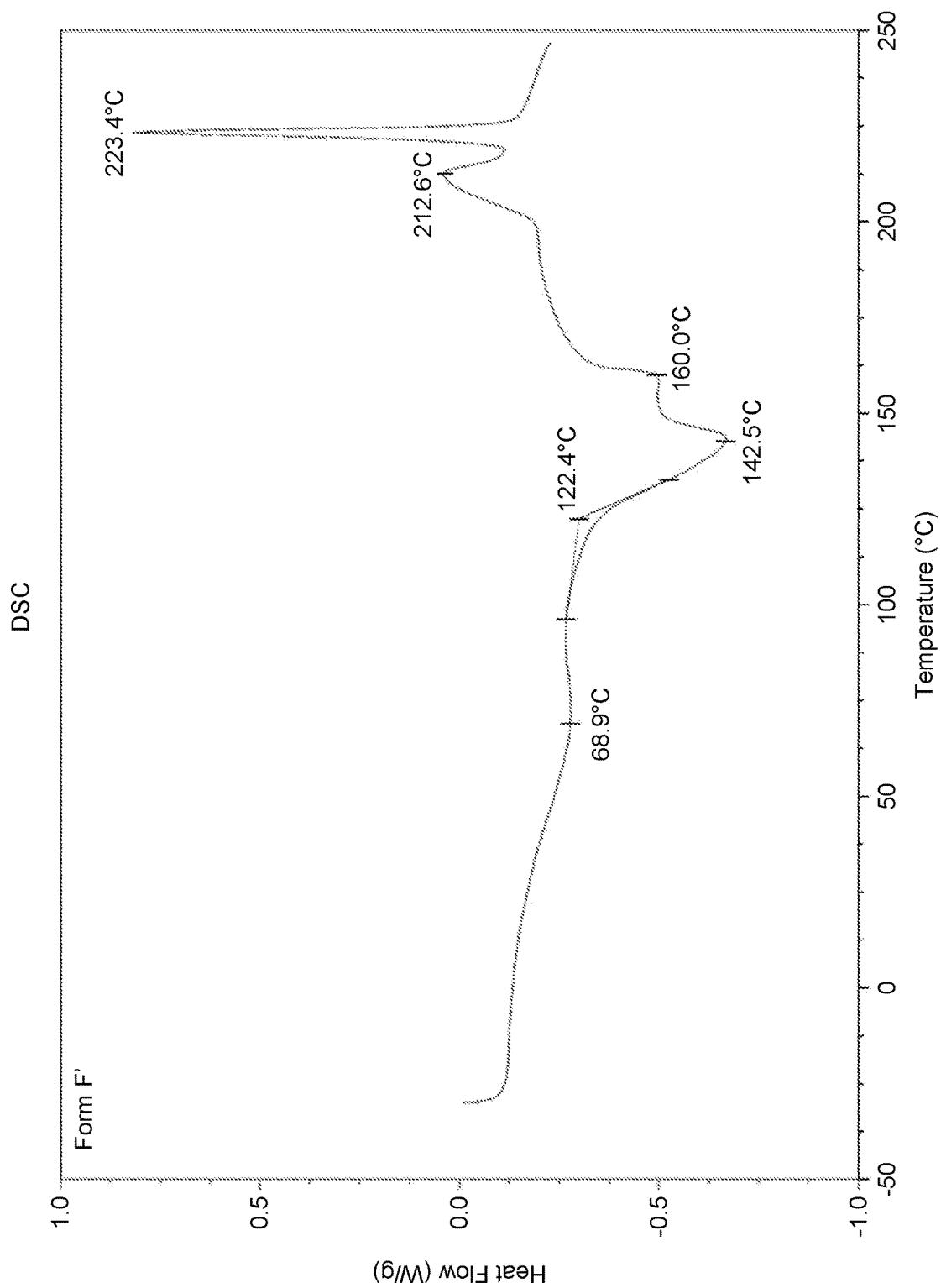
FIG. 20 is a DSC corresponding to crystalline Form F'.

In one embodiment, Form F' has one or more characteristics selected from the group consisting of a)-c):
a) an XRPD pattern substantially as shown in FIG. 18;
b) a TGA profile substantially as shown in FIG. 19; and
c) a DSC profile substantially as shown in FIG. 20.

In another embodiment, the TGA exhibits that Form F' loses about 12.6 wt % between about 24° C. and about 90° C. and loses about 15.6 wt % between about 97° C. to about 198° C.

In another embodiment, Form A is substantially free of other polymorphic forms. In another embodiment, Form A has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

H. Crystalline Form G

In one aspect, the present disclosure relates to crystalline Form G of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

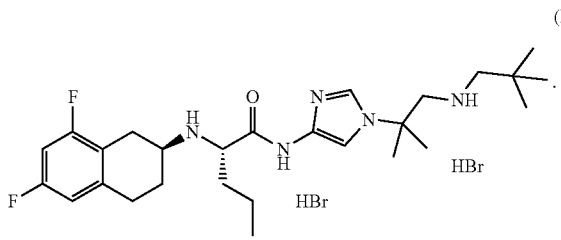

In one embodiment, Form G is characterized by an XRPD pattern substantially as shown in FIG. 21.

In another embodiment, Form G is substantially free of other polymorphic forms. In another embodiment, Form G has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

I. Crystalline Form H

In one aspect, the present disclosure relates to crystalline Form H of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I)

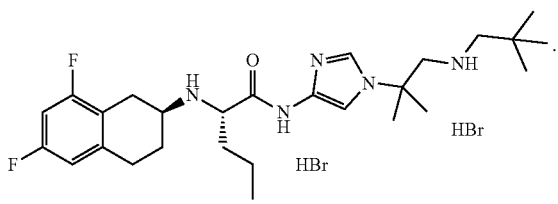

In one embodiment, Form H is characterized by an XRPD pattern substantially as shown in FIG. 22.

In another embodiment, Form H is substantially free of other polymorphic forms. In another embodiment, Form H has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

J. Crystalline Form H'

In one aspect, the present disclosure relates to crystalline Form H' of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I)

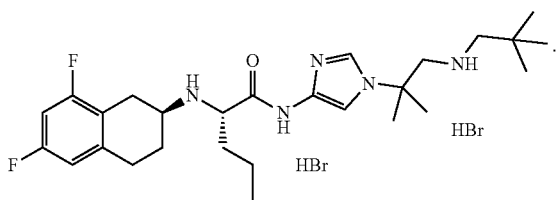

In one embodiment, Form H' is characterized by an XRPD pattern substantially as shown in FIG. 23.

In another embodiment, Form H' is substantially free of other polymorphic forms. In another embodiment, Form H' has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

K. Crystalline Form J

In one aspect, the present disclosure relates to crystalline Form J of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

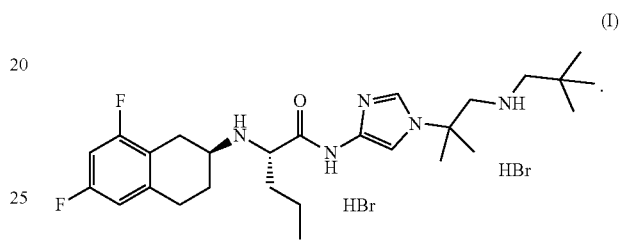

In one embodiment, Form J is characterized by an XRPD pattern substantially as shown in FIG. 24.

In another embodiment, Form J is substantially free of other polymorphic forms. In another embodiment, Form J has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

L. Crystalline Form K

In one aspect, the present disclosure relates to crystalline Form K of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

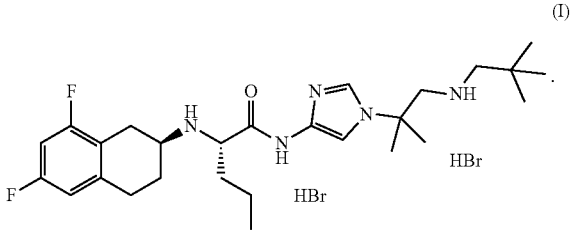 [SMILES: CCC[C@H](N[C@H]1CCc2cc(F)cc(F)c2C1)C(=O)Nc1cn(C(C)(C)CNCC(C)(C)C)cn1 ; Br ; Br]

In one embodiment, Form K is characterized by an XRPD pattern substantially as shown in FIG. 25.

In another embodiment, Form K is substantially free of other polymorphic forms. In another embodiment, Form K has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

M. Crystalline Form L

In one aspect, the present disclosure relates to crystalline Form L of a hydrobromide salt of (S)-2-(((S)-6,8-difluoro- 1,2,3,4-tetrahydronaphthalen-2-yl)amino)-N-(1-(2-methyl-1-(neopentylamino) propan-2-yl)-1H-imidazol-4-yl)pentanamide having Formula (I),

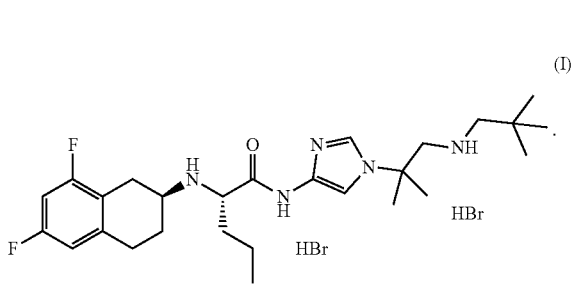 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

Figure 27:
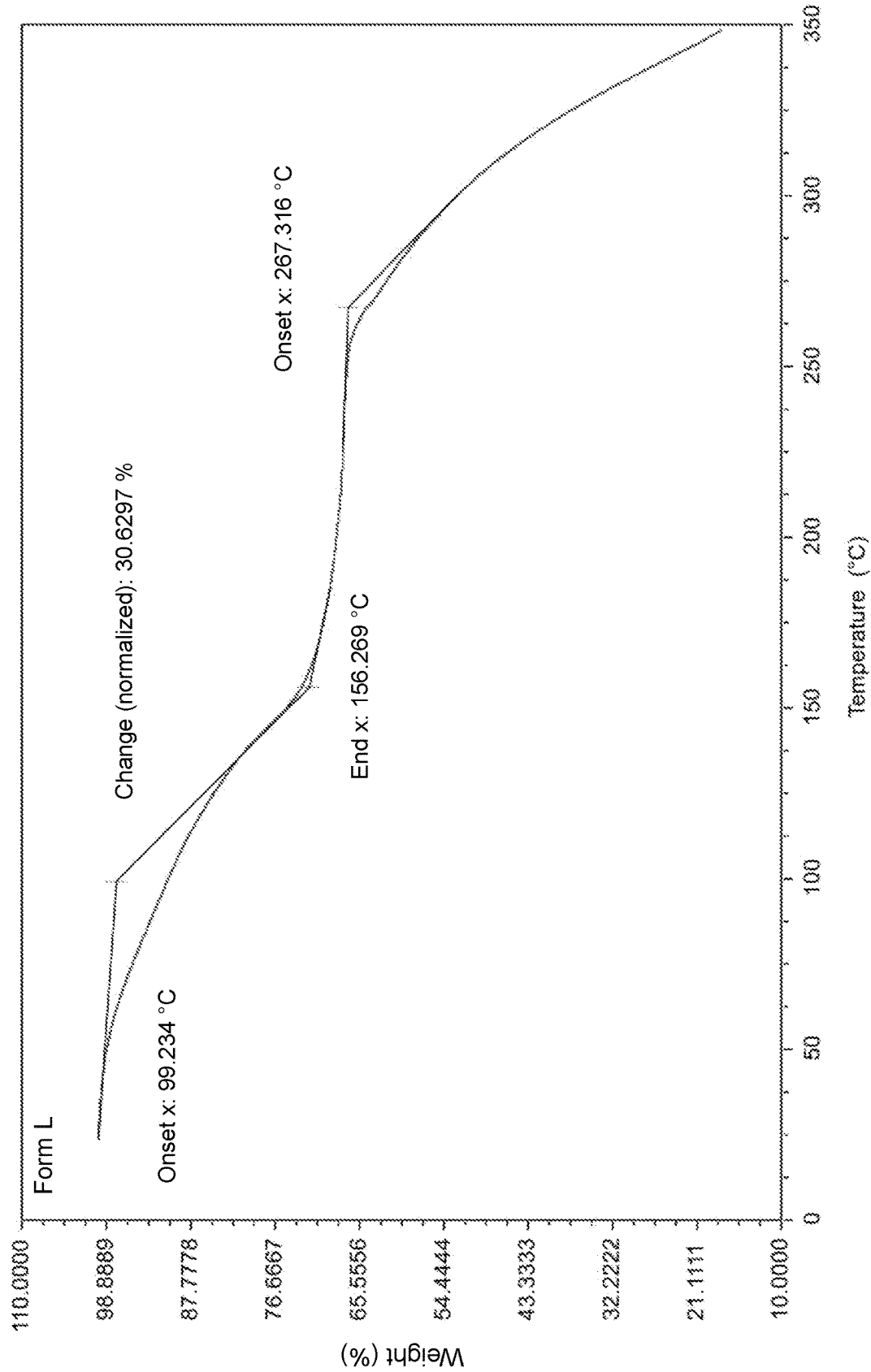
FIG. 27 is a TGA corresponding to crystalline Form L.
Figure 28:
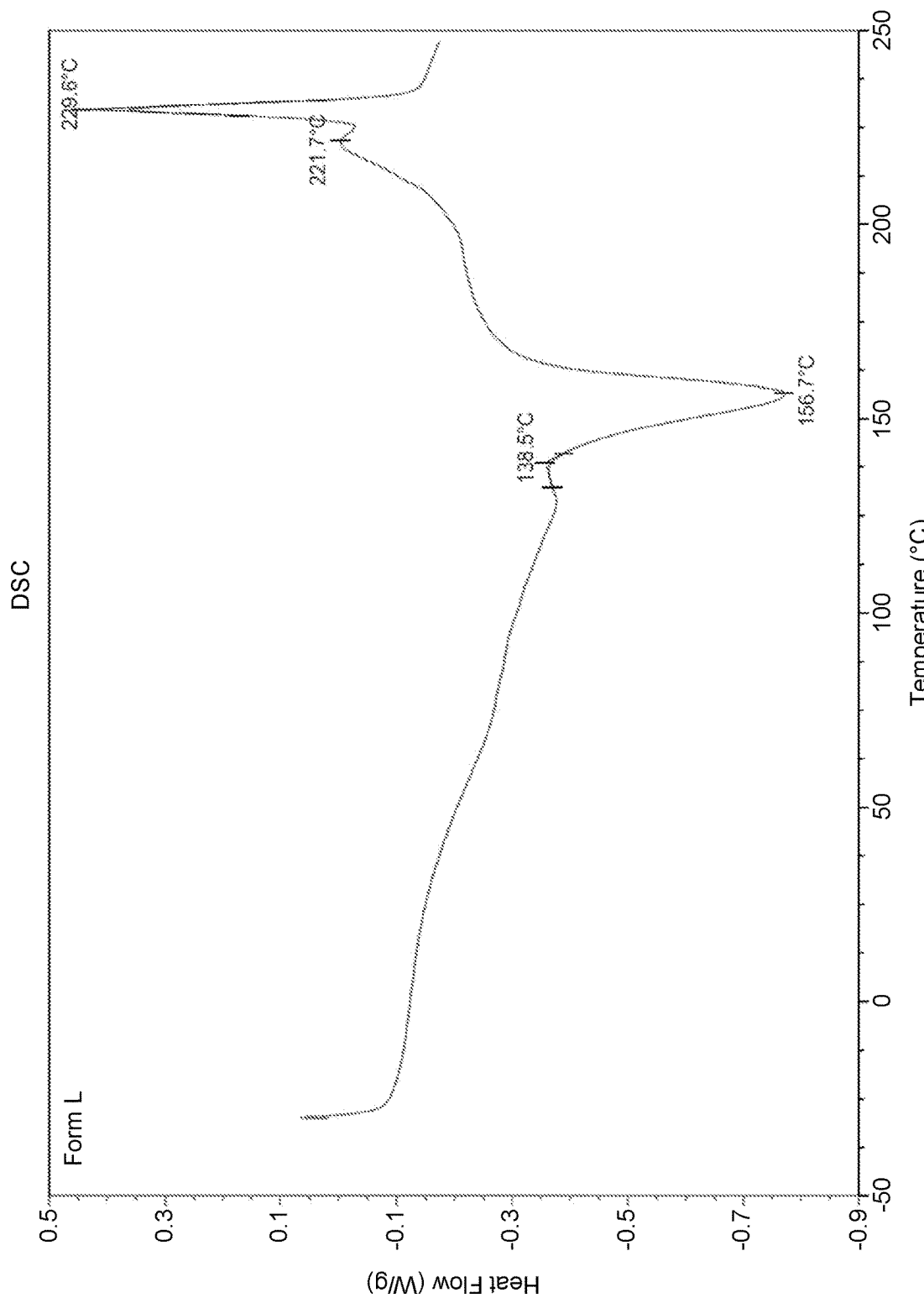
FIG. 28 is a DSC corresponding to crystalline Form L.

In one embodiment, Form L has one or more characteristics selected from the group consisting of a)-c):

a) an XRPD pattern substantially as shown in FIG. 26;

b) a TGA profile substantially as shown in FIG. 27; and c) a DSC profile substantially as shown in FIG. 28.

In another embodiment, Form L exhibits a DSC thermogram that has an endothermic event at about 157° C.

In another embodiment, Form L is substantially free of other polymorphic forms. In another embodiment, Form L has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

N. Crystalline Form M

In one aspect, the present disclosure relates to crystalline Form M of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I),

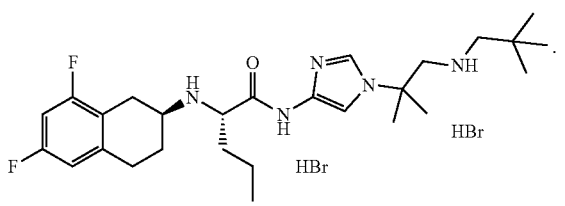

(I)

In one embodiment, Form M is characterized by an XRPD pattern substantially as shown in FIG. 29.

In another embodiment, Form M is substantially free of other polymorphic forms. In another embodiment, Form M has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

O. Crystalline Form N

In one aspect, the present disclosure relates to crystalline Form N of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having Formula (I),

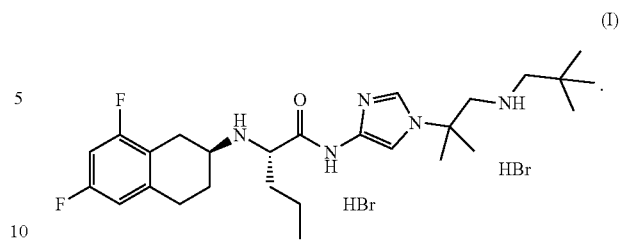

(I)

In one embodiment, Form N is characterized by an XRPD pattern substantially as shown in FIG. 30.

In another embodiment, Form N is substantially free of other polymorphic forms. In another embodiment, Form N has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

P. Amorphous

In one aspect, the present disclosure relates to amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I),

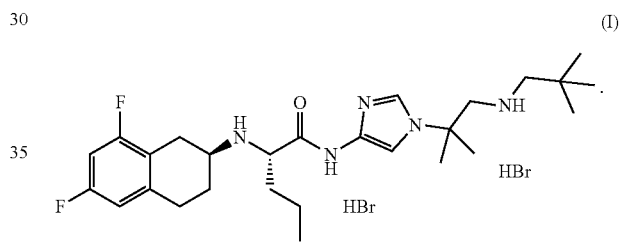

(I)

Figure 31:
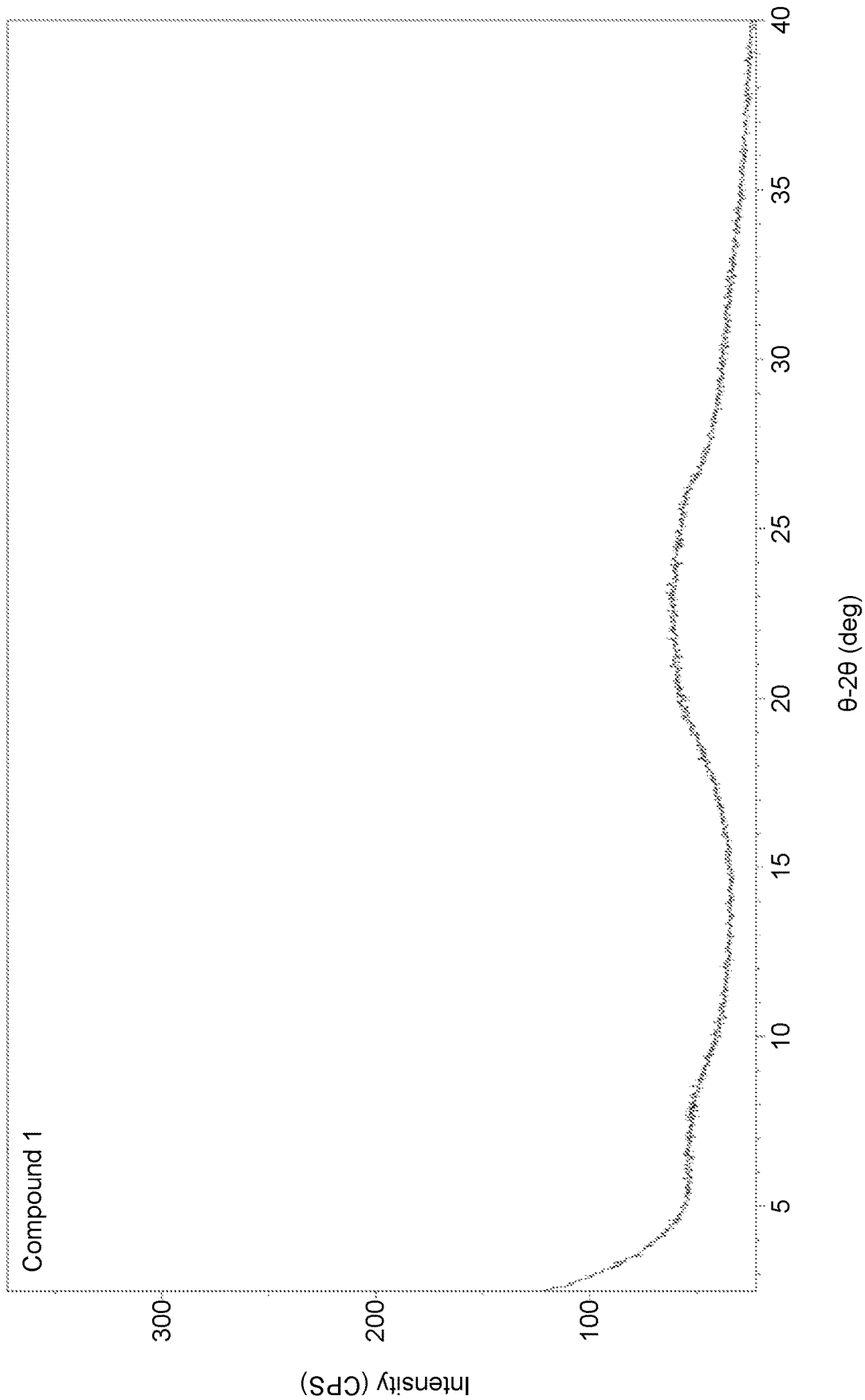
FIG. 31 is an XRPD corresponding to amorphous Compound 1 of Formula (I).

In one embodiment, the amorphous Compound 1 of Formula (I) is characterized by an XRPD pattern substantially as shown in FIG. 31.

In another embodiment, the amorphous Compound 1 of Formula (I) is substantially free of polymorphic forms. In another embodiment, the amorphous Compound 1 of Formula (I) has a polymorphic purity of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

III. Particle Size

In another aspect, the present disclosure relates to the crystalline and amorphous forms discussed above has one or more of a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

In one embodiment, the crystalline and amorphous forms discussed above have a D[V,0.10] particle size between about 0.5 µm and about 15 µm. In one embodiment, the crystalline and amorphous forms discussed above have a D[V,0.10] particle size between about 0.5 µm and about 10 µm. In one embodiment, the crystalline and amorphous forms discussed above have a D[V,0.10] particle size between about 0.5 μm and about 5 μm.

In one embodiment, the crystalline and amorphous forms discussed above have a D[V,0.50] particle size between about 2 μm and about 30 μm. In one embodiment, the crystalline and amorphous forms discussed above have a D[V,0.50] particle size between about 2 μm and about 25 μm. In one embodiment, the crystalline and amorphous forms discussed above have a D[V,0.50] particle size between about 2 μm and about 20 μm. In one embodiment, the crystalline and amorphous forms discussed above have a D[V,0.50] particle size between about 2 μm and about 15 μm.

In one embodiment, the crystalline and amorphous forms discussed above have a D[V,0.90] particle size between about 8 μm and about 600 μm. In one embodiment, the crystalline and amorphous forms discussed above have a D[V,0.90] particle size between about 8 μm and about 500 μm. In one embodiment, the crystalline and amorphous forms discussed above have a D[V,0.90] particle size between about 8 μm and about 400 μm. In one embodiment, the crystalline and amorphous forms discussed above have a D[V,0.90] particle size between about 8 μm and about 300 μm. In one embodiment, the crystalline and amorphous forms discussed above have a D[V,0.90] particle size between about 8 μm and about 200 μm. In one embodiment, the crystalline and amorphous forms discussed above have a D[V,0.90] particle size between about 8 μm and about 100 μm. In one embodiment, the crystalline and amorphous forms discussed above have a D[V,0.90] particle size between about 8 μm and about 75 μm.

In one embodiment, the crystalline and amorphous forms discussed above have a D[4,3] particle size between about 5 μm to about 200 μm. In one embodiment, the crystalline and amorphous forms discussed above have a D[4,3] particle size between about 5 μm to about 150 μm. In one embodiment, the crystalline and amorphous forms discussed above have a D[4,3] particle size between about 5 μm and about 100 μm. In one embodiment, the crystalline and amorphous forms discussed above have a D[4,3] particle size between about 5 μm and about 75 μm. In one embodiment, the crystalline and amorphous forms discussed above have a D[4,3] particle size between about 5 μm and about 50 μm. In one embodiment, the crystalline and amorphous forms discussed above have a D[4,3] particle size between about 5 μm and about 25 μm. In one embodiment, the crystalline and amorphous forms discussed above have a D[4,3] particle size between about 10 μm and about 50 μm. In one embodiment, the crystalline and amorphous forms discussed above have a D[4,3] particle size between about 10 μm and about 30 μm.

In one embodiment, the Form A has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form A has a D[V,0.10] particle size between about 0.5 μm and about 15 μm. In one embodiment, the Form A has a D[V,0.10] particle size between about 0.5 μm and about 10 μm. In one embodiment, the Form A has a D[V,0.10] particle size between about 0.5 μm and about 5 μm.

In one embodiment, the Form A has a D[V,0.50] particle size between about 2 μm and about 30 μm. In one embodiment, the Form A has a D[V,0.50] particle size between about 2 μm and about 25 μm. In one embodiment, the Form A has a D[V,0.50] particle size between about 2 μm and about 20 μm. In one embodiment, the Form A has a D[V,0.50] particle size between about 2 μm and about 15 μm.

In one embodiment, the Form A has a D[V,0.90] particle size between about 8 μm and about 600 μm. In one embodiment, Form A has a D[V,0.90] particle size between about 8 μm and about 500 μm. In one embodiment, Form A has a D[V,0.90] particle size between about 8 μm and about 400 μm. In one embodiment, Form A has a D[V,0.90] particle size between about 8 μm and about 300 μm. In one embodiment, Form A has a D[V,0.90] particle size between about 8 μm and about 200 μm. In one embodiment, the Form A has a D[V,0.90] particle size between about 8 μm and about 100 μm. In one embodiment, the Form A has a D[V,0.90] particle size between about 8 μm and about 75 μm.

In one embodiment, the Form A has a D[4,3] particle size between about 5 μm to about 200 μm. In one embodiment, the Form A has a D[4,3] particle size between about 5 μm to about 150 μm. In one embodiment, the Form A has a D[4,3] particle size between about 5 μm and about 100 μm. In one embodiment, the Form A has a D[4,3] particle size between about 5 μm and about 75 μm. In one embodiment, the Form A has a D[4,3] particle size between about 5 μm and about 50 μm. In one embodiment, the Form A has a D[4,3] particle size between about 5 μm and about 25 μm. In one embodiment, the Form A has a D[4,3] particle size between about 10 μm and about 50 μm. In one embodiment, the Form A has a D[4,3] particle size between about 10 μm and about 30 μm.

In one embodiment, the Form B has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form B has a D[V,0.10] particle size between about 0.5 μm and about 15 μm. In one embodiment, the Form B has a D[V,0.10] particle size between about 0.5 μm and about 10 μm. In one embodiment, the Form B has a D[V,0.10] particle size between about 0.5 μm and about 5 μm.

In one embodiment, the Form B has a D[V,0.50] particle size between about 2 μm and about 30 μm. In one embodiment, the Form B has a D[V,0.50] particle size between about 2 μm and about 25 μm. In one embodiment, the Form B has a D[V,0.50] particle size between about 2 μm and about 20 μm. In one embodiment, the Form B has a D[V,0.50] particle size between about 2 μm and about 15 μm.

In one embodiment, the Form B has a D[V,0.90] particle size between about 8 μm and about 600 μm. In one embodiment, Form B has a D[V,0.90] particle size between about 8 μm and about 500 μm. In one embodiment, Form B has a D[V,0.90] particle size between about 8 μm and about 400 μm. In one embodiment, Form B has a D[V,0.90] particle size between about 8 μm and about 300 μm. In one embodiment, Form B has a D[V,0.90] particle size between about 8 μm and about 200 μm. In one embodiment, the Form B has a D[V,0.90] particle size between about 8 μm and about 100 μm. In one embodiment, the Form B has a D[V,0.90] particle size between about 8 μm and about 75 μm.

In one embodiment, the Form B has a D[4,3] particle size between about 5 μm to about 200 μm. In one embodiment, the Form B has a D[4,3] particle size between about 5 μm to about 150 μm. In one embodiment, the Form B has a D[4,3] particle size between about 5 μm and about 100 μm. In one embodiment, the Form B has a D[4,3] particle size between about 5 µm and about 75 µm. In one embodiment, the Form B has a D[4,3] particle size between about 5 µm and about 50 µm. In one embodiment, the Form B has a D[4,3] particle size between about 5 µm and about 25 µm. In one embodiment, the Form B has a D[4,3] particle size between about 10 µm and about 50 µm. In one embodiment, the Form B has a D[4,3] particle size between about 10 µm and about 30 µm.

In one embodiment, the Form C has one or more of a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

In one embodiment, the Form C has a D[V,0.10] particle size between about 0.5 µm and about 15 µm. In one embodiment, the Form C has a D[V,0.10] particle size between about 0.5 µm and about 10 µm. In one embodiment, the Form C has a D[V,0.10] particle size between about 0.5 µm and about 5 µm.

In one embodiment, the Form C has a D[V,0.50] particle size between about 2 µm and about 30 µm. In one embodiment, the Form C has a D[V,0.50] particle size between about 2 µm and about 25 µm. In one embodiment, the Form C has a D[V,0.50] particle size between about 2 µm and about 20 µm. In one embodiment, the Form C has a D[V,0.50] particle size between about 2 µm and about 15 µm.

In one embodiment, the Form C has a D[V,0.90] particle size between about 8 µm and about 600 µm. In one embodiment, Form C has a D[V,0.90] particle size between about 8 µm and about 500 µm. In one embodiment, Form C has a D[V,0.90] particle size between about 8 µm and about 400 µm. In one embodiment, Form C has a D[V,0.90] particle size between about 8 µm and about 300 µm. In one embodiment, Form C has a D[V,0.90] particle size between about 8 µm and about 200 µm. In one embodiment, the Form C has a D[V,0.90] particle size between about 8 µm and about 100 µm. In one embodiment, the Form C has a D[V,0.90] particle size between about 8 µm and about 75 µm.

In one embodiment, the Form C has a D[4,3] particle size between about 5 µm to about 200 µm. In one embodiment, the Form C has a D[4,3] particle size between about 5 µm to about 150 µm. In one embodiment, the Form C has a D[4,3] particle size between about 5 µm and about 100 µm. In one embodiment, the Form C has a D[4,3] particle size between about 5 µm and about 75 µm. In one embodiment, the Form C has a D[4,3] particle size between about 5 µm and about 50 µm. In one embodiment, the Form C has a D[4,3] particle size between about 5 µm and about 25 µm. In one embodiment, the Form C has a D[4,3] particle size between about 10 µm and about 50 µm. In one embodiment, the Form C has a D[4,3] particle size between about 10 µm and about 30 µm.

In one embodiment, the Form D has one or more of a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

In one embodiment, the Form D has a D[V,0.10] particle size between about 0.5 µm and about 15 µm. In one embodiment, the Form D has a D[V,0.10] particle size between about 0.5 µm and about 10 µm. In one embodiment, the Form D has a D[V,0.10] particle size between about 0.5 µm and about 5 µm.

In one embodiment, the Form D has a D[V,0.50] particle size between about 2 µm and about 30 µm. In one embodiment, the Form D has a D[V,0.50] particle size between about 2 µm and about 25 µm. In one embodiment, the Form D has a D[V,0.50] particle size between about 2 µm and about 20 µm. In one embodiment, the Form D has a D[V,0.50] particle size between about 2 µm and about 15 µm.

In one embodiment, the Form D has a D[V,0.90] particle size between about 8 µm and about 600 µm. In one embodiment, Form D has a D[V,0.90] particle size between about 8 µm and about 500 µm. In one embodiment, Form D has a D[V,0.90] particle size between about 8 µm and about 400 µm. In one embodiment, Form D has a D[V,0.90] particle size between about 8 µm and about 300 µm. In one embodiment, Form D has a D[V,0.90] particle size between about 8 µm and about 200 µm. In one embodiment, the Form D has a D[V,0.90] particle size between about 8 µm and about 100 µm. In one embodiment, the Form D has a D[V,0.90] particle size between about 8 µm and about 75 µm.

In one embodiment, the Form D has a D[4,3] particle size between about 5 µm to about 200 µm. In one embodiment, the Form D has a D[4,3] particle size between about 5 µm to about 150 µm. In one embodiment, the Form D has a D[4,3] particle size between about 5 µm and about 100 µm. In one embodiment, the Form D has a D[4,3] particle size between about 5 µm and about 75 µm. In one embodiment, the Form D has a D[4,3] particle size between about 5 µm and about 50 µm. In one embodiment, the Form D has a D[4,3] particle size between about 5 µm and about 25 µm. In one embodiment, the Form D has a D[4,3] particle size between about 10 µm and about 50 µm. In one embodiment, the Form D has a D[4,3] particle size between about 10 µm and about 30 µm.

In one embodiment, the Form E has one or more of a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

In one embodiment, the Form E has a D[V,0.10] particle size between about 0.5 µm and about 15 µm. In one embodiment, the Form E has a D[V,0.10] particle size between about 0.5 µm and about 10 µm. In one embodiment, the Form E has a D[V,0.10] particle size between about 0.5 µm and about 5 µm.

In one embodiment, the Form E has a D[V,0.50] particle size between about 2 µm and about 30 µm. In one embodiment, the Form E has a D[V,0.50] particle size between about 2 µm and about 25 µm. In one embodiment, the Form E has a D[V,0.50] particle size between about 2 µm and about 20 µm. In one embodiment, the Form E has a D[V,0.50] particle size between about 2 µm and about 15 µm.

In one embodiment, the Form E has a D[V,0.90] particle size between about 8 µm and about 600 µm. In one embodiment, Form E has a D[V,0.90] particle size between about 8 µm and about 500 µm. In one embodiment, Form E has a D[V,0.90] particle size between about 8 µm and about 400 µm. In one embodiment, Form E has a D[V,0.90] particle size between about 8 µm and about 300 µm. In one embodiment, Form E has a D[V,0.90] particle size between about 8 µm and about 200 µm. In one embodiment, the Form E has a D[V,0.90] particle size between about 8 µm and about 100 µm. In one embodiment, the Form E has a D[V,0.90] particle size between about 8 µm and about 75 µm.

In one embodiment, the Form E has a D[4,3] particle size between about 5 μm to about 200 μm. In one embodiment, the Form E has a D[4,3] particle size between about 5 μm to about 150 μm. In one embodiment, the Form E has a D[4,3] particle size between about 5 μm and about 100 μm. In one embodiment, the Form E has a D[4,3] particle size between about 5 μm and about 75 μm. In one embodiment, the Form E has a D[4,3] particle size between about 5 μm and about 50 μm. In one embodiment, the Form E has a D[4,3] particle size between about 5 μm and about 25 μm. In one embodiment, the Form E has a D[4,3] particle size between about 10 μm and about 50 μm. In one embodiment, the Form E has a D[4,3] particle size between about 10 μm and about 30 μm.

In one embodiment, the Form F has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form F has a D[V,0.10] particle size between about 0.5 μm and about 15 μm. In one embodiment, the Form F has a D[V,0.10] particle size between about 0.5 μm and about 10 μm. In one embodiment, the Form F has a D[V,0.10] particle size between about 0.5 μm and about 5 μm.

In one embodiment, the Form F has a D[V,0.50] particle size between about 2 μm and about 30 μm. In one embodiment, the Form F has a D[V,0.50] particle size between about 2 μm and about 25 μm. In one embodiment, the Form F has a D[V,0.50] particle size between about 2 μm and about 20 μm. In one embodiment, the Form F has a D[V,0.50] particle size between about 2 μm and about 15 μm.

In one embodiment, the Form F has a D[V,0.90] particle size between about 8 μm and about 600 μm. In one embodiment, Form F has a D[V,0.90] particle size between about 8 μm and about 500 μm. In one embodiment, Form F has a D[V,0.90] particle size between about 8 μm and about 400 μm. In one embodiment, Form F has a D[V,0.90] particle size between about 8 μm and about 300 μm. In one embodiment, Form F has a D[V,0.90] particle size between about 8 μm and about 200 μm. In one embodiment, the Form F has a D[V,0.90] particle size between about 8 μm and about 100 μm. In one embodiment, the Form F has a D[V,0.90] particle size between about 8 μm and about 75 μm.

In one embodiment, the Form F has a D[4,3] particle size between about 5 μm to about 200 μm. In one embodiment, the Form F has a D[4,3] particle size between about 5 μm to about 150 μm. In one embodiment, the Form F has a D[4,3] particle size between about 5 μm and about 100 μm. In one embodiment, the Form F has a D[4,3] particle size between about 5 μm and about 75 μm. In one embodiment, the Form F has a D[4,3] particle size between about 5 μm and about 50 μm. In one embodiment, the Form F has a D[4,3] particle size between about 5 μm and about 25 μm. In one embodiment, the Form F has a D[4,3] particle size between about 10 μm and about 50 μm. In one embodiment, the Form F has a D[4,3] particle size between about 10 μm and about 30 μm.

In one embodiment, the Form F' has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form F' has a D[V,0.10] particle size between about 0.5 μm and about 15 μm. In one embodiment, the Form F' has a D[V,0.10] particle size between about 0.5 μm and about 10 μm. In one embodiment, the Form F' has a D[V,0.10] particle size between about 0.5 μm and about 5 μm.

In one embodiment, the Form F' has a D[V,0.50] particle size between about 2 μm and about 30 μm. In one embodiment, the Form F' has a D[V,0.50] particle size between about 2 μm and about 25 μm. In one embodiment, the Form F' has a D[V,0.50] particle size between about 2 μm and about 20 μm. In one embodiment, the Form F' has a D[V,0.50] particle size between about 2 μm and about 15 μm.

In one embodiment, the Form F' has a D[V,0.90] particle size between about 8 μm and about 600 μm. In one embodiment, Form F' has a D[V,0.90] particle size between about 8 μm and about 500 μm. In one embodiment, Form F' has a D[V,0.90] particle size between about 8 μm and about 400 μm. In one embodiment, Form F' has a D[V,0.90] particle size between about 8 μm and about 300 μm. In one embodiment, Form F' has a D[V,0.90] particle size between about 8 μm and about 200 μm. In one embodiment, the Form F' has a D[V,0.90] particle size between about 8 μm and about 100 μm. In one embodiment, the Form F' has a D[V,0.90] particle size between about 8 μm and about 75 μm.

In one embodiment, the Form F' has a D[4,3] particle size between about 5 μm to about 200 μm. In one embodiment, the Form F' has a D[4,3] particle size between about 5 μm to about 150 μm. In one embodiment, the Form F' has a D[4,3] particle size between about 5 μm and about 100 μm. In one embodiment, the Form F' has a D[4,3] particle size between about 5 μm and about 75 μm. In one embodiment, the Form F' has a D[4,3] particle size between about 5 μm and about 50 μm. In one embodiment, the Form F' has a D[4,3] particle size between about 5 μm and about 25 μm. In one embodiment, the Form F' has a D[4,3] particle size between about 10 μm and about 50 μm. In one embodiment, the Form F' has a D[4,3] particle size between about 10 μm and about 30 μm.

In one embodiment, the Form G has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form G has a D[V,0.10] particle size between about 0.5 μm and about 15 μm. In one embodiment, the Form G has a D[V,0.10] particle size between about 0.5 μm and about 10 μm. In one embodiment, the Form G has a D[V,0.10] particle size between about 0.5 μm and about 5 μm.

In one embodiment, the Form G has a D[V,0.50] particle size between about 2 μm and about 30 μm. In one embodiment, the Form G has a D[V,0.50] particle size between about 2 μm and about 25 μm. In one embodiment, the Form G has a D[V,0.50] particle size between about 2 μm and about 20 μm. In one embodiment, the Form G has a D[V,0.50] particle size between about 2 μm and about 15 μm.

In one embodiment, the Form G has a D[V,0.90] particle size between about 8 μm and about 600 μm. In one embodiment, Form G has a D[V,0.90] particle size between about 8 μm and about 500 μm. In one embodiment, Form G has a D[V,0.90] particle size between about 8 μm and about 400 μm. In one embodiment, Form G has a D[V,0.90] particle size between about 8 μm and about 300 μm. In one embodiment, Form G has a D[V,0.90] particle size between about 8 μm and about 200 μm. In one embodiment, the Form G has a D[V,0.90] particle size between about 8 μm and about 100

μm. In one embodiment, the Form G has a D[V,0.90] particle size between about 8 μm and about 75 μm.

In one embodiment, the Form G has a D[4,3] particle size between about 5 μm to about 200 μm. In one embodiment, the Form G has a D[4,3] particle size between about 5 μm to about 150 μm. In one embodiment, the Form G has a D[4,3] particle size between about 5 μm and about 100 μm. In one embodiment, the Form G has a D[4,3] particle size between about 5 μm and about 75 μm. In one embodiment, the Form G has a D[4,3] particle size between about 5 μm and about 50 μm. In one embodiment, the Form G has a D[4,3] particle size between about 5 μm and about 25 μm. In one embodiment, the Form G has a D[4,3] particle size between about 10 μm and about 50 μm. In one embodiment, the Form G has a D[4,3] particle size between about 10 μm and about 30 μm.

In one embodiment, the Form H has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form H has a D[V,0.10] particle size between about 0.5 μm and about 15 μm. In one embodiment, the Form H has a D[V,0.10] particle size between about 0.5 μm and about 10 μm. In one embodiment, the Form H has a D[V,0.10] particle size between about 0.5 μm and about 5 μm.

In one embodiment, the Form H has a D[V,0.50] particle size between about 2 μm and about 30 μm. In one embodiment, the Form H has a D[V,0.50] particle size between about 2 μm and about 25 μm. In one embodiment, the Form H has a D[V,0.50] particle size between about 2 μm and about 20 μm. In one embodiment, the Form H has a D[V,0.50] particle size between about 2 μm and about 15 μm.

In one embodiment, the Form H has a D[V,0.90] particle size between about 8 μm and about 600 μm. In one embodiment, Form H has a D[V,0.90] particle size between about 8 μm and about 500 μm. In one embodiment, Form H has a D[V,0.90] particle size between about 8 μm and about 400 μm. In one embodiment, Form H has a D[V,0.90] particle size between about 8 μm and about 300 μm. In one embodiment, Form H has a D[V,0.90] particle size between about 8 μm and about 200 μm. In one embodiment, the Form H has a D[V,0.90] particle size between about 8 μm and about 100 μm. In one embodiment, the Form H has a D[V,0.90] particle size between about 8 μm and about 75 μm.

In one embodiment, the Form H has a D[4,3] particle size between about 5 μm to about 200 μm. In one embodiment, the Form H has a D[4,3] particle size between about 5 μm to about 150 μm. In one embodiment, the Form H has a D[4,3] particle size between about 5 μm and about 100 μm. In one embodiment, the Form H has a D[4,3] particle size between about 5 μm and about 75 μm. In one embodiment, the Form H has a D[4,3] particle size between about 5 μm and about 50 μm. In one embodiment, the Form H has a D[4,3] particle size between about 5 μm and about 25 μm. In one embodiment, the Form H has a D[4,3] particle size between about 10 μm and about 50 μm. In one embodiment, the Form H has a D[4,3] particle size between about 10 μm and about 30 μm.

In one embodiment, the Form H' has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form H' has a D[V,0.10] particle size between about 0.5 μm and about 15 μm. In one embodiment, the Form H' has a D[V,0.10] particle size between about 0.5 μm and about 10 μm. In one embodiment, the Form H' has a D[V,0.10] particle size between about 0.5 μm and about 5 μm.

In one embodiment, the Form H' has a D[V,0.50] particle size between about 2 μm and about 30 μm. In one embodiment, the Form H' has a D[V,0.50] particle size between about 2 μm and about 25 μm. In one embodiment, the Form H' has a D[V,0.50] particle size between about 2 μm and about 20 μm. In one embodiment, the Form H' has a D[V,0.50] particle size between about 2 μm and about 15 μm.

In one embodiment, the Form H' has a D[V,0.90] particle size between about 8 μm and about 600 μm. In one embodiment, Form H' has a D[V,0.90] particle size between about 8 μm and about 500 μm. In one embodiment, Form H' has a D[V,0.90] particle size between about 8 μm and about 400 μm. In one embodiment, Form H' has a D[V,0.90] particle size between about 8 μm and about 300 μm. In one embodiment, Form H' has a D[V,0.90] particle size between about 8 μm and about 200 μm. In one embodiment, the Form H' has a D[V,0.90] particle size between about 8 μm and about 100 μm. In one embodiment, the Form H' has a D[V,0.90] particle size between about 8 μm and about 75 μm.

In one embodiment, the Form H' has a D[4,3] particle size between about 5 μm to about 200 μm. In one embodiment, the Form H' has a D[4,3] particle size between about 5 μm to about 150 μm. In one embodiment, the Form H' has a D[4,3] particle size between about 5 μm and about 100 μm. In one embodiment, the Form H' has a D[4,3] particle size between about 5 μm and about 75 μm. In one embodiment, the Form H' has a D[4,3] particle size between about 5 μm and about 50 μm. In one embodiment, the Form H' has a D[4,3] particle size between about 5 μm and about 25 μm. In one embodiment, the Form H' has a D[4,3] particle size between about 10 μm and about 50 μm. In one embodiment, the Form H' has a D[4,3] particle size between about 10 μm and about 30 μm.

In one embodiment, the Form J has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form J has a D[V,0.10] particle size between about 0.5 μm and about 15 μm. In one embodiment, the Form H has a D[V,0.10] particle size between about 0.5 μm and about 10 μm. In one embodiment, the Form H has a D[V,0.10] particle size between about 0.5 μm and about 5 μm.

In one embodiment, the Form J has a D[V,0.50] particle size between about 2 μm and about 30 μm. In one embodiment, the Form J has a D[V,0.50] particle size between about 2 μm and about 25 μm. In one embodiment, the Form J has a D[V,0.50] particle size between about 2 μm and about 20 μm. In one embodiment, the Form J has a D[V,0.50] particle size between about 2 μm and about 15 μm.

In one embodiment, the Form J has a D[V,0.90] particle size between about 8 μm and about 600 μm. In one embodiment, Form J has a D[V,0.90] particle size between about 8 μm and about 500 μm. In one embodiment, Form J has a D[V,0.90] particle size between about 8 μm and about 400

μm. In one embodiment, Form J has a D[V,0.90] particle size between about 8 μm and about 300 μm. In one embodiment, Form J has a D[V,0.90] particle size between about 8 μm and about 200 μm. In one embodiment, the Form J has a D[V,0.90] particle size between about 8 μm and about 100 μm. In one embodiment, the Form J has a D[V,0.90] particle size between about 8 μm and about 75 μm.

In one embodiment, the Form J has a D[4,3] particle size between about 5 μm to about 200 μm. In one embodiment, the Form J has a D[4,3] particle size between about 5 μm to about 150 μm. In one embodiment, the Form J has a D[4,3] particle size between about 5 μm and about 100 μm. In one embodiment, the Form J has a D[4,3] particle size between about 5 μm and about 75 μm. In one embodiment, the Form J has a D[4,3] particle size between about 5 μm and about 50 μm. In one embodiment, the Form J has a D[4,3] particle size between about 5 μm and about 25 μm. In one embodiment, the Form J has a D[4,3] particle size between about 10 μm and about 50 μm. In one embodiment, the Form J has a D[4,3] particle size between about 10 μm and about 30 μm.

In one embodiment, the Form K has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form K has a D[V,0.10] particle size between about 0.5 μm and about 15 μm. In one embodiment, the Form K has a D[V,0.10] particle size between about 0.5 μm and about 10 μm. In one embodiment, the Form K has a D[V,0.10] particle size between about 0.5 μm and about 5 μm.

In one embodiment, the Form K has a D[V,0.50] particle size between about 2 μm and about 30 μm. In one embodiment, the Form K has a D[V,0.50] particle size between about 2 μm and about 25 μm. In one embodiment, the Form K has a D[V,0.50] particle size between about 2 μm and about 20 μm. In one embodiment, the Form K has a D[V,0.50] particle size between about 2 μm and about 15 μm.

In one embodiment, the Form K has a D[V,0.90] particle size between about 8 μm and about 600 μm. In one embodiment, Form K has a D[V,0.90] particle size between about 8 μm and about 500 μm. In one embodiment, Form K has a D[V,0.90] particle size between about 8 μm and about 400 μm. In one embodiment, Form K has a D[V,0.90] particle size between about 8 μm and about 300 μm. In one embodiment, Form K has a D[V,0.90] particle size between about 8 μm and about 200 μm. In one embodiment, the Form K has a D[V,0.90] particle size between about 8 μm and about 100 μm. In one embodiment, the Form K has a D[V,0.90] particle size between about 8 μm and about 75 μm.

In one embodiment, the Form K has a D[4,3] particle size between about 5 μm to about 200 μm. In one embodiment, the Form K has a D[4,3] particle size between about 5 μm to about 150 μm. In one embodiment, the Form K has a D[4,3] particle size between about 5 μm and about 100 μm. In one embodiment, the Form K has a D[4,3] particle size between about 5 μm and about 75 μm. In one embodiment, the Form K has a D[4,3] particle size between about 5 μm and about 50 μm. In one embodiment, the Form K has a D[4,3] particle size between about 5 μm and about 25 μm. In one embodiment, the Form K has a D[4,3] particle size between about 10 μm and about 50 μm. In one embodiment, the Form K has a D[4,3] particle size between about 10 μm and about 30 μm.

In one embodiment, the Form L has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form L has a D[V,0.10] particle size between about 0.5 μm and about 15 μm. In one embodiment, the Form L has a D[V,0.10] particle size between about 0.5 μm and about 10 μm. In one embodiment, the Form L has a D[V,0.10] particle size between about 0.5 μm and about 5 μm.

In one embodiment, the Form L has a D[V,0.50] particle size between about 2 μm and about 30 μm. In one embodiment, the Form L has a D[V,0.50] particle size between about 2 μm and about 25 μm. In one embodiment, the Form L has a D[V,0.50] particle size between about 2 μm and about 20 μm. In one embodiment, the Form L has a D[V,0.50] particle size between about 2 μm and about 15 μm.

In one embodiment, the Form L has a D[V,0.90] particle size between about 8 μm and about 600 μm. In one embodiment, Form L has a D[V,0.90] particle size between about 8 μm and about 500 μm. In one embodiment, Form L has a D[V,0.90] particle size between about 8 μm and about 400 μm. In one embodiment, Form L has a D[V,0.90] particle size between about 8 μm and about 300 μm. In one embodiment, Form L has a D[V,0.90] particle size between about 8 μm and about 200 μm. In one embodiment, the Form L has a D[V,0.90] particle size between about 8 μm and about 100 μm. In one embodiment, the Form L has a D[V,0.90] particle size between about 8 μm and about 75 μm.

In one embodiment, the Form L has a D[4,3] particle size between about 5 μm to about 200 μm. In one embodiment, the Form L has a D[4,3] particle size between about 5 μm to about 150 μm. In one embodiment, the Form L has a D[4,3] particle size between about 5 μm and about 100 μm. In one embodiment, the Form L has a D[4,3] particle size between about 5 μm and about 75 μm. In one embodiment, the Form L has a D[4,3] particle size between about 5 μm and about 50 μm. In one embodiment, the Form L has a D[4,3] particle size between about 5 μm and about 25 μm. In one embodiment, the Form L has a D[4,3] particle size between about 10 μm and about 50 μm. In one embodiment, the Form L has a D[4,3] particle size between about 10 μm and about 30 μm.

In one embodiment, the Form M has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form M has a D[V,0.10] particle size between about 0.5 μm and about 15 μm. In one embodiment, the Form M has a D[V,0.10] particle size between about 0.5 μm and about 10 μm. In one embodiment, the Form M has a D[V,0.10] particle size between about 0.5 μm and about 5 μm.

In one embodiment, the Form M has a D[V,0.50] particle size between about 2 μm and about 30 μm. In one embodiment, the Form M has a D[V,0.50] particle size between about 2 μm and about 25 μm. In one embodiment, the Form M has a D[V,0.50] particle size between about 2 μm and about 20 μm. In one embodiment, the Form M has a D[V,0.50] particle size between about 2 μm and about 15 μm.

In one embodiment, the Form M has a D[V,0.90] particle size between about 8 μm and about 600 μm. In one embodiment, Form M has a D[V,0.90] particle size between about 8 μm and about 500 μm. In one embodiment, Form M has a D[V,0.90] particle size between about 8 μm and about 400 μm. In one embodiment, Form M has a D[V,0.90] particle size between about 8 μm and about 300 μm. In one embodiment, Form M has a D[V,0.90] particle size between about 8 μm and about 200 μm. In one embodiment, the Form M has a D[V,0.90] particle size between about 8 μm and about 100 μm. In one embodiment, the Form M has a D[V,0.90] particle size between about 8 μm and about 75 μm.

In one embodiment, the Form M has a D[4,3] particle size between about 5 μm to about 200 μm. In one embodiment, the Form M has a D[4,3] particle size between about 5 μm to about 150 μm. In one embodiment, the Form M has a D[4,3] particle size between about 5 μm and about 100 μm. In one embodiment, the Form M has a D[4,3] particle size between about 5 μm and about 75 μm. In one embodiment, the Form M has a D[4,3] particle size between about 5 μm and about 50 μm. In one embodiment, the Form M has a D[4,3] particle size between about 5 μm and about 25 μm. In one embodiment, the Form M has a D[4,3] particle size between about 10 μm and about 50 μm. In one embodiment, the Form M has a D[4,3] particle size between about 10 μm and about 30 μm.

In one embodiment, the Form N has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the Form N has a D[V,0.10] particle size between about 0.5 μm and about 15 μm. In one embodiment, the Form N has a D[V,0.10] particle size between about 0.5 μm and about 10 μm. In one embodiment, the Form N has a D[V,0.10] particle size between about 0.5 μm and about 5 μm.

In one embodiment, the Form N has a D[V,0.50] particle size between about 2 μm and about 30 μm. In one embodiment, the Form N has a D[V,0.50] particle size between about 2 μm and about 25 μm. In one embodiment, the Form N has a D[V,0.50] particle size between about 2 μm and about 20 μm. In one embodiment, the Form N has a D[V,0.50] particle size between about 2 μm and about 15 μm.

In one embodiment, the Form N has a D[V,0.90] particle size between about 8 μm and about 600 μm. In one embodiment, Form N has a D[V,0.90] particle size between about 8 μm and about 500 μm. In one embodiment, Form N has a D[V,0.90] particle size between about 8 μm and about 400 μm. In one embodiment, Form N has a D[V,0.90] particle size between about 8 μm and about 300 μm. In one embodiment, Form N has a D[V,0.90] particle size between about 8 μm and about 200 μm. In one embodiment, the Form N has a D[V,0.90] particle size between about 8 μm and about 100 μm. In one embodiment, the Form N has a D[V,0.90] particle size between about 8 μm and about 75 μm.

In one embodiment, the Form N has a D[4,3] particle size between about 5 μm to about 200 μm. In one embodiment, the Form N has a D[4,3] particle size between about 5 μm to about 150 μm. In one embodiment, the Form N has a D[4,3] particle size between about 5 μm and about 100 μm. In one embodiment, the Form N has a D[4,3] particle size between about 5 μm and about 75 μm. In one embodiment, the Form N has a D[4,3] particle size between about 5 μm and about 50 μm. In one embodiment, the Form N has a D[4,3] particle size between about 5 μm and about 25 μm. In one embodiment, the Form N has a D[4,3] particle size between about 10 μm and about 50 μm. In one embodiment, the Form N has a D[4,3] particle size between about 10 μm and about 30 μm.

In one embodiment, the amorphous form has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the amorphous form has a D[V,0.10] particle size between about 0.5 μm and about 15 μm. In one embodiment, the amorphous form has a D[V,0.10] particle size between about 0.5 μm and about 10 μm. In one embodiment, the amorphous form has a D[V,0.10] particle size between about 0.5 μm and about 5 μm.

In one embodiment, the amorphous form has a D[V,0.50] particle size between about 2 μm and about 30 μm. In one embodiment, the amorphous form has a D[V,0.50] particle size between about 2 μm and about 25 μm. In one embodiment, the amorphous form has a D[V,0.50] particle size between about 2 μm and about 20 μm. In one embodiment, the amorphous form has a D[V,0.50] particle size between about 2 μm and about 15 μm.

In one embodiment, the amorphous form has a D[V,0.90] particle size between about 8 μm and about 600 μm. In one embodiment, the amorphous form has a D[V,0.90] particle size between about 8 μm and about 500 μm. In one embodiment, the amorphous form has a D[V,0.90] particle size between about 8 μm and about 400 μm. In one embodiment, the amorphous form has a D[V,0.90] particle size between about 8 μm and about 300 μm. In one embodiment, the amorphous form has a D[V,0.90] particle size between about 8 μm and about 200 μm. In one embodiment, the amorphous form has a D[V,0.90] particle size between about 8 μm and about 100 μm. In one embodiment, the amorphous form has a D[V,0.90] particle size between about 8 μm and about 75 μm.

In one embodiment, the amorphous form has a D[4,3] particle size between about 5 μm to about 200 μm. In one embodiment, the amorphous form has a D[4,3] particle size between about 5 μm to about 150 μm. In one embodiment, the amorphous form has a D[4,3] particle size between about 5 μm and about 100 μm. In one embodiment, the amorphous form has a D[4,3] particle size between about 5 μm and about 75 μm. In one embodiment, the amorphous form has a D[4,3] particle size between about 5 μm and about 50 μm. In one embodiment, the amorphous form has a D[4,3] particle size between about 5 μm and about 25 μm. In one embodiment, the amorphous form has a D[4,3] particle size between about 10 μm and about 50 μm. In one embodiment, the amorphous form has a D[4,3] particle size between about 10 μm and about 30 μm.

In one aspect, the present disclosure relates to a composition comprising a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide has one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm.

In one embodiment, the composition comprises a crystalline or amorphous form of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide having a D[V,0.10] particle size between about 0.5 μm and about 15 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl) pentanamide having a D[V,0.10] particle size between about 0.5 μm and about 10 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.10] particle size between about 0.5 μm and about 5 μm.

In one embodiment, the composition comprises a crystalline or amorphous form of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide having a D[V,0.50] particle size between about 2 μm and about 30 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.50] particle size between about 2 μm and about 25 μm. In one embodiment, the composition comprises a crystalline or amorphous form of a hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V, 0.50] particle size between about 2 μm and about 20 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl) pentanamide having a D[V,0.50] particle size between about 2 μm and about 15 μm.

In one embodiment, the composition comprises a crystalline or amorphous form of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide having a D[V,0.90] particle size between about 8 μm and about 600 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.90] particle size between about 8 μm and about 500 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.90] particle size between about 8 μm and about 400 μm. In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V, 0.90] particle size between about 8 μm and about 300 μm. In one embodiment, the composition comprises a crystalline or amorphous form of a hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl) pentanamide having a D[V,0.90] particle size between about 8 μm and about 200 μm. In one embodiment, the composition comprises a crystalline or amorphous form of a hydrobromide salt of (S) (((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.90] particle size between about 8 μm and about 100 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[V,0.90] particle size between about 8 μm and about 75 μm.

In one embodiment, the composition comprises a crystalline or amorphous form of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide having a D[4,3] particle size between about 5 μm and about 200 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 5 μm and about 150 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 5 μm and about 100 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 5 μm and about 75 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 5 μm and about 50 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 10 μm and about 50 μm. In one embodiment, the composition comprises a crystalline or amorphous form of a hydrobromide salt of (S)-2-(((S)-6,8-difluoro-1,2,3,4-tetrahydronaphthalen-2-yl) amino)-N-(1-(2-methyl-1-(neopentylamino) propan-2-yl)-1H-imidazol-4-yl)pentanamide having a D[4,3] particle size between about 10 μm and about 40 In one embodiment, the composition comprises a crystalline or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having a D[4,3] particle size between about 10 μm and about 30 μm.

In one embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm is an amorphous form. In one embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm is a crystalline form. In one embodiment, the amorphous or crystalline hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having one or more of a D[V,0.10] particle size between about 0.5 μm and about 15 μm, a D[V,0.50] particle size between about 2 μm and about 30 μm, a D[V,0.90] particle size between about 8 μm and about 600 or a D[4,3] particle size of about 5 μm to about 200 μm is a compound of Formula (I)

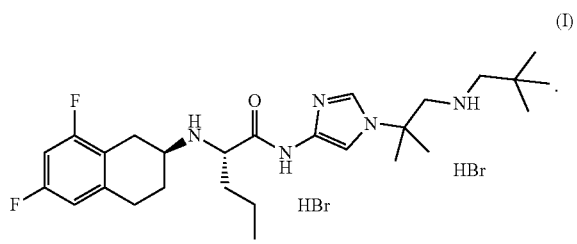 [SMILES: CCC[C@H](N[C@H]1CCc2cc(F)cc(F)c2C1)C(=O)Nc1cn(C(C)(C)CNCC(C)(C)C)cn1 ; Br ; Br]

(I)

In one embodiment, the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having one or more of a D[V,0.10] particle size between about 0.5 μm and about 15 μm, a D[V,0.50] particle size between about 2 μm and about 30 μm, a D[V,0.90] particle size between about 8 μm and about 600 μm, or a D[4,3] particle size of about 5 μm to about 200 μm is a compound of Formula (II)

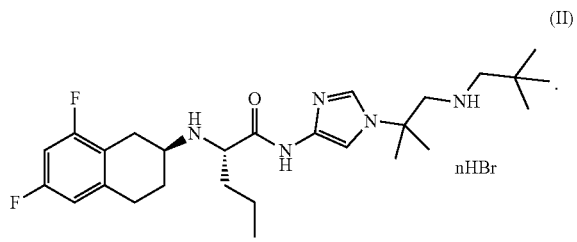

(II)

In one embodiment, the crystalline form is selected from the group consisting of Form A, Form B, Form C, Form D, Form E, Form F, Form F', Form G, Form H, Form H', Form J, Form K, Form L, Form M, and Form N. In one embodiment, the crystalline form is Form A.

In some embodiments, the crystalline form is Form A which has one or more particle parameters selected from the group consisting of D[V,0.10], D[V,0.50], D[V,0.90], and D[4,3]. In other embodiments, the crystalline form is Form A has two or more particle parameters selected from the group consisting of D[V,0.10], D[V,0.50], D[V,0.90], and D[4,3].

Each of the embodiments described herein can be combined with any other embodiment described herein not inconsistent with the embodiment with which it is combined.

In other embodiments, the crystalline form is Form A having a D[V,0.10] of from about 0.5 μm to about 15 μm; from about 0.5 μm to about 10 μm; from about 0.5 μm to about 5 μm; from about 1 μm to about 15 μm; from about 1 μm to about 10 μm; from about 1 μm to about 7.5 μm; from about 1 μm to about 5 μm; from about 2 μm to about 10 μm; from about 2 μm to about 7.5 μm; from about 2 μm to about 5 μm; from about 3 μm to about 10 μm; from about 3 μm to about 7.5 μm; or from about 3 μm to about 5 μm. In other embodiments, the crystalline form is Form A having a D[V,0.10] of less than 15 μm; less than 12.5 μm; less than 10 μm; less than 9 μm; less than 8 μm; less than 7 μm; less than 6 μm; less than 5 μm; less than 4 μm; or less than 3 μm.

In other embodiments, the crystalline form is Form A having a D[V,0.50] of from about 2 μm to about 30 μm; 2 μm to about 20 μm; from about 2 μm to about 15 μm; from about 2 μm to about 10 μm; from about 5 μm to about 30 μm; from about 5 μm to about 25 μm; from about 5 μm to about 20 μm; from about 5 μm to about 15 μm; from about 5 μm to about 10 μm; from about 7.5 μm to about 30 μm; from about 7.5 μm to about 25 μm; from about 7.5 μm to about 20 μm; from about 7.5 μm to about 15 μm; from about 7.5 μm to about 10 μm; from about 10 μm to about 30 μm; from about 10 μm to about 25 μm; from about 10 μm to about 20 μm; from about 10 μm to about 15 μm; from about 12 μm to about 15 μm; from about 15 μm to about 30 μm; from about 15 μm to about 25 μm; from about 15 μm to about 20 μm; from about 20 μm to about 30 μm. In other embodiments, the crystalline form is Form A having a D[V,0.50] of less than 30 μm; less than 25 μm; less than 20 μm; less than 15 μm; less than 12.5 μm; or less than 10 μm.

In other embodiments, the crystalline form is Form A having a D[V,0.90] of from about 8 μm to about 600 μm; from about 8 μm to about 575 μm; from about 8 μm to about 550 μm; from about 8 μm to about 525 μm; from about 8 μm to about 500 μm; from about 8 μm to about 475 μm; from about 8 μm to about 450 μm; from about 8 μm to about 425 μm; from about 8 μm to about 400 μm; from about 8 μm to about 375 μm; from about 8 μm to about 350 μm; from about 8 μm to about 325 μm; from about 8 μm to about 300 μm; from about 8 μm to about 275 μm; from about 8 μm to about 250 μm; from about 8 μm to about 225 μm; from about 8 μm to about 200 μm; from about 8 μm to about 175 μm; from about 8 μm to about 150 μm; from about 8 μm to about 175 μm; from about 8 μm to about 150 μm; from about 8 μm to about 125 μm; from about 8 μm to about 100 μm; from about 8 μm to about 75 μm; from about 8 μm to about 50 μm; from about 8 μm to about 40 μm; from about 8 μm to about 30 μm; from about 10 μm to about 600 μm; from about 10 μm to about 575 μm; from about 10 μm to about 550 μm; from about 10 μm to about 525 μm; from about 10 μm to about 500 μm; from about 10 μm to about 475 μm; from about 10 μm to about 450 μm; from about 10 μm to about 425 μm; from about 10 μm to about 400 μm; from about 10 μm to about 375 μm; from about 10 μm to about 350 μm; from about 10 μm to about 325 μm; from about 10 μm to about 300 μm; from about 10 μm to about 275 μm; from about 10 μm to about 250 μm; from about 10 μm to about 225 μm; from about 10 μm to about 200 μm; from about 10 μm to about 175 μm; from about 10 μm to about 150 μm; from about 10 μm to about 125 μm; from about 10 μm to about 100 μm; from about 10 μm to about 75 μm; from about 10 μm to about 60 μm; from about 10 μm to about 50 μm; from about 25 μm to about 600 μm; from about 25 μm to about 575 μm; from about 25 μm to about 550 μm; from about 25 μm to about 525 μm; from about 25 μm to about 500 μm; from about 25 μm to about 475 μm; from about 25 μm to about 450 μm; from about 25 μm to about 425 μm; from about 25 μm to about 400 μm; from about 25 μm to about 375 μm; from about 25 μm to about 350 μm; from about 25 μm to about 325 μm; from about 25 μm to about 300 μm; from about 25 μm to about 275 μm; from about 25 μm to about 250 μm; from about 25 μm to about 225 μm; from about 25 μm to about 200 μm; from about 25 μm to about 175 μm; from about 25 μm to about 150 μm; from about 25 μm to about 125 μm; from about 25 μm to about 100 μm; from about 25 μm to about 75 μm; from about 25 μm to about 50 μm; from about 40 μm to about 600 μm; from about 40 μm to about 575 μm; from about 40 μm to about 550 μm; from about 40 μm to about 525 μm; from about 40 μm to about 500 μm; from about 40 μm to about 475 μm; from about 40 μm to about 450 μm; from about 40 μm to about 425 μm; from about 40 μm to about 400 μm; from about 40 μm to about 375 μm; from about 40 μm to about 350 μm; from about 40 μm to about 325 μm; from about 40 μm to about 300 μm; from about 40 μm to about 275 μm; from about 40 μm to about 250 μm; from about 40 μm to about 225 μm; from about 40 μm to about 200 μm; from about 40 μm to about 175 μm; from about 40 μm to about 150 μm; from about 40 μm to about 125 μm; from about 40 μm to about 100 μm; from about 40 μm to about 75 μm; from about 40 μm to about 50 μm; from about 50 μm to about 600 μm; from about 50 μm to about 575 μm; from about 50 μm to about 550 μm; from about 50 μm to about 525 μm; from about 50 μm to about 500 μm; from about 50 μm to about 475 μm; from about 50 μm to about 450 μm; from about 50 μm to about 425 μm; from about 50 μm to about 400 μm; from about 50 μm to about 375 μm; from about 50 μm to about 350 μm; from about 50 μm to about 325 μm; from about 50 μm to about 300 μm; from about 50 μm to about 275 μm; from about 50 μm to about 250 μm; from about 50 μm to about 225 μm; from about 50 μm to about 200 μm; from about 50 μm to about 175 μm; from about 50 μm to about 150 μm; from about 50 μm to about 125 μm; from about 50 μm to about 100 μm; from about 50 μm to about 75 μm; from about 75 μm to about 600 μm; from about 75 μm to about 575 μm; from about 75 μm to about 550 μm; from about 75 μm to about 525 μm; from about 75 μm to about 500 μm; from about 75 μm to about 475 μm; from about 75 μm to about 450 μm; from about 75 μm to about 425 μm; from about 75 μm to about 400 μm; from about 75 μm to about 375 μm; from about 75 μm to about 350 μm; from about 75 μm to about 325 μm; from about 75 μm to about 300 μm; from about 75 μm to about 275 μm; from about 75 μm to about 250 μm; from about 75 μm to about 225 μm; from about 75 μm to about 200 μm; from about 75 μm to about 175 μm; from about 75 μm to about 150 μm; from about 75 μm to about 125 μm; from about 75 μm to about 100 μm; from about 100 μm to about 600 μm; from about 100 μm to about 575 μm; from about 100 μm to about 550 μm; from about 100 μm to about 525 μm; from about 100 μm to about 500 μm; from about 100 μm to about 475 μm; from about 100 μm to about 450 μm; from about 100 μm to about 425 μm; from about 100 μm to about 400 μm; from about 100 μm to about 375 μm; from about 100 μm to about 350 μm; from about 100 μm to about 325 μm; from about 100 μm to about 300 μm; from about 100 μm to about 275 μm; from about 100 μm to about 250 μm; from about 100 μm to about 225 μm; from about 100 μm to about 200 μm; from about 100 μm to about 175 μm; from about 100 μm to about 150 μm; from about 100 μm to about 125 μm; from about 125 μm to about 600 μm; from about 125 μm to about 575 μm; from about 125 μm to about 550 μm; from about 125 μm to about 525 μm; from about 125 μm to about 500 μm; from about 125 μm to about 475 μm; from about 125 μm to about 450 μm; from about 125 μm to about 425 μm; from about 125 μm to about 400 μm; from about 125 μm to about 375 μm; from about 125 μm to about 350 μm; from about 125 μm to about 325 μm; from about 125 μm to about 300 μm; from about 125 μm to about 275 μm; from about 125 μm to about 250 μm; from about 125 μm to about 225 μm; from about 125 μm to about 200 μm; from about 125 μm to about 175 μm; from about 125 μm to about 150 μm; from about 125 μm to about 600 μm; from about 150 μm to about 575 μm; from about 150 μm to about 550 μm; from about 150 μm to about 525 μm; from about 150 μm to about 500 μm; from about 150 μm to about 475 μm; from about 150 μm to about 450 μm; from about 150 μm to about 425 μm; from about 150 μm to about 400 μm; from about 150 μm to about 375 μm; from about 150 μm to about 350 μm; from about 150 μm to about 325 μm; from about 150 μm to about 300 μm; from about 150 μm to about 275 μm; from about 150 μm to about 250 μm; from about 150 μm to about 225 μm; from about 150 μm to about 200 μm; from about 150 μm to about 175 μm; from about 175 μm to about 600 μm; from about 175 μm to about 575 μm; from about 175 μm to about 550 μm; from about 175 μm to about 525 μm; from about 175 μm to about 500 μm; from about 175 μm to about 475 μm; from about 175 μm to about 450 μm; from about 175 μm to about 425 μm; from about 175 μm to about 400 μm; from about 175 μm to about 375 μm; from about 175 μm to about 350 μm; from about 175 μm to about 325 μm; from about 175 μm to about 300 μm; from about 175 μm to about 275 μm; from about 175 μm to about 250 μm; from about 175 μm to about 225 μm; from about 175 μm to about 200 μm; from about 200 μm to about 600 μm; from about 200 μm to about 575 μm; from about 200 μm to about 550 μm; from about 200 μm to about 525 μm; from about 200 μm to about 500 μm; from about 200 μm to about 475 μm; from about 200 μm to about 450 μm; from about 200 μm to about 425 μm; from about 200 μm to about 400 μm; from about 200 μm to about 375 μm; from about 200 μm to about 350 μm; from about 200 μm to about 325 μm; from about 200 μm to about 300 μm; from about 200 μm to about 275 μm; from about 200 μm to about 250 μm; from about 200 μm to about 225 μm; from about 225 μm to about 600 μm; from about 225 μm to about 575 μm; from about 225 μm to about 550 μm; from about 225 μm to about 525 μm; from about 225 μm to about 500 μm; from about 225 μm to about 475 μm; from about 225 μm to about 450 μm; from about 225 μm to about 425 μm; from about 225 μm to about 400 μm; from about 225 μm to about 375 μm; from about 225 μm to about 350 μm; from about 225 μm to about 325 μm; from about 225 μm to about 300 μm; from about 225 μm to about 275 μm; from about 225 μm to about 250 μm; from about 250 μm to about 600 μm; from about 250 μm to about 575 μm; from about 250 μm to about 550 μm; from about 250 μm to about 525 μm; from about 250 μm to about 500 μm; from about 250 μm to about 475 μm; from about 250 μm to about 450 μm; from about 250 μm to about 425 μm; from about 250 μm to about 400 μm; from about 250 μm to about 375 μm; from about 250 μm to about 350 μm; from about 250 μm to about 325 μm; from about 250 μm to about 300 μm; from about 250 μm to about 275 μm; from about 275 μm to about 600 μm; from about 275 μm to about 575 μm; from about 275 μm to about 550 μm; from about 275 μm to about 525 μm; from about 275 μm to about 500 μm; from about 275 μm to about 475 μm; from about 275 μm to about 450 μm; from about 275 μm to about 425 μm; from about 275 μm to about 400 μm; from about 275 μm to about 375 μm; from about 275 μm to about 350 μm; from about 275 μm to about 325 μm; from about 275 μm to about 300 μm; from about 300 μm to about 600 μm; from about 300 μm to about 575 μm; from about 300 μm to about 550 μm; from about 300 μm to about 525 μm; from about 300 μm to about 500 μm; from about 300 μm to about 475 μm; from about 300 μm to about 450 μm; from about 300 μm to about 425 μm; from about 300 μm to about 400 μm; from about 300 μm to about 375 μm; from about 300 μm to about 350 μm; from about 300 μm to about 325 μm; from about 325 μm to about 600 μm; from about 325 μm to about 575 μm; from about 325 μm to about 550 μm; from about 325 μm to about 525 μm; from about 325 μm to about 500 μm; from about 325 μm to about 475 μm; from about 325 μm to about 450 μm; from about 325 μm to about 425 μm; from about 325 μm to about 400 μm; from about 325 μm to about 375 μm; from about 325 μm to about 350 μm; from about 350 μm to about 600 μm; from about 350 μm to about 575 μm; from about 350 μm to about 550 μm; from about 350 μm to about 525 μm; from about 350 μm to about 500 μm; from about 350 μm to about 475 μm; from about 350 μm to about 450 μm; from about 350 μm to about 425 μm; from about 350 μm to about 400 μm; from about 350 μm to about 375 μm; from about 375 μm to about 600 μm; from about 375 μm to about 575 μm; from about 375 μm to about 550 μm; from about 375 μm to about 525 μm; from about 375 μm to about 500 μm; from about 375 μm to about 475 μm; from about 375 μm to about 450 μm; from about 375 μm to about 425 μm; from about 375 μm to about 400 μm; from about 400 μm to about 600 μm; from about 400 μm to about 575 μm; from about 400 μm to about 550 μm; from about 400 μm to about 525 μm; from about 400 μm to about 500 μm; from about 400 μm to about 475 μm; from about 400 μm to about 450 μm; from about 400 μm to about 425 μm; from about 425 μm to about 600 μm; from about 425 μm to about 575 μm; from about 425 μm to about 550 μm; from about 425 μm to about 525 μm; from about 425 μm to about 500 μm; from about 425 μm to about 475 μm; from about 425 μm to about 450 μm; from about 450 μm to about 600 μm; from about 450 μm to about 575 μm; from about 450 μm to about 550 μm; from about 450 μm to about 525 μm; from about 450 μm to about 500 μm; from about 450 μm to about 475 μm; from about 475 μm to about 600 μm; from about 475 μm to about 575 μm; from about 475 μm to about 550 μm; from about 475 μm to about 525 μm; from about 450 μm to about 500 μm; from about 450 μm to about 475 μm; from about 500 μm to about 600 μm; from about 500 μm to about 575 μm; from about 500 μm to about 550 μm; from about 500 μm to about 525 μm; from about 550 μm to about 600 μm; from about 550 μm to about 575 μm; or from about 575 μm to about 600 μm. In other embodiments, the crystalline form is Form A having a D[V,0.90] of less than 600 μm, less than 575 μm, less than 550 μm, less than 525 μm, less than 500 μm, less than 475 μm, less than 450 μm, less than 425 μm, less than 400 μm, less than 375 μm, less than 350 μm, less than 325 μm, less than 300 μm, less than 275 μm, less than 250 μm, less than 225 μm, less than 200 μm, less than 175 μm; less than 150 μm; less than 125 μm; less than 100 μm; less than 75 μm; or less than 50 μm.

In other embodiments, the crystalline form is Form A having a D[4,3] of from about 5 μm to about 200 μm; from about 5 μm to about 175 μm; from about 5 μm to about 150 μm; from about 5 μm to about 125 μm; from about 5 μm to about 100 μm; from about 5 μm to about 75 μm; from about 5 μm to about 50 μm; from about 5 μm to about 40 μm; from about 5 μm to about 25 μm; from about 10 μm to about 200 μm; from about 10 μm to about 175 μm; from about 10 μm to about 150 μm; from about 10 μm to about 125 μm; from about 10 μm to about 100 μm; from about 10 μm to about 75 μm; from about from about 10 μm to about 50 μm; from about 10 μm to about 40 μm; from about 10 μm to about 25 μm; from about 15 μm to about 200 μm; from about 15 μm to about 175 μm; from about 15 μm to about 150 μm; from about 15 μm to about 125 μm; from about 15 μm to about 100 μm; from about 15 μm to about 75 μm; from about 15 μm to about 50 μm; from about 15 μm to about 40 μm; from about 15 μm to about 25 μm; from about 20 μm to about 200 μm; from about 20 μm to about 175 μm; from about 20 μm to about 150 μm; from about 20 μm to about 125 μm; from about 20 μm to about 100 μm; from about 20 μm to about 75 μm; from about 20 μm to about 50 μm; from about 25 μm to about 200 μm; from about 25 μm to about 175 μm; from about 25 μm to about 150 μm; from about 25 μm to about 125 μm; from about 25 μm to about 100 μm; from about 25 μm to about 75 μm; from about 25 μm to about 50 μm; from about 25 μm to about 40 μm; from about 50 μm to about 200 μm; from about 50 μm to about 175 μm; from about 50 μm to about 150 μm; from about 50 μm to about 125 μm; from about 50 μm to about 100 μm; from about 50 μm to about 75 μm; from about 75 μm to about 200 μm; from about 75 μm to about 175 μm; from about 75 μm to about 150 μm; from about 75 μm to about 125 μm; from about 75 μm to about 100 μm; from about 100 μm to about 200 μm; from about 100 μm to about 175 μm; from about 100 μm to about 150 μm; from about 100 μm to about 125 μm; from about 125 μm to about 200 μm; from about 125 μm to about 175 μm; from about 125 μm to about 150 μm; from about 150 μm to about 200 μm; from about 150 μm to about 175 μm; or from about 175 μm to about 200 μm. In other embodiments, the crystalline form is Form A having a D[4,3] of less than 200 μm; less than 175 μm; less than 150 μm; less than 125 μm; less than 100 μm; less than 75 μm; 50 μm; less than 40 μm; less than 30 μm; or less than 25 μm.

A hydrobromide salt form of Compound 1 can be prepared based on the synthetic schemes set forth in U.S. Pat. No. 7,795,447, which is incorporated herein by reference in its entirety. In some embodiments, the particular crystalline or amorphous form of hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having the desired particle size is the product of the synthesis. In other embodiments, the particular crystalline or amorphous hydrobromide salt (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide having the desired particle size is prepared using further processing steps following synthesis. Examples of such processing steps include, but are not limited to, recrystallization and milling, such as jet milling.

In some embodiments, the particle size is determined by laser diffraction (e.g., Sympatec Helos and QicPic) at 3.0 bar dispersion pressure.

Particle sizes for the crystalline materials may be assessed using laser diffraction methods. Laser diffraction is recognized by standards and guidance agencies including ISO and ASTM and is widely used to determine particle size distributions. In conducting the assessment, the sample is passed through a laser beam which results in laser light scattered at a range of angles. Detectors placed at fixed angles measure the intensity of light scattered at that position. A mathematical model (Mie or Fraunhoffer Theory) is then applied to generate a particle size distribution.

The particle size was analyzed using the laser diffraction (or small angle light scattering) technique by dispersing the dry sample powder with compressed air. Specifically, the particle size distribution was analyzed using the Sympatec HELOS RODOS system equipped with a Vibri dry powder feeder. The powder sample was dispersed with a dispersion pressure of 0.5 bar. In some instances, an Aspiros microdosing device was used, and the powder sample was dispersed with a dispersion pressure of 0.2 bar. A suitable lens was selected to cover the particle size range of each sample.

In particle size determinations, the median value is defined as the value where half of the population resides above this point, and half resides below this point. For particle size distributions the median is called the D50. The D50 is the size in microns that splits the distribution with half above and half below this diameter. The expression Dv50 or D[v,0.5] is sometimes used for the median of a volume distribution.

The mode is the peak of a frequency distribution. A particle distribution may include more than one mode, e.g., where the particles exist as primary particles and agglomerations.

The span is sometimes used as a measurement of distribution width and is defined as the ratio of (D[v,0.9]−D[v,0.1])/D[v,0.5] or (D90−D10)/D50.

The distribution width may also be characterized by citing one, two or preferably three values, typically some combination of the D10, D50, and D90. The D50, the median, has been defined above as the diameter where half of the population lies below this value. Similarly, 90 percent of the distribution lies below the D90, and 10 percent of the population lies below the D10.

The term D[4,3] refers to the volume mean or mass moment mean. Laser diffraction results are reported on a volume basis and the volume mean can be used to define the central point of the distribution. The D[4,3] value is sensitive to the presence of large particles in the distribution.

IV. Pharmaceutical Compositions

Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to subjects via the oral, parenteral (such as subcutaneous, intravenous, intramuscular, intrasternal and infusion techniques), rectal, intranasal, topical or transdermal (e.g., through the use of a patch) routes. In one embodiment, crystalline Form A of the compound of Formula (I) may be administered to subjects via the oral, parenteral (such as subcutaneous, intravenous, intramuscular, intrasternal and infusion techniques), rectal, intranasal, topical or transdermal (e.g., through the use of a patch) routes.

In one embodiment, the pharmaceutical composition comprises crystalline Form A of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I). In one embodiment, the pharmaceutical composition is an oral tablet comprising one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) and a pharmaceutically acceptable carrier. In one embodiment, the tablet comprises about 25 mg to about 400 mg of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II). In one embodiment, the tablet comprises about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 225 mg, about 250 mg, about 275 mg, about 300 mg, about 325 mg, about 350 mg, about 375 mg, or about 400 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide as one or more of Forms A-N or amorphous. In one embodiment, the tablet comprises about 50 mg of the hydrobromide salt of (S)-2-(((S)-6,8-difluoro-1,2,3,4-tetrahydronaphthalen-2-yl)amino)-N-(1-(2-methy-1-(neopentylamino) propan-2-yl)-1H-imidazol-4-yl)pentanamide of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II). In one embodiment, the tablet comprises about 100 mg of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II). In one embodiment, the tablet comprises about 150 mg of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II).

For oral administration, known carriers can be included in the pharmaceutical composition. For example, microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia, can be included in a tablet. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing Compound 1 can be prepared in either sesame or peanut oil, in aqueous propylene glycol, or in sterile water or saline. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

V. Methods of Treatment

Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be used to modulate or inhibit the Notch signaling pathway in organisms, including humans. Notch signaling is frequently elevated in a variety of human tumors (including, but not limited to breast, prostate, pancreas and T-cell acute lymphoblastic leukemia).

Accordingly, Forms A-N and amorphous form of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat a subject with tumors or cancer, including, but not limited to desmoid tumors, multiple myeloma, adenoid cystic carcinoma, and T-cell acute lymphoblastic leukemia. In one embodiment, crystalline Form A of the compound of Formula (I) may be administered to treat a subject with tumors or cancer, including, but not limited to desmoid tumors, multiple myeloma, adenoid cystic carcinoma, and T-cell acute lymphoblastic leukemia. In one embodiment, crystalline Form A of the compound of Formula (I) and a pharmaceutically acceptable carrier may be administered to treat a subject with tumors or cancer, including, but not limited to desmoid tumors, multiple myeloma, adenoid cystic carcinoma, and T-cell acute lymphoblastic leukemia. In one embodiment, Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat tumors, including desmoid tumors. In one embodiment, Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat a cancer having a mutation in a Notch pathway gene. In one embodiment, Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat multiple myeloma. Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat adenoid cystic carcinoma. Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) may be administered to treat T-cell acute lymphoblastic leukemia.

In one embodiment, one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) is administered in doses ranging from about 0.1 mg to about 1000 mg per day. In one embodiment, a subject is administered about 50 mg to about 500 mg of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) daily. In another embodiment, a subject is administered about 100 mg to about 400 mg of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) daily. In another embodiment, a subject is administered about 100 mg, about 125 mg, about 150 mg, about 175 mg, about 200 mg, about 225 mg, about 250 mg, about 275 mg, about 300 mg, about 325 mg, about 350 mg, about 375 mg, or about 400 mg daily of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II). The total daily dose can be provided as single or divided doses (i.e., 1, 2, 3, or 4 doses per day). In one embodiment, the total daily dose is provided as two doses. For example, a 300 mg or 200 mg total daily dose can be administered to a subject as two separate 150 mg or 100 mg doses, respectively. In one embodiment, three tablets comprising 50 mg of one or more of Forms A-N and amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) twice daily or 200 mg daily dose can be administered to a subject as two tablets comprising 50 mg of one or more of Forms A-N and amorphous Compound 1 of Formula (I) or (II) twice daily.

In one aspect, the present disclosure relates to a use of one or more of Forms A-N or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) discussed above for treating tumors or cancer. In one embodiment, the present disclosure relates to a use of crystalline Form A of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) for treating tumors or cancer. In one embodiment, the present disclosure relates to the pharmaceutical composition discussed above for treating tumors or cancer. In one embodiment, the use is for treating desmoid tumors. In one embodiment, the use is for treating cancer selected from the group consisting of multiple myeloma, a cancer having a mutation in a Notch pathway gene, adenoid cystic carcinoma, and T-cell acute lymphoblastic leukemia.

In one aspect, the present disclosure relates to one or more of Forms A-N or amorphous form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) or (II) discussed above for use in a method for treatment of tumors or cancer. In one embodiment, the present disclosure relates to crystalline Form A of the hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide of Formula (I) for use in a method for treatment of tumors or cancer. In one embodiment, the present disclosure relates to the pharmaceutical composition discussed above for use in a method for treatment of tumors or cancer. In one embodiment, the use is for treating desmoid tumors. In one embodiment, the use is for treating cancer selected from the group consisting of multiple myeloma, a cancer having a mutation in a Notch pathway gene, adenoid cystic carcinoma, and T-cell acute lymphoblastic leukemia.

EXAMPLES

A. Abbreviations and Acronyms

| | |
|---|---|
| NMR | Nuclear Magnetic Resonance Spectroscopy |
| XRPD | X-ray Powder Diffraction |
| PLM | Polarized Light Microscopy |
| TGA | Thermogravimetric Analysis |
| DSC | Differential Scanning Calorimetry |
| TG-IR | Thermogravimetric Infrared analysis |
| FE | Fast Evaporation |
| SE | Slow Evaporation |
| S/AS | Solvent/Anti-solvent |
| CP | Crash Precipitation |
| LLD | Liquid Liquid Diffusion |
| LVD | Liquid Vapor Diffusion |
| SC | Slow Cooling |
| FC | Fast Cooling |
| CC | Crash Cooling |
| LIMS | Laboratory Information Management System |
| B/E | Birefringence/Extinction |
| RT | Room/ambient Temperature |
| RH | Relative Humidity |
| VO | Vacuum Oven |
| ACN | Acetonitrile |
| CHCl3 | Chloroform |
| DCM | Dichloromethane |
| DCE | Dichloroethane |
| DEE | Diethyl ether |
| DMA | N,N-dimethylacetamide |
| DMF | N,N-dimethylformamide |
| DMSO | Dimethyl sulfoxide |
| EtOAc | Ethyl acetate |
| EtOH | Ethanol |
| H2O | Water |
| HFIPA | Hexafluoroisopropanol |
| IPA | Isopropanol |
| IpOAc | Isopropyl acetate |
| MCH | Methyl cyclohexane |
| MeOH | Methanol |
| MEK | Methyl ethyl ketone |
| MIBK | Methyl-iso-butyl ketone |
| MTBE | Methyl-tert-butyl ether |
| NMP | N-methyl-2-pyrrolidone |
| PG | Propylene glycol |
| TFE | Trifluroethanol |
| THF | Tetrahydrofuran |

B. Experimental Methods

Example 1: Approximate Kinetic Solubility

Weighed samples of material were treated with aliquots of specified solvents at ambient temperature. Samples were typically sonicated between additions to facilitate dissolution. Complete dissolution was observed through visual inspection. Solubility was calculated based on the total amount of solvent added to achieve complete dissolution and may be greater than the value reported due to incremental solvent addition and the inherent kinetics of dissolution. If dissolution was not observed, values are reported as "less than". If dissolution was observed upon the first addition of solvent, values are reported as "greater than". Table 1 shows kinetic solubility of dihydrobromide salt of (s)-2-(((s)-6,8-difluoro-1,2,3,4-tetrahydronaphthalen-2-yl)amino)-n-(1-(2-methyl-1-(neopentylamino)propan-2-yl)-1h-imidazol-4-yl)pentanamide.

TABLE 1

| Solvent | Solubility Estimate (a) (mg/mL) |
|---|---|
| Acetone | <1 |
| Acetone/CHCl3 50/50 | <1 |
| ACN | <1 |
| ACN/CHCl3 50/50 | <1 |
| ACN/EtOAc 50/50 | <1 |
| Chloroform | <1 |
| DCE | <1 |
| Dioxane | '<1 |
| DMA | 8 |
| DMF | 18 |
| DMF/ACN 30/70 | <1 |
| DMF/ACN 60/40 | 3 |
| DMF/EtOAc 50/50 | <1 |
| DMF/IPA 60/40 | 5 |
| DMF/MIBK 80/20 | 4 |
| DMSO | 63 |
| DMSO/MTBE 10/90 | <1 |
| Ethylene Glycol | 7 |
| EtOAc | <1 |
| EtOH | <1 |
| EtOH/DCM 50/50 | <1 |
| Heptane/CHCl3 30/70 | <1 |
| MEK/DMF (b) 40/60 | 2 |
| MeOH | 19 |
| MeOH/Acetone 50/50 | 6 |
| MeOH/CHCl3 50/50 | 13 |
| MeOH/EtOAc 50/50 | 2 |
| MeOH/MTBE 80/20 | 7 |
| NMP | 10 |
| NMP/Acetone 85/15 | 7 |
| NMP/EtOAc 57/43 | 1 |
| PG (b) | 2 |
| TFE (anhydrous) | 10 |
| TFE/MEK 70/30 | 2 |
| THF (b) | <1 |
| THF/CHCl3 50/50 | 1 |
| THF/CHCl3 25/75 | <1 |
| THF/CHCl3 (b) 85/15 | <1 |
| Toluene | <1 |
| Water | 7 |
| Acetone/H2O 30/70 | 14 |
| ACN/H2O 50/50 | 36 |
| Dioxane/H2O (b) 50/50 | 19 |
| DMF/H2O 50/50 | 24 |
| DMF/H2O 30/70 | 17 |
| EtOH/H2O 40/60 | 10 |
| IPA/H2O 50/50 | 15 |
| MeOH/H2O 20/80 | 9 |
| THF/H2O 80/20 | 24 |
| THF/H2O 90/10 | 4 |

(a) Solubility estimated using solvent addition method via visual assessment of samples. Values are rounded to nearest whole number and reported as "<" if dissolution was not observed.
(b) non-cGMP samples.

Example 2: Stable Form and Hydrate Screen

Method a: Trituration Experiments

Samples of dihydrobromide salt of (s)-2-(((s)-6,8-difluoro-1,2,3,4-tetrahydronaphthalen-2-yl)amino)-n-(1-(2-methyl-1-(neopentylamino)propan-2-yl)-1h-imidazol-4-yl)pentanamide were triturated at ambient or set temperature in specified solvent systems. After approximately 24 hours, solids were isolated by centrifugation using eppendorf centrifuge tubes equipped with a 0.45 µm nylon filter. The agitation was then continued in fresh solvents for a total of ~1 and 3 weeks, after which the solids were isolated as described above, observed under polarized light and analyzed by)(RFD.

Method b: Equilibrium Solubility Testing

Equilibrium solubility of solids isolated were determined gravimetrically as follows. Measured aliquots of mother liquor solutions from the 3-week slurries were place in pre-weighed aluminum TGA pans. Subsequently, solvents were evaporated under ambient conditions or using vacuum. Remaining solids were weighed.

Table 2 shows results of stable form and hydrate screen.

TABLE 2

| Solvent system, conditions (a) | Observations | XRPD Results | Solubility (mg/mL) (b) |
|---|---|---|---|
| DMA (anhydrous) 1 week | Unknown morphology; B/E | Form A | — |
| DMA (anhydrous) 3 weeks | Unknown morphology; B/E | Form A | 27 |
| DMF/ACN (65/35) 1 week | Unknown morphology; B/E | Form A | — |
| DMF/ACN (65/35) 3 weeks | Unknown morphology; B/E | Form A | 10 |
| DMF/IPA (60/40) 1 week | Unknown morphology; B/E | Form A | — |
| DMF/IPA (60/40) 3 weeks | Unknown morphology; B/E | Form A | 13 |
| DMF/MIBK (85/15) 1 week | Unknown morphology; B/E | Form A | — |
| DMF/MIBK (85/15) 3 weeks | Unknown morphology; B/E | Form A | 19 |
| DMSO/MTBE (anhydrous) (30/70) 1 day (c) | Unknown morphology; B/E | Form A | — |
| MEK/DMF (20/80) 1 week | Unknown morphology; B/E | Form A | — |
| MEK/DMF (20/80) 3 weeks | Unknown morphology; B/E | Form A | 17 |
| MeOH (anhydrous) 2-8° C. (d) 1 week | Unknown morphology, small particles; B/E | Form A | — |
| MeOH (anhydrous) 2-8° C. (d) 3 weeks | Unknown morphology + some needle-like; B/E | Form A | 13 |
| MeOH/Acetone (anhydrous) (50/50) 1 week | Unknown morphology, small particles; B/E | Form A | — |
| MeOH/Acetone (anhydrous) (50/50) 3 weeks | Unknown morphology, extremely small; B/E | Form A | 7 |
| MeOH/CHCl3 (anhydrous) (40/60) 1 week | Unknown morphology; B/E | Form A | — |
| MeOH/CHCl3 (anhydrous) (40/60) 3 weeks | Unknown morphology + some needle-like; B/E | Form A | 22 |
| MeOH/EtOAc (anhydrous) (70/30) 1 week | Unknown morphology, small particles; B/E | Form A | — |
| MeOH/EtOAc (anhydrous) (70/30) 3 weeks | Unknown morphology; B/E | Form A | 6 |
| MeOH/MTBE (anhydrous) (80/20) 1 week | Unknown morphology, small particles; B/E | Form A | — |
| MeOH/MTBE (anhydrous) (80/20) 3 weeks | Unknown morphology + some needle-like; B/E | Form A | 12 |
| NMP (anhydrous) 1 week | Unknown morphology; B/E | Form A | — |
| NMP (anhydrous) 3 weeks | Unknown morphology, very small; B/E | Form A | 50 |
| NMP/Acetone (anhydrous) (85/15) 1 week | Unknown morphology, very small particles; B/E | Form A | — |
| NMP/Acetone (anhydrous) (85/15) 3 weeks | Unknown morphology; B/E | Form A | 36 |
| NMP/EtOAc (anhydrous) (80/20) 1 week | Unknown morphology + small needles; B/E | Form A | — |
| NMP/EtOAc (anhydrous) (80/20) 3 weeks | Unknown morphology; B/E | Form A | 25 |
| PG 1 week | Unknown morphology; B/E | Form A | — |
| PG 3 weeks | Unknown morphology, extremely small; B/E | Form A | 8 |
| TFE (anhydrous) 3 weeks | Unknown morphology; B/E | Form A | — |
| TFE/MEK (anhydrous) (85/15) 1 week | Unknown morphology; B/E | Form A | — |
| TFE/MEK (anhydrous) (85/15) 3 weeks | Unknown morphology, extremely small; B/E | Form A | |
| $H_2O$ 1 week | Unknown morphology; B/E | Form A | — |
| $H_2O$ 3 weeks | Very small needles; B/E | Form A | 14 |
| Acetone/$H_2O$ (50/50) 1 week | Unknown morphology, very small particles; B/E | Form A | — |
| Acetone/$H_2O$ (50/50) 3 weeks | Unknown morphology, extremely small; B/E | Form A | 43 |
| Dioxane/$H_2O$ (70/30) 1 week | Unknown morphology, small particles; B/E | Form A | — |
| Dioxane/$H_2O$ (70/30) 3 weeks | Unknown morphology + some needles; B/E | Form A | 24 |
| IPA/$H_2O$ (60/40) 1 week | Unknown morphology, very small particles; B/E | Form A | — |
| IPA/$H_2O$ (60/40) 3 weeks | Unknown morphology, extremely small; B/E | Form A | 26 |
| EtOH/$H_2O$ (60/40) 1 week | Unknown morphology; B/E | Form A | — |
| EtOH/$H_2O$ (60/40) 3 weeks | Extremely small needles; B/E | Form A | 36 |
| EtOH/$H_2O$ (60/40) 2-8° C. (d) 1 week | Unknown morphology, small particles; B/E | Form A | — |

TABLE 2-continued

| Solvent system, conditions (a) | Observations | XRPD Results | Solubility (mg/mL) (b) |
|---|---|---|---|
| EtOH/H$_2$O (60/40) 2-8° C. (c) 3 weeks | Unknown morphology, extremely small; B/E | Form A | 33 |
| MeOH/H$_2$O (20/80) 1 week | Unknown morphology, small particles; B/E | Form A | — |
| MeOH/H$_2$O (20/80) 3 weeks | Extremely small needles; B/E | Form A | 17 |
| THF/H$_2$O (85/15) 1 week | Unknown morphology; B/E | Form A | — |
| THF/H$_2$O (85/15) 3 weeks | Unknown morphology, extremely small; B/E | Form A | 25 |

(a) Experiments were conducted for a total of ~1 week and ~3 weeks, both with solvent replacement after ~1 day of slurrying. Solvent ratios (v/v) and duration of experiments are approximate. Experiments were performed at ambient conditions unless otherwise specified,
(b) Solubility determined gravimetrically.
(c) After the initial solvent exchange, there was an insufficient amount of solids to use for further slurry.
(d) Conducted in a cold room.
(e) non-cGMP samples.

Example 3: Polymorph Screen

Dihydrobromide salt of (s)-2-(((s)-6,8-difluoro-1,2,3,4-tetrahydronaphthalen-2-yl)amino)-n-(1-(2-methyl-1-(neopentylamino)propan-2-yl)-1h-imidazol-4-yl)pentanamide, unless noted otherwise, was used as the starting material. Materials produced in the study were utilized for selected experiments.

Starting materials were subjected to crystallization techniques, which are summarized below. Solids were typically isolated by vacuum filtration, observed under polarized light and analyzed by XRPD.

Method a: Grinding Experiments

Solids were combined with small amounts of solvent and transferred to an agate milling container. An agate ball was added and the container attached to a Retsch mill. The sample was typically milled for either one cycle of twenty minutes at 30 Hz, or repacked and the cycle repeated for an additional 20 minutes.

Method b: Slurry Experiments

Solids were suspended in specified solvents. The suspensions were then agitated at ambient or set temperature. After a given amount of time solids were isolated.

Method c: Solvent/Anti-Solvent Precipitation

Solutions of starting material were prepared at ambient or elevated temperature and filtered using 0.2 μm nylon filters. They were then mixed with appropriate anti-solvents at elevated temperature. If no solids were observed, the samples were either cooled to ambient or sub-ambient temperatures or other crystallization techniques applied.

Method d: Crash Precipitation

Solutions of starting material were prepared at elevated temperature in specified solvents and hot-filtered through 0.2 μm nylon filters into appropriate anti-solvents pre-cooled on a dry ice/acetone or water/ice bath. If solids precipitated, they were immediately isolated by vacuum filtration while still cold. If the solution remained clear, the sample was either kept at sub-ambient temperatures or further crystallization techniques were applied.

Method e: Cooling Experiments

Solutions of starting material were prepared in specified solvents at elevated temperature using a hot plate for heating. These were typically hot-filtered through a 0.2 μm nylon filter into warm receiving vials. The vials were either quickly transferred into a sub-ambient temperature bath (typically dry ice/acetone) for crash cooling (CC), removed from the hot place for fast cooling (FC) or the heat was turned off to allow for slow cooling (SC). If solids precipitated, they were isolated cold by vacuum filtration. If the solution remained clear, the sample was either kept at sub-ambient temperatures or further crystallization techniques were applied.

Method f: Evaporation Experiments

Solutions of starting material were allowed to partially evaporate or evaporate to dryness at ambient or elevated temperature from open vials for fast evaporation (FE) or from vials covered with aluminum foil with pin holes for slow evaporation (SE). Prior to evaporation, solutions were filtered at ambient or elevated temperature using 0.2 μm nylon filters.

Method g: Liquid-Vapor Diffusion Experiments

Solutions of starting material were prepared at ambient temperature and filtered through 0.2 μm nylon filters into receiving vials. The open vials were then placed into secondary containers with appropriate anti-solvents. The containers were sealed and left undisturbed at ambient conditions.

Method h: Vapor Stress Experiments

Solids of starting material were transferred to vials which were placed uncapped into secondary containers with appropriate anti-solvents. The secondary containers were sealed and left undisturbed at ambient or sub-ambient conditions.

Method i: Low Relative Humidity Stress Experiments

Solids of starting material were transferred to a vial which was placed, uncapped, into a RH jar containing P2O5. It was kept at ambient temperature for a specified duration.

Method j: Drying Experiments

Solids of starting material were dried at ambient or under reduced pressure at a set temperature for a specified duration.

Table 3 summarizes the polymorph screen results for dihydrobromide salt of (s)-2-(((s)-6,8-difluoro-1,2,3,4-tetrahydronaphthalen-2-yl)amino)-n-(1-(2-methyl-1-(neopentylamino) propan-2-yl)-1h-imidazol-4-yl)pentanamide.

TABLE 3

| Solvent system | Conditions (a) | Observations | XRPD Results |
| --- | --- | --- | --- |
| ACN | Slurry, 45° C., 2 days | Unknown morphology; B/E | Form A |
| DCE | Slurry, 45° C., 2 days | Unknown morphology; B/E | Form A |
| DMA/DMSO (89/11) | FC attempt from 44° C. to RT (clear). Transferred to freezer, 13 days. Sonicated, FE followed by SE and then by FE at RT (small needles present in solution). Transferred back to freezer, 13 days. | Insufficient amount of solids | — |
| DMF | FC attempt from 44° C. to RT (clear). Transferred to freezer, 13 days. Sonicated, FE followed by SE and then by FE at RT (solids). Transferred back to freezer, 13 days. | Unknown morphology; B/E | Form A |
| DMF/MIBK (80/20) | SC attempt, 45° C. to RT over 2 days. Transferred to freezer, 8 days. Sonicated, FE followed by SE and then by FE at RT (small needles present in solution). Transferred back to freezer, 13 days. | Insufficient amount of solids | — |
| DMSO/MTBE (30/70) | Mother liquor; FE | Unknown morphology; B/E | Form A |
| EtOAc | Slurry, 45° C., 2 days | Unknown morphology; B/E | Form A |
| H$_2$O | Slurry, RT, 4 days | Unknown morphology; B/E | Form A |
| HFIPA | SE | Unknown morphology; B/E | Form F |
|  | SE | Unknown morphology + small needles; B/E | Form J |
| MeOH (anhydrous) 2-8° C. (b) | Mother liquor; FE | B/E particles within a transparent matrix | Form B, disordered |
| MeOH/Acetone (anhydrous) (50/50) | Mother liquor; FE | Opaque particles; no B/E | Form C |
| MeOH/Acetone (50/50) | FE, 40° C. | Unknown morphology + small needles; B/E | Form B, disordered |
|  | FE, RT | Unknown morphology + translucent particles; B/E | Form B, disordered |
| MeOH/ACN | S/AS attempt, AS addition at 45° C. (clear); volume reduction by FE at 45° C. (gel-like solids). Added AS at 45° C., transferred to freezer, ~1 month. | Unknown morphology; B/E | Form A, disordered |
| MeOH/CHCl3 (anhydrous) (40/60) | Mother liquor; FE | Unknown morphology; B/E | Disordered, with peaks of Form A |
| MeOH/EtOAc (anhydrous) (70/30) | Mother liquor; FE | Glass | — |
| MeOH/MTBE | CP attempt 45° C./sub-RT, ice bath (viscous solids). Ice bath, 2 hours, then kept at RT, 20 days. | Unknown morphology + small needles; B/E | Form A |
| — | From viscous solids of 6094-34-04. Added heptane to viscous solids, FE at RT. | Unknown morphology + glassy particles; B/E | Form B, disordered |
| NMP/EtOAc (70/30) | SC attempt, 45° C. to RT over 2 days. Transferred to freezer, 8 days. Sonicated, then FE at RT. | No solids | — |
| TFE/MEK (anhydrous) (85/15) | Mother liquor; FE | Unknown morphology + glass; B/E | Form A |
| TFE/MEK (anhydrous) | CP attempt 45° C./sub-RT (ice bath). Transferred to freezer, 7 days. Isolated solids while cold. | Unknown morphology; B/E | Form A |
| Acetone/H$_2$O (50/50) | Mother liquor; FE | Glass + some B/E particles | Form B, disordered |

TABLE 3-continued

| Solvent system | Conditions (a) | Observations | XRPD Results |
|---|---|---|---|
| DMSO/H$_2$O (4/96) | CC attempt from 44° C. to sub-RT (ice/H20 bath, clear). Kept in refrigerator, 13 days (clear). Sonicated, FE at RT (some solids). Transferred back to refrigerator, ~5 months. | Insufficient amount of solids | — |
| Dioxane/H$_2$O (70/30) | Mother liquor; FE | Unknown morphology + needles; B/E | Form A, possibly with X-ray amorphous content |
| Dioxane/H$_2$O (50/50) | FE, 45° C. | Unknown morphology + small, dendritic needles; B/E | Form B, disordered |
| | Lyophilization, −35° C. | — | X-ray amorphous |
| | Lyophilization, −50° C. | — | X-ray amorphous |
| IPA/H$_2$O (60/40) | Mother liquor; FE | Rosettes within a glassy matrix + unknown morphology; B/E | Form A, possibly with X-ray amorphous content |
| IPA/H$_2$O (50/50) | FE, 45° C. | Unknown morphology; B/E | Form B, disordered |
| EtOH/H$_2$O (60/40) | Mother liquor; FE | Needles + unknown morphology; B/E | Disordered, with peaks of Form A |
| EtOH/H$_2$O (60/40) | FE, 45° C. | Unknown morphology; B/E | Form D + peaks |
| EtOH/H$_2$O (60/40) 2-8° C. (b) | Mother liquor; FE | Unknown morphology + needles; B/E | Form B, disordered |
| MeOH/H$_2$O (20/80) | Mother liquor; FE | Unknown morphology + glass; B/E | Form B, disordered |
| THF/H$_2$O (85/15) | Mother liquor; FE | Unknown morphology; some B/E | Form B, disordered |

(a) Solvent ratios (v/v), temperature, and duration of experiments are approximate. Refrigerator and cold room temperature: 2-8° C.; freezer temperature: between −10° C. and −25° C.
(b) The mother liquor was obtained from the slurry at 2-8° C. The evaporation was at ambient temperature.
(c) non-cGMP samples.

Table 4 summarizes the polymorph screen results for dihydrobromide salt of (s)-2-(((s)-6,8-difluoro-1,2,3,4-tetrahydronaphthalen-2-yl)amino)-n-(1-(2-methyl-1-(neopentylamino) propan-2-yl)-1h-imidazol-4-yl)pentanamide starting from X-ray amorphous material.

TABLE 4

| Solvent system | Conditions (b) | Observations | XRPD Results |
|---|---|---|---|
| CHCl3/Heptane 43/57 (anhydrous) | Stirring, CHCl3, RT, 3 days (viscous solids). Added heptane at RT (small, fine solids); slurry, 1 day. | Unknown morphology, extremely small; B/E | Form E, crystalline with disorder |
| EtOH | Slurry, RT, 3 days | Unknown morphology, very small; B/E | Form A |
| MEK/Heptane 62/38 (anhydrous) | Stirring, MEK, RT, 3 days (viscous solids). Added heptane at RT (small, fine solids + some viscous); slurry, 1 day. | Unknown morphology + some opaque particles; B/E | Form G, disordered |
| Toluene | Vapor stress, RT, 6 days | Opaque particles + a few particles with B/E | X-ray amorphous |
| DCM | Vapor stress, freezer, 6 days | Unknown morphology; B/E Solvent present. | Form H, disordered, possibly contains Form A |
| MeOH/Acetone (anhydrous) | LVD, RT | Unknown morphology + needles; B/E | Form A |

TABLE 4-continued

| Solvent system | Conditions (b) | Observations | XRPD Results |
|---|---|---|---|
| Dioxane (anhydrous) | Grinding; 1 cycle, 30 Hz, 20 minutes | Unknown morphology + some translucent particles; B/E | Form B, disordered, possibly contains Form G |
| IpOAc | Grinding; 1 cycle, 30 Hz, 20 minutes | Unknown morphology + small needles; B/E | Form A, disordered |
| DCE | FE, 30° C., then cooled to RT and transferred to freezer | Unknown morphology; No suitable crystals for structure determination | Disordered |
| Acetone/MeOH/MCH 14/17/69 | S/AS, added AS at 30° C. Kept at 30° C., 3-4 hours, then cooled to RT. | Very thin needles; B/E | Form A |
| CHCl3 | Saturated solution, kept at RT, 1 day. Transferred to freezer, ~5 months. | Insufficient amount of solids | — |

(a) All samples generated from LIMS 386797 are non-cGMP.
(b) Solvent ratios (v/v), temperature, and duration of experiments are approximate. Refrigerator and cold room temperature: 2-8° C.; freezer temperature: between −10° C. and −25° C.

Example 4: Preparation of X-ray Amorphous Material

A solution of starting material was prepared in dioxane/water (50/50) at ambient temperature and filtered into a round bottom flask. The flask was submerged into a dry ice/acetone bath to freeze the solution. Once frozen, it was attached to a lyophilizer at approximately −50° C. for two days.

Example 5: Preparation of Selected Materials

Table 5 summarizes the preparation conditions for selected materials.

TABLE 5

| Targeted Material | Solvent System | Conditions (a) | Observations | XRPD Results |
|---|---|---|---|---|
| Form B | MeOH | FE, RT | Unknown morphology; B/E | Form B, disordered |
| | | FE, RT. Stored solids in freezer. | Unknown morphology; B/E | Form B, disordered |
| | | SE, RT. Stored solids in freezer. | — | Analyzed wet. Form D |
| | | From 6094-34-02. Vapor stress, RT. Stored solids in freezer. | Unknown morphology; B/E | Form A |
| | | Prepared saturated solution at 45° C., then SC to RT. Transferred to freezer. | No solids | — |
| | MeOH/Acetone 50/50 | FE, 45° C. Stored solids in freezer. | Unknown morphology, B/E particles encapsulated in solvent | Form D |
| | MeOH/Acetone | Prepared saturated solution in MeOH at 45° C.; added acetone at elevated temperature. SC to RT (cloudy). | Small needles; B/E | Form A |
| | MeOH/HFIPA 60/40 | SE, RT. Stored solids in freezer. | — | Analyzed wet. Form M |
| | Acetone/H2O 50/50 | SE, then FE, RT. SC, 50° C. to RT Transferred to freezer. | Glassy No solids | — — |
| | MeOH/MTBE | LVD, RT. Air-dried solids. | Unknown morphology + glassy; B/E | Form B, disordered |
| Form C | MeOH/Acetone (anhydrous) 50/50 | FE, 45° C. | Unknown morphology; B/E + some opaque particles | Form C |

TABLE 5-continued

| Targeted Material | Solvent System | Conditions (a) | Observations | XRPD Results |
|---|---|---|---|---|
| | MeOH/Acetone (anhydrous) 50/50 | FE, 45° C. Solids stored in freezer. | — | Form C + small peaks |
| | — | From 6141-67-02. VO, RT, 1 day. | — | Form C + small peaks |
| | MeOH/Acetone (anhydrous) 50/50 | Slurry, RT, 1 day; centrifuged solids and FE of mother liquor. Stored solids in freezer. | Unknown morphology, small particles; some B/E | Form C + small peaks |
| Form D | EtOH/H2O | FE, 45° C. | Unknown morphology + small needles; B/E | Form D + peaks, may also contain Form A |
| | 60/40 | FE, 45° C. Stored in freezer | — | Analyzed wet. Disordered, contains Form D |
| | | SC, 45° C. to RT, then FE, RT. | Glass | — |
| | | Slurry, RT | Unknown morphology, small particles; B/E | Form A |
| | MeOH/H2O 35/65 | Slurry, RT | Unknown morphology; B/E | Form A |
| Form E (b) | CHCl3/Heptane (anhydrous) 43/57 | Slurry, RT, 7 days; added heptane, transferred to freezer, 10 days. Added heptane, then SE at ambient. Stored solids in freezer. | Unknown morphology + glassy; some B/E | X-ray amorphous |
| | CHCl3/Heptane (anhydrous) (33/67) | Slurry, CHCl3, RT, 5 days (viscous). Added heptane. Slurry, RT, 7 days. | Unknown morphology; B/E | Form E, improved crystallinity |
| Form H (b) | DCM | Slurry, RT, 7 days; added DCM, transferred to freezer, 10 days, then SE at ambient. Stored solids in freezer. | Unknown morphology; B/E | Form K, disordered |
| | | Vapor stress, freezer, 13 days. | Unknown morphology; B/E | Similar to Form H, disordered |
| Form G (b) | MEK/Heptane (anhydrous) 58/42 | SC from 45° C.; transferred to freezer, 14 days, then SE at ambient. | Viscous | — |
| | MEK/Heptane (anhydrous) (43/57) | Slurry, MEK, RT, 5 days (viscous). Added heptane. Slurry, RT, 7 days. | Unknown morphology + needles; B/E | Form A |
| Form F (b) | HFIPA | SE | Unknown morphology; B/E | Similar to Form F |
| Form J | HFIPA | SE. Stored solids in freezer. | Unknown morphology; B/E | Form L |
| | | Vapor stress | Solids dissolved | — |
| | | From 6141-53-02. SE, RT. Stored solids in freezer. | Unknown morphology; B/E | Form F + peaks; poorly crystalline |
| | | Grinding; 2 cycles, 30 Hz, 20 minutes | Unknown morphology, small particles; B/E | Form A + peaks, decreased crystallinity |

(a) Solvent ratios (v/v), temperature, and duration of experiments are approximate. Refrigerator and cold room temperature: 2-8° C.; freezer temperature: between −10° C. and −25° C.
(b) X-ray amorphous material was used as starting material. Material is non-cGMP.
(c) non-cGMP samples.

Table 6 summarizes the drying conditions for selected materials.

TABLE 6

| Starting Material | Conditions (a) | XRPD Results |
| --- | --- | --- |
| Similar to Form F | VO, 45° C., 1 day | Consistent with Form F |
| Form F | VO, 77° C., 1 day | Consistent with Form F; poorly crystalline |
| Form D | VO, 75° C., 1 day | Consistent with Form D |
|  | Dried on P205, RT, 17 days RH at prep.: 3% RH at run: 43% | Consistent with Form D, selected peaks slightly shifted |
| Form M | Air drying, 1 day | Similar to Form F |
| Form E | 120° C., 8 hours | Disordered, similar to Form B |

(a) Temperature, RH, and duration of experiments are approximate.

Example 6: Interconversion Experiments

Starting materials, except for Form A, were dried in a vacuum oven at 45° C. for approximately 1 day. Saturated solutions of Form A in specified solvent systems were prepared and seeds of the dried materials and of Form A were added. The samples were agitated in sealed vials at ambient temperature for approximately one week.

Table 7 summarizes results for interconversion experiments.

TABLE 7

| Starting Material (a) | Conditions (b) | XRPD Results |
| --- | --- | --- |
| Seeds of Form A, Form D, Form B, Form E, Form F, Form G, Form J | MeOH Slurry, RT, 1 week MEK/DMF 50/50 Slurry, RT, 1 week | Form A Form A |

TABLE 7-continued

| Starting Material (a) | Conditions (b) | XRPD Results |
| --- | --- | --- |
| Seeds of Form A, Form D, Form B, Form C, Form E, Form F, Form G, Form J | EtOH/H2O 60/40 Slurry, RT, 1 week | Form A |

(a) All materials excluding Form A were dried under vacuum at 45° C. for ~1 day prior to the experiments.
(b) Temperature and duration of experiments are approximate.

Example 7: Single Crystals Growth Experiments

Samples of Form A were treated using the following crystallization techniques. In attempts to induce crystallization, seeds of Form A were added in selected experiments.

Method a: Evaporation/Volume Reduction Experiments

Solutions of starting material were allowed to partially evaporate or evaporate to dryness at ambient or elevated temperature from open vials for fast evaporation (FE) or from vials capped loosely or covered with aluminum foil with pin holes for slow evaporation (SE). Prior to evaporation, solutions were filtered at ambient or elevated temperature using a 0.2 μm nylon filter.

Method b: Liquid-Vapor and Liquid-Liquid Diffusion Experiments

Solutions of starting material were prepared in specified solvents at ambient temperature and typically filtered using a 0.2 μm nylon filter. For liquid vapor diffusion (LVD), vials with filtered solutions were placed in secondary containers with appropriate anti-solvents and left undisturbed at ambient or sub-ambient temperature. For liquid-liquid diffusion (LLD), solutions of tested material were carefully brought in contact with specified solvents and left undisturbed at ambient or sub-ambient temperature.

Method c: Cooling Experiments

Solutions of starting material were prepared at elevated temperature using a hot plate for heating. The solutions were then hot filtered using a 0.2 μm nylon filter and left on the heating source and slowly cooled to a set temperature (SC). After a specified duration, they were further cooled to a sub-ambient temperature.

Table 8 summarizes single crystals growth results for Form A

TABLE 8

| Solvent system | Conditions (a) | Observations | XRPD Results |
| --- | --- | --- | --- |
| DMF/DEE | LLD; kept in refrigerator, 6 weeks | No suitable crystals | — |
| DMF/EtOAc | LVD | No suitable crystals; Unknown morphology; B/E | Form A |
| DMF/IPA | LVD, after 15 days transferred to freezer, ~5 months. | No solids | — |
| DMF/MEK | LVD, 5 days | No suitable crystals; Unknown morphology + small needles; B/E | Form A |
| DMF/THF | LVD, after 5 days, transferred to freezer, ~5 months. | No solids | — |
| MeOH/Acetone (64/36) | SE, 45° C., with seeding | No suitable crystals; Unknown morphology, B/E | — |
| MeOH/Acetone (50/50) | SE | No suitable crystals; Small, needle-like particles; B/E | Form B, disordered |

TABLE 8-continued

| Solvent system | Conditions (a) | Observations | XRPD Results |
|---|---|---|---|
| MeOH/CHCl3 (50/50) | SE | Unknown morphology; B/E | Form B, disordered |
| MeOH/Cyclohexane | LLD | No solids | — |
| MeOH/DEE | LLD; kept in refrigerator, 6 weeks | — | — |
| MeOH/Heptane | LLD | — | — |
| MeOH/Heptane | LLD, sub-ambient (freezer) | No solids | — |
| MeOH/MTBE (80/20) | SE | No suitable crystals; Unknown morphology; B/E | Form B, disordered |
| NMP | SC attempt, 45° C. to 30° C.; seeded with Form A; 30° C., 11 days. Transferred to freezer, 16 days. | No solids | — |
|  | FE from elevated temperature (40° C. to 30° C.), then cooled to RT and transferred to freezer. | Needles + small particles, unknown morphology; B/E | Form N, may contain Form C |
| PG | SC, 45° C. to 30° C.; seeded with Form A; 30° C., 11 days, then transferred to freezer, 16 days. | No solids | — |

(a) Solvent ratios (v/v), temperature, and duration of experiments are approximate. Refrigerator and cold room temperature: 2-8° C.; freezer temperature: between −10° C. and −25° C.
(b) non-cGMP samples.

Example 8: X-Ray Powder Diffraction (XRPD)

Method a: Transmission Geometry

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d or 640e) was analyzed to verify the observed position of the Si 111 peak is consistent with the NIST-certified position. A specimen of the sample was sandwiched between 3-μm-thick films and analyzed in transmission geometry. A beamstop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Method b. Reflection Geometry

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d or 640e) was analyzed to verify the observed position of the Si 111 peak is consistent with the NIST-certified position. A specimen of the sample was prepared as a /thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Example 9: Thermogravimetric Analysis (TGA)

TGA analyses were performed using a TA Instruments 2050 or a Discovery thermogravimetric analyzer. Temperature calibration was performed using nickel and Alumel™. Each sample was placed in an aluminum or platinum pan and inserted into the TG furnace. The furnace was heated under a nitrogen purge. The method code on the thermogram is an abbreviation for the start and end temperature as well as the heating rate; e.g., 25-350-10 means "from 25° C. to 350° C., at 10° C./min".

Example 10: Differential Scanning Calorimetry (DSC)

DSC was performed using a TA Instruments Q2000 differential scanning calorimeter. Temperature calibration was performed using NIST-traceable indium metal. The sample was placed into an aluminum DSC pan (TOC), covered with a lid, and the weight was accurately recorded. A weighed aluminum pan configured as the sample pan was placed on the reference side of the cell. The method code on the thermogram is an abbreviation for the start and end temperature as well as the heating rate; e.g., −30-250-10 means "from ~30° C. to 250° C., at 10° C./min".

Example 11: Thermogravimetric-Infrared Spectroscopy (TG-IR)

Thermogravimetric infrared (TG-IR) analysis was performed on a TA Instruments thermogravimetric (TG) analyzer model 2050 interfaced to a Magna-IR 560® Fourier transform infrared (FT-IR) spectrophotometer (Thermo Nicolet) equipped with an Ever-Glo mid/far IR source, a potassium bromide (KBr) beamsplitter, and a mercury cadmium telluride (MCT-A) detector. The FT-IR wavelength verification was performed using polystyrene, and the TG calibration standards were nickel and Alumel™. The sample was placed in a platinum sample pan, and the pan was inserted into the TG furnace. The TG instrument was started first, immediately followed by the FT-IR instrument. The TG instrument was operated under a flow of helium at 90 and 10 cc/min, for the purge and balance, respectively. The furnace was heated under helium at a rate of 20° C./minute to a final temperature of 250° C. IR spectra were collected approximately every 32 seconds for approximately 13 minutes. Each IR spectrum represents 16 co-added scans collected at a spectral resolution of 4 cm$^{-1}$. Volatiles were identified from a search of the High Resolution Nicolet Vapor Phase spectral library. Searches from this library are considered non-cGMP.

Example 12: Polarized Light Microscopy (PLM)

Light microscopy was performed using a Leica DM LP microscope equipped with a SPOT Insight™ color digital camera. Typically, each sample was placed on a glass slide, a cover glass was placed over the sample, and a drop of mineral oil was added to cover the sample by capillarity. Each sample was observed using a 0.8-10.0× objective with crossed polarizers and a first order red compensator.

Example 14: Computational Methods (Indexing)

Successful indexing of an XRPD pattern indicates that the sample is composed primarily of a single crystalline phase. Agreement between allowed peak positions and observed peaks indicates a consistent unit cell determination. Indexing was performed using X'Pert High Score Plus 2.2a (2.2.1) and TRIADS™. No attempts at molecular packing were performed to confirm the tentative indexing solution within the scope of this work.

We claim:

1. A pharmaceutical composition comprising a solid form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide wherein the solid form has a D[V,0.90] particle size of from about 8 to about 100 µm.

2. The pharmaceutical composition of claim 1, wherein the composition comprises about 50 mg of the hydrobromide salt.

3. The pharmaceutical composition of claim 1, wherein the hydrobromide salt has a D[V,0.10] particle size of about 0.5 µm.

4. The pharmaceutical composition of claim 3, wherein the composition comprises about 50 mg of the hydrobromide salt.

5. The pharmaceutical composition of claim 1, wherein the hydrobromide salt has a D[V,0.90] particle size of from about 8 to about 75 µm.

6. The pharmaceutical composition of claim 2, wherein the hydrobromide salt has a D[V,0.90] particle size of from about 8 to about 75 µm.

7. A pharmaceutical composition comprising a solid form of a hydrobromide salt of (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide wherein the solid form has a D[V,0.10] particle size between about 0.5 µm and about 15 µm, a D[V,0.50] particle size between about 2 µm and about 30 µm, a D[V,0.90] particle size between about 8 µm and about 600 µm, or a D[4,3] particle size of about 5 µm to about 200 µm.

8. The pharmaceutical composition of claim 7, having two or more of: a D[V,0.10] particle size for the solid form between about 0.5 µm and about 15 µm, a D[V,0.50] particle size for the solid form between about 2 µm and about 30 µm, a D[V,0.90] particle size for the solid form between about 8 µm and about 600 µm, and a D[4,3] particle size for the solid form of about 5 µm to about 200 µm.

9. The pharmaceutical composition of claim 8, wherein the composition comprises about 50 mg of the hydrobromide salt.

* * * * *